(12) United States Patent
Casale et al.

(10) Patent No.: US 12,002,559 B2
(45) Date of Patent: Jun. 4, 2024

(54) DISCOVERY PLATFORM

(71) Applicant: Insitro, Inc., South San Francisco, CA (US)

(72) Inventors: Francesco Paolo Casale, San Francisco, CA (US); Michael Bereket, San Carlos, CA (US); Matthew Albert, San Francisco, CA (US)

(73) Assignee: INSITRO, INC., South San Francisco, CA (US)

( * ) Notice: Subject to any disclaimer, the term of this patent is extended or adjusted under 35 U.S.C. 154(b) by 0 days.

(21) Appl. No.: 18/336,905

(22) Filed: Jun. 16, 2023

(65) Prior Publication Data

US 2023/0360758 A1    Nov. 9, 2023

Related U.S. Application Data

(63) Continuation of application No. PCT/US2022/075006, filed on Aug. 16, 2022.
(Continued)

(51) Int. Cl.
*G16H 15/00* (2018.01)
*G06T 7/00* (2017.01)
(Continued)

(52) U.S. Cl.
CPC ........... *G16H 20/10* (2018.01); *G06T 7/0012* (2013.01); *G16H 15/00* (2018.01); *G16H 30/20* (2018.01)

(58) Field of Classification Search
None
See application file for complete search history.

(56) References Cited

U.S. PATENT DOCUMENTS

| 10,467,754 B1 | 11/2019 | Ando et al. |
| 11,423,256 B2 | 8/2022 | Marie-Nelly et al. |

(Continued)

FOREIGN PATENT DOCUMENTS

| WO | WO-2010082096 A2 | 7/2010 |
| WO | WO-2020113237 A1 | 6/2020 |
| WO | WO-2023023507 A1 | 2/2023 |

OTHER PUBLICATIONS

Taylor-Weiner, Amaro, et al. "A machine learning approach enables quantitative measurement of liver histology and disease monitoring in NASH." Hepatology 74.1 (2021): 133-147. (Year: 2021).*

(Continued)

*Primary Examiner* — Samah A Beg
(74) *Attorney, Agent, or Firm* — MORRISON & FOERSTER LLP

(57) ABSTRACT

The present disclosure relates to a discovery platform including machine-learning techniques for using medical imaging data to study a phenotype of interest, such as complex diseases with weak or unknown genetic drivers. An exemplary method of identifying a covariant of interest with respect to a phenotype comprises: receiving covariant information of a covariate class and corresponding phenotypic image data related to the phenotype obtained from a group of clinical subjects; inputting the phenotypic image data into a trained unsupervised machine-learning model to obtain a plurality of embeddings in a latent space, each embedding corresponding to a phenotypic state reflected in the phenotypic image data; and determining, based on the covariant information for the group of clinical subjects, the plurality of embeddings, and one or more linear regression models, an association between each candidate covariant of a plurality of candidate covariants and the phenotype state to identify the covariant of interest.

23 Claims, 36 Drawing Sheets

Related U.S. Application Data

(60) Provisional application No. 63/233,707, filed on Aug. 16, 2021.

(51) Int. Cl.
  *G16H 20/10* (2018.01)
  *G16H 30/20* (2018.01)

(56) References Cited

U.S. PATENT DOCUMENTS

| | | | |
|---|---|---|---|
| 11,875,506 B1 | 1/2024 | Herve et al. | |
| 2008/0201083 A1 | 8/2008 | Hata et al. | |
| 2017/0204359 A1 | 7/2017 | Ando et al. | |
| 2019/0295721 A1* | 9/2019 | Madabhushi | G06N 3/08 |
| 2019/0371471 A1* | 12/2019 | Tan | G16B 25/10 |
| 2020/0005461 A1 | 1/2020 | Yip | |
| 2020/0105413 A1* | 4/2020 | Vladimirova | G16H 20/30 |
| 2020/0258223 A1 | 8/2020 | Yip et al. | |
| 2020/0388287 A1 | 12/2020 | Anushiravani et al. | |
| 2021/0172931 A1 | 6/2021 | Larsen et al. | |
| 2021/0200989 A1 | 7/2021 | Courtiol et al. | |
| 2021/0256699 A1 | 8/2021 | Wainrib et al. | |
| 2021/0271847 A1 | 9/2021 | Courtiol et al. | |
| 2022/0059240 A1 | 2/2022 | Schaeffer et al. | |
| 2022/0367053 A1 | 11/2022 | Mahmood et al. | |
| 2023/0026189 A1 | 1/2023 | Kamato et al. | |
| 2023/0036156 A1 | 2/2023 | Ho et al. | |
| 2023/0142909 A1 | 5/2023 | Zhao | |

OTHER PUBLICATIONS

Taylor-Weiner et al., (2021). "A Machine Learning Approach Enables Quantitative Measurement of Liver Histology and Disease Monitoring in NASH," Hepatology, 74(1):133-147.
De Jong et al., (2021). "Towards Realizing the Vision of Precision Medicine: AI Based Prediction of Clinical Drug Response Authors," Brain, 144:1738-1750.
International Search Report and Written Opinion received for International Patent Application No. PCT/US2022/075006 mailed on Jan. 27, 2023, 19 pages.
Arslan et al., (2022). "Deep learning can predict multi-omic biomarkers from routine pathology images: A systematic large-scale study," BioRxiv, 477189, 44 pages.
Courtiol et al., (2020). "Classification And Disease Localization In Histopathology Using Only Global Labels: A Weakly-Supervised Approach," arXiv, 1802.02212, 13 pages.
Galton, (1886). "Regression Towards Mediocrity in Hereditary Stature," The Journal of the Anthropological Institute of Great Britain and Ireland, 15:246-263.
Goldsborough et al., (2017). "CytoGAN: generative modeling of cell images," BioRxiv, 227645, 6 pages.
Ingale et al., (2023). "Prediction of met overexpression in non-small cell lung adenocarcinomas from hematoxylin and eosin images," arXiv, 2310.07682, 45 pages.
International Search Report and Written Opinion received for International Patent Application No. PCT/US2022/080200 mailed on May 23, 2023, 20 pages.
Kopf et al., (2021). "Latent representation learning in biology and translational medicine," Patterns, 2(3):100198, 15 pages.
Liu et al., (2018). "An integrated toga pan-cancer clinical data resource to drive high-quality survival outcome analytics," Cell, 173(2):400-416, 29 pages.
Ubbens et al., (2020). "Latent space phenotyping: automatic image-based phenotyping for treatment studies," Plant Phenomics, 2020:5801869, 13 pages.
Wells et al., (2009). "Phase contrast microscopy analysis of breast tissue: differences in benign vs. malignant epithelium and stroma," Anal Quant Cytol Histol., 31(4):197-207, 18 pages.
Courtiol et al., (2019). "Deep learning-based classification of mesothelioma improves prediction of patient outcome," Nature Medicine, 25(10):1519-1525.

\* cited by examiner

200

202
inputting a plurality of medical images obtained from a group of clinical subjects into an unsupervised machine-learning model to obtain a plurality of embeddings in a latent space, each embedding corresponding to a phenotypic state relative to the disease of interest reflected in one or more of the plurality of medical images

↓

204
Obtaining a plurality of predicted medical diagnosis scores corresponding to the plurality of embeddings using a linear regression model, each medical diagnosis score indicative of a state of the disease of interest or its progression

↓

206
Associating the plurality of medical diagnosis scores with each candidate genetic variant of a plurality of candidate genetic variants expressed by the group of clinical subjects from whom the plurality of medical images was taken

↓

208
Determining, based on the association, a correlation metric between the disease of interest and each genetic variant of interest, the correlation metric indicative of impact of the genetic variant of interest on the disease of interest

FIG. 2

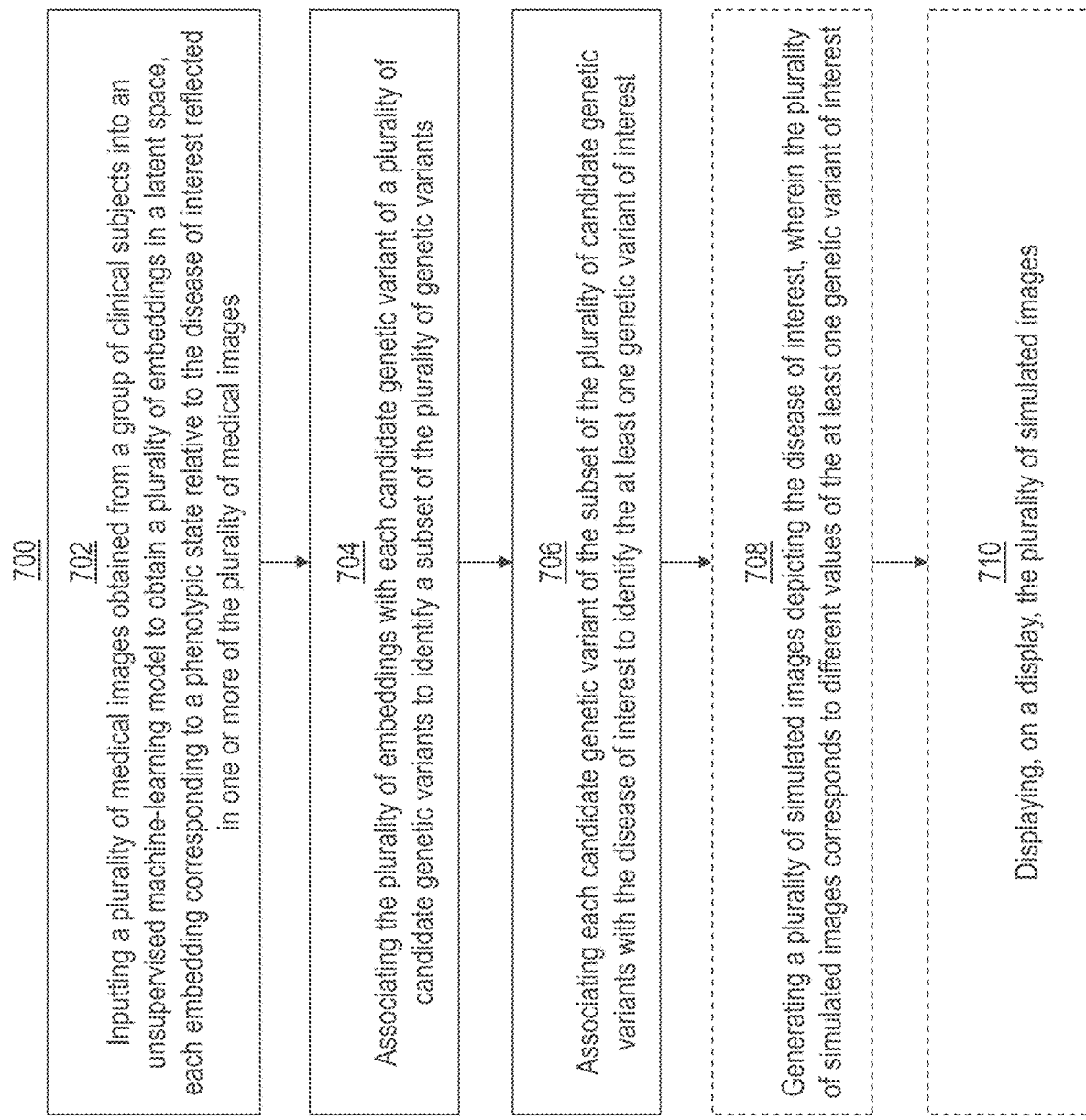

2202: Obtaining medical images comprising: (a) a plurality of baseline placebo medical images of a placebo group of subjects captured before a placebo is administered to the placebo group, (b) a plurality of follow-up placebo medical images of the placebo group of subjects captured after the placebo is administered to the placebo group, (c) a plurality of baseline treatment medical images of a treatment group of subjects captured before the treatment is administered to the treatment group, and (d) a plurality of follow-up treatment medical images of the treatment group of subjects captured after the treatment is administered to the treatment group 2204: Inputting the medical images into a trained unsupervised machine-learning model to obtain a plurality of embeddings, each embedding corresponding to a phenotypic state relative to the disease of interest reflected in one or more of the medical images 2206: Inputting the plurality of embeddings into a trained linear regression model to obtain a plurality of predicted continuous medical diagnosis scores, each predicted continuous medical diagnosis score indicative of a state of the disease of interest 2208: Determining a plurality of placebo progression scores and a plurality of treatment progression scores based on the predicted continuous medical diagnosis scores 2210: Associating the plurality of placebo progression scores and the plurality of treatment progression scores with the treatment; determining, based on the association, a correlation metric between the plurality of disease progression scores and the treatment FIG. 26A    FIG. 26B  NASH Progression GWAS

DISCOVERY PLATFORM

CROSS-REFERENCE TO RELATED APPLICATIONS

This application is a continuation application of International Application No. PCT/US2022/075006, filed internationally on Aug. 16, 2022, which claims priority to U.S. Provisional Application No. 63/233,707, filed 16 Aug. 2021, the contents of each of which are incorporated herein by reference in its entirety.

FIELD OF INVENTION

The present disclosure relates generally to a discovery platform, and more specifically to machine-learning techniques for using medical imaging data to study a phenotype of interest, such as complex diseases with weak or unknown genetic drivers.

BACKGROUND

Many diseases afflicting human beings are driven in part by genetics. Specifically, individuals having one or more particular genetic variants or mutations may be more susceptible to developing a disease or, following disease onset, to experience more rapid or severe disease progression. Especially for diseases that may be impacted by multiple genetic variants, it has proven difficult to identify the specific factors that may cause a subject having a certain genetic background to incur a disease, or to predict how that disease is likely to progress in that subject upon onset. Moreover, slight genetic variants among subjects who are otherwise susceptible to a disease may impact how well each subject is likely to respond to a given therapeutic intervention, with respect to both efficacy and safety. Thus, a lack of understanding regarding how specific genetic variants may influence disease onset and progression, and, in turn, how candidate therapies may impact regression of the disease or adverse reactions in clinical subjects, pose significant stumbling blocks to effective drug development.

Recent advances in the computational analysis of histopathology images have enabled a deeper understanding of disease phenotypes as expressed in various human subjects suffering from a particular disease. Recent advances in computational analysis of genetic variants in subjects and how, in turn, multiple genetic variants may influence disease susceptibility risk have enabled better understanding of the precise genetic underpinnings of certain diseases. Still, opportunities remain for better leveraging these types of advances for identifying disease targets, predicting disease onset or the shape of disease progression in human subjects, predicting likely responses to therapeutic candidates among subjects with different genetic backgrounds, identifying suitable patent cohorts to receive a particular therapy, and generally designing clinical trials to optimize outcomes.

BRIEF SUMMARY

An exemplary method of identifying a covariant of interest with respect to a phenotype comprises: receiving covariant information of a covariate class and corresponding phenotypic data related to the phenotype obtained from a group of clinical subjects; inputting the phenotypic data into a trained unsupervised machine-learning model to obtain a plurality of embeddings in a latent space, each embedding corresponding to a phenotypic state reflected in the phenotypic data; and determining, based on the covariant information for the group of clinical subjects, the plurality of embeddings, and one or more linear regression models, an association between each candidate covariant of a plurality of candidate covariants and the phenotype to identify the covariant of interest.

In some embodiments, the phenotype comprises a disease of interest, a gene expression, metabolomics, proteomics, or lipidomics.

In some embodiments, the phenotypic data comprises medical imaging data, histopathology data, clinical biomarker data, or genomic biomarker data.

In some embodiments, the covariate class comprises demographic information, clinical covariates, or genomic data.

In some embodiments, determining the association between each candidate covariant and the phenotype comprises: inputting each embedding of the plurality of embeddings into a linear regression model to receive a predicted continuous score for each embedding of the plurality of embeddings to obtain a plurality of continuous scores; associating (e.g., testing for association) the plurality of predicted continuous scores with a candidate covariant expressed by the group of clinical subjects; determining, based on the association, a correlation metric between the phenotype and the candidate covariant, the correlation metric indicative of the impact of the candidate covariant on the phenotype.

In some embodiments, determining the association between the candidate covariant and the phenotype comprises: associating the plurality of embeddings with each candidate covariant of the plurality of candidate covariates to identify a subset of the plurality of candidate covariant; and associating each candidate covariant in the subset with the phenotype to identify the at least one covariant of interest.

In some embodiments, the method further comprises: generating, based on the at least one genetic variant of interest, a plurality of simulated images depicting the phenotype; and displaying, on a display, the plurality of simulated images.

In some embodiments, the method further comprises: identifying a relationship between the at least one genetic variant of interest and the phenotype.

In some embodiments, the relationship is a causal relationship.

In some embodiments, the method further comprises: providing a diagnosis in a new subject based on the relationship.

In some embodiments, the method further comprises: developing a treatment based on the relationship.

In some embodiments, the method further comprises: administering, adjusting, or applying a treatment based on the relationship.

In some embodiments, the method further comprises: providing a medical recommendation based on the relationship.

In some embodiments, the method further comprises: identifying a biological target for treating the disease of interest based on the relationship.

In some embodiments, the disease of interest is non-alcoholic steatohepatitis (NASH).

An exemplary method of identifying at least one genetic variant of interest with respect to a disease of interest comprises: inputting a plurality of medical images obtained from a group of clinical subjects into a trained unsupervised machine-learning model to obtain a plurality of embeddings in a latent space, each embedding corresponding to a phenotypic state relative to the disease of interest reflected in one or more of the plurality of medical images; inputting each embedding of the plurality of embeddings into a trained linear regression model to receive a predicted continuous medical diagnosis score for each embedding of the plurality of embeddings to obtain a plurality of predicted medical diagnosis scores, each predicted continuous medical diagnosis score indicative of a state of the disease of interest; associating the plurality of predicted continuous medical diagnosis scores with each candidate genetic variant of a plurality of candidate genetic variants expressed by the group of clinical subjects from whom the plurality of medical images was taken; determining, based on the association, a correlation metric between the disease of interest and each candidate genetic variant to identify the at least one genetic variant of interest from the plurality of candidate genetic variants, the correlation metric indicative of the impact of the candidate genetic variant on the disease of interest.

In some embodiments, the method further comprises: comparing the correlation metric with a predefined threshold.

In some embodiments, the method further comprises: identifying, based on the comparison, a relationship between the genetic variant of interest and the disease of interest.

In some embodiments, the relationship is a causal relationship.

In some embodiments, the method further comprises: diagnosing the disease of interest in a new subject based on the relationship.

In some embodiments, the method further comprises: developing a treatment based on the relationship.

In some embodiments, the method further comprises: administering, adjusting, or applying a treatment based on the relationship.

In some embodiments, the method further comprises: providing a medical recommendation based on the relationship.

In some embodiments, the method further comprises: identifying a biological target for treating the disease of interest based on the relationship.

In some embodiments, the disease of interest is non-alcoholic steatohepatitis (NASH).

In some embodiments, the plurality of medical images comprises biopsy images.

In some embodiments, the biopsy images correspond to one or more clinical trials.

In some embodiments, the method further comprises: dividing a medical image of the plurality of images into a plurality of image tiles; inputting each image tile of the plurality of image tiles into the unsupervised machine-learning model to receive a tile embedding for each image tile to obtain a plurality of tile embeddings; and aggregating the tile embeddings to obtain an embedding of the plurality of embeddings.

In some embodiments, aggregating the tile embeddings comprises averaging the tile embeddings.

In some embodiments, the unsupervised machine-learning model is a contrastive model.

In some embodiments, the contrastive model is a SimCLR model.

In some embodiments, the unsupervised machine-learning model is trained at least partially based on the plurality of medical images.

In some embodiments, the unsupervised machine-learning model is fine-tuned based on the plurality of medical images.

In some embodiments, the linear regression model is a linear mixed model.

In some embodiments, the linear regression model is fitted based on the plurality of embeddings and a plurality of assigned medical diagnosis scores corresponding to the plurality of embeddings.

In some embodiments, the plurality of assigned medical diagnosis scores are provided by one or more medical practitioners.

In some embodiments, each assigned medical diagnosis score of the plurality of assigned medical diagnosis scores is selected from a set of predefined values.

In some embodiments, the plurality of predicted medical diagnosis scores is a plurality of predicted fibrosis scores, a plurality of predicted lobular inflammation scores, or a plurality of predicted steatosis scores.

In some embodiments, the plurality of predicted medical diagnosis scores comprises a disease progression score obtained as the difference of predicted medical diagnosis scores at different measurements during the clinical trial.

In some embodiments, the plurality of predicted medical diagnosis scores comprise disease progression scores calculated as the difference between predicted medical diagnosis scores reflecting different measurements obtained during the clinical trial.

In some embodiments, the plurality of predicted medical diagnosis scores comprise disease progression scores obtained as the slope determined by a linear model trained on predicted medical diagnosis scores reflecting different measurements obtained for each individual during the clinical trial.

In some embodiments, the variant-specific model is a linear model.

In some embodiments, the variant-specific model is fitted based on the plurality of predicted medical diagnosis scores and a plurality of values indicative of the candidate genetic variant.

In some embodiments, determining the correlation metric comprises determining a P value based on the variant-specific model.

An exemplary method of identifying at least one genetic variant of interest with respect to a disease of interest comprises: inputting a plurality of medical images obtained from a group of clinical subjects into a trained unsupervised machine-learning model to obtain a plurality of embeddings in a latent space, each embedding corresponding to a phenotypic state relative to the disease of interest reflected in one or more of the plurality of medical images; associating the plurality of embeddings with each candidate genetic variant of a plurality of candidate genetic variants to identify a subset of the plurality of candidate genetic variants, wherein the subset of the plurality of genetic variants is associated with histological features reflected in the plurality of medical images; and associating each candidate genetic variant of the subset of the plurality of candidate genetic variants with the disease of interest to identify the at least one genetic variant of interest from the subset.

In some embodiments, the method further comprises: generating, based on the at least one genetic variant of interest, a plurality of simulated images depicting the disease of interest; and displaying, on a display, the plurality of simulated images.

In some embodiments, the method further comprises: identifying a relationship between the at least one genetic variant of interest and the disease of interest.

In some embodiments, the relationship is a causal relationship.

In some embodiments, the method further comprises: diagnosing the disease of interest in a new subject based on the relationship.

In some embodiments, the method further comprises: developing a treatment based on the relationship.

In some embodiments, the method further comprises: administering, adjusting, or applying a treatment based on the relationship.

In some embodiments, the method further comprises: providing a medical recommendation based on the relationship.

In some embodiments, the method further comprises: identifying a biological target for treating the disease of interest based on the relationship.

In some embodiments, the disease of interest is non-alcoholic steatohepatitis (NASH).

In some embodiments, the plurality of medical images comprises biopsy images.

In some embodiments, the biopsy images correspond to one or more clinical trials.

In some embodiments, the method further comprises: dividing a medical image of the plurality of images into a plurality of image tiles; inputting each image tile of the plurality of image tiles into the unsupervised machine-learning model to receive a tile embedding for each image tile to obtain a plurality of tile embeddings; and aggregating the tile embeddings to obtain an embedding of the plurality of embeddings.

In some embodiments, aggregating the tile embeddings comprises averaging the tile embeddings.

In some embodiments, the unsupervised machine-learning model is a contrastive model.

In some embodiments, the contrastive model is a SimCLR model.

In some embodiments, the unsupervised machine-learning model is trained at least partially based on the plurality of medical images.

In some embodiments, the unsupervised machine-learning model is fine-tuned based on the plurality of medical images.

In some embodiments, associating the plurality of embeddings with each genetic variant of the plurality of genetic variants to identify the subset of the plurality of genetic variants comprises: generating, for a candidate genetic variant of the plurality of candidate genetic variants, a variant-specific model configured to receive an embedding and output a value of the candidate genetic variant; and evaluating the variant-specific model to determine whether to include the candidate genetic variant in the subset.

In some embodiments, evaluating the variant-specific model comprises: calculating a correlation metric based on the variant-specific model; and comparing the correlation metric with a predefined threshold.

In some embodiments, the correlation metric is a P value associated with the variant-specific model.

In some embodiments, associating each genetic variant of the subset of the plurality of genetic variants with the disease of interest to identify the at least one genetic variant of interest comprises: generating, for a genetic variant in the subset, a variant-specific model configured to receive a value indicative of the genetic variant and output a medical diagnosis score related to the disease of interest; and evaluating the variant-specific model to determine whether the candidate genetic variant is the at least one genetic variant of interest.

In some embodiments, evaluating the variant-specific model comprises: calculating a correlation metric based on the variant-specific model; and comparing the correlation metric with a predefined threshold.

In some embodiments, the correlation metric is a P value associated with the variant-specific score prediction model.

An exemplary method of evaluating a treatment with respect to progression of a disease of interest, comprising: obtaining a plurality of baseline placebo images of a placebo group of subjects captured before a placebo is administered to the placebo group and a plurality of follow-up placebo images of the placebo group of subjects captured after the placebo is administered to the placebo group; obtaining a plurality of placebo progression embeddings based on the plurality of baseline placebo images and the plurality of follow-up placebo images; obtaining a plurality of baseline treatment images of a treatment group of subjects captured before the treatment is administered to the treatment group and a plurality of follow-up treatment images of the treatment group of subjects captured after the treatment is administered to the treatment group; obtaining a plurality of treatment progression embeddings based on the plurality of baseline treatment images and the plurality of follow-up treatment images; generating a classification model for determining whether a patient has received the placebo or the treatment based on the plurality of treatment progression embeddings, wherein outputs of the classification model are indicative of drug response histological phenotype (DRP); and determining, based on the classification model, a correlation metric between the treatment and the progression of the disease of interest.

In some embodiments, the correlation metric is a P value.

In some embodiments, the method further comprises: comparing the correlation metric with a predefined threshold.

In some embodiments, the method further comprises: identifying, based on the comparison, an association between the treatment and progression of the disease of interest.

In some embodiments, the method further comprises: prescribing the treatment in a new subject based on the association.

In some embodiments, the method further comprises: administering the treatment based on the association.

In some embodiments, the method further comprises: adjusting the treatment based on the association.

In some embodiments, the method further comprises: providing a medical recommendation based on the association.

In some embodiments, the method further comprises: generating a report based on the association.

In some embodiments, the disease of interest is non-alcoholic steatohepatitis (NASH).

In some embodiments, obtaining the plurality of placebo progression embeddings comprises: inputting the plurality of baseline placebo images into a trained unsupervised machine-learning model to obtain a plurality of baseline placebo embeddings in a latent space; inputting the plurality of follow-up placebo images into the trained unsupervised machine-learning model to obtain a plurality of follow-up placebo embeddings in the latent space; inputting the plurality of baseline placebo embeddings into a trained linear model to obtain a plurality of predicted follow-up placebo embeddings in the latent space; determining the plurality of placebo progression embeddings by calculating differences between the plurality of follow-up placebo embeddings and the plurality of predicted follow-up placebo embeddings.

In some embodiments, obtaining the plurality of treatment progression embeddings comprises: inputting the plurality of baseline treatment images into the trained unsupervised machine-learning model to obtain a plurality of baseline treatment embeddings in a latent space; inputting the plurality of follow-up treatment images into the trained unsupervised machine-learning model to obtain a plurality of follow-up treatment embeddings in the latent space; inputting the plurality of baseline treatment embeddings into the trained linear model to obtain a plurality of predicted follow-up treatment embeddings in the latent space; determining the plurality of treatment progression embeddings by calculating differences between the plurality of follow-up treatment embeddings and the plurality of predicted follow-up treatment embeddings.

In some embodiments, the unsupervised machine-learning model is a contrastive model.

In some embodiments, the contrastive model is a SimCLR model.

In some embodiments, the trained linear model is configured to receive a baseline embedding and output a predicted follow-up embedding.

In some embodiments, the trained linear model is a linear mixed model.

In some embodiments, the placebo group is a first placebo group, and wherein the linear model is trained using image data from a second placebo group different from the first placebo group.

In some embodiments, the classification model is configured to receive an input progression embedding and output a classification result indicating whether a patient has received the placebo or the treatment.

In some embodiments, the plurality of baseline placebo images, the plurality of follow-up placebo images, the plurality of baseline treatment images, and the plurality of follow-up treatment images are biopsy images.

An exemplary method of identifying a covariant of interest with respect to drug response histological phenotype (DRP) of a treatment comprises: receiving covariant information of a covariate class obtained from a group of clinical subjects; receiving a plurality of baseline images and a plurality of follow-up images from the group of clinical subjects; obtaining a plurality of progression embeddings based on the plurality of baseline images and the plurality of follow-up images; inputting the plurality of progression embeddings into a trained classification models to obtain a plurality of classification results indicative of DRP values of the group of clinical subjects; and determining, based on the covariant information for the group of clinical subjects, the plurality of classification results, and one or more linear regression models, an association between each candidate covariant of a plurality of candidate covariants and the DRP values to identify the covariant of interest.

In some embodiments, the plurality of candidate covariants comprises a plurality of candidate missense variants.

In some embodiments, the plurality of candidate covariants comprises a plurality of candidate genes.

In some embodiments, the covariate class comprises demographic information, clinical covariates, or genomic data.

In some embodiments, the method further comprises: diagnosing a disease of interest in a new subject based on the identified covariant of interest.

In some embodiments, the method further comprises: developing a treatment based on the identified covariant of interest.

In some embodiments, the method further comprises: administering, adjusting, or applying the treatment based on the identified covariant of interest.

In some embodiments, the method further comprises: providing a medical recommendation based on the identified covariant of interest.

In some embodiments, the method further comprises: identifying a biological target based on the identified covariant of interest.

In some embodiments, the plurality of medical images comprises biopsy images.

In some embodiments, obtaining the plurality of progression embeddings based on the plurality of baseline images and the plurality of follow-up images comprises: inputting the plurality of baseline images into a trained unsupervised machine-learning model to obtain a plurality of baseline embeddings in a latent space; inputting the plurality of follow-up images into the trained unsupervised machine-learning model to obtain a plurality of follow-up embeddings in the latent space; inputting the plurality of baseline embeddings into a trained linear model to obtain a plurality of predicted follow-up embeddings in the latent space; determining the plurality of progression embeddings by calculating differences between the plurality of follow-up embeddings and the plurality of predicted follow-up embeddings.

In some embodiments, the unsupervised machine-learning model is a contrastive model.

In some embodiments, the contrastive model is a SimCLR model.

In some embodiments, the trained linear model is configured to receive a baseline embedding and output a predicted follow-up embedding.

In some embodiments, the trained linear model is a linear mixed model.

In some embodiments, the trained classification model is configured to receive an input progression embedding and determine whether a patient has received the placebo or the treatment.

In some embodiments, identifying the covariant of interest comprises: for a candidate covariant of the plurality of candidate covariants: generating a model based on the DRP values and the covariant information of the group of clinical subjects; and determining a correlation metric based on the model.

In some embodiments, the correlation metric is a P value.

In some embodiments, the method further comprises: comparing the correlation metric against a predefined threshold to determine if the candidate covariant is the covariant of interest.

An exemplary method of evaluating a treatment with respect to progression of a disease of interest comprises: obtaining medical images comprising: (a) a plurality of baseline placebo images of a placebo group of subjects captured before a placebo is administered to the placebo group, (b) a plurality of follow-up placebo images of the placebo group of subjects captured after the placebo is administered to the placebo group, (c) a plurality of baseline treatment images of a treatment group of subjects captured before the treatment is administered to the treatment group, and (d) a plurality of follow-up treatment images of the treatment group of subjects captured after the treatment is administered to the treatment group; inputting the medical images into a trained unsupervised machine-learning model to obtain a plurality of embeddings, each embedding corresponding to a phenotypic state relative to the disease of interest reflected in one or more of the medical images; inputting the plurality of embeddings into a trained linear regression model to obtain a plurality of predicted continuous medical diagnosis scores, each predicted continuous medical diagnosis score indicative of a state of the disease of interest; determining a plurality of placebo progression scores and a plurality of treatment progression scores based on the predicted continuous medical diagnosis scores; associating the plurality of placebo progression scores and the plurality of treatment progression scores with the treatment; determining, based on the association, a correlation metric between the plurality of disease progression scores and the treatment.

In some embodiments, inputting the medical images into a trained unsupervised machine-learning model to obtain the plurality of embeddings comprises: inputting (a) into the trained unsupervised machine-learning model to obtain a plurality of baseline placebo embeddings; inputting (b) into the trained unsupervised machine-learning model to obtain a plurality of follow-up placebo embeddings; inputting (c) into a trained unsupervised machine-learning model to obtain a plurality of baseline treatment embeddings; inputting (d) into the trained unsupervised machine-learning model to obtain a plurality of follow-up treatment embeddings.

In some embodiments, inputting the plurality of embeddings into the trained linear regression model comprises: inputting the plurality of baseline placebo embeddings into the trained linear model to obtain a plurality of baseline placebo scores; inputting the plurality of follow-up placebo embeddings into the trained linear model to obtain a plurality of follow-up placebo scores; inputting the plurality of baseline treatment embeddings into the trained linear model to obtain a plurality of baseline treatment scores; and inputting the plurality of follow-up treatment embeddings into the trained linear model to obtain a plurality of follow-up treatment scores.

In some embodiments, determining the plurality of placebo progression scores and the plurality of treatment progression scores comprises: determining differences between the plurality of baseline placebo scores and the plurality of follow-up placebo scores to determine the plurality of placebo progression scores; and determining differences between the plurality of baseline treatment scores and the plurality of follow-up treatment scores to determine the plurality of treatment progression scores.

In some embodiments, determining the plurality of placebo progression scores and the plurality of treatment progression scores comprises: determining, for each subject in the placebo group, a slope of a linear model fitted at least based on a baseline placebo score and a follow-up placebo score of the subject in the placebo group; and determining, for each subject in the treatment group, a slope of a linear model fitted at least based on a baseline placebo score and a follow-up placebo score of the subject in the treatment group.

In some embodiments, associating the plurality of placebo progression scores and the plurality of treatment progression scores with the treatment comprises generating a model configured to receive an indication of whether a patient received the treatment and output a predicted disease progression score.

In some embodiments, the correlation metric is P value of the model.

In some embodiments, the method further comprises: comparing the correlation metric with a predefined threshold.

In some embodiments, the method further comprises: identifying, based on the comparison, an association between the treatment and the disease of interest.

In some embodiments, the method further comprises: administering, adjusting, or applying the treatment based on the association.

In some embodiments, the method further comprises: providing a medical recommendation based on the association.

In some embodiments, the disease of interest is non-alcoholic steatohepatitis (NASH).

In some embodiments, the unsupervised machine-learning model is a contrastive model.

In some embodiments, the contrastive model is a SimCLR model.

In some embodiments, the linear regression model is a linear mixed model.

In some embodiments, the linear regression model is fitted based on a plurality of assigned medical diagnosis scores.

In some embodiments, the plurality of assigned medical diagnosis scores are provided by one or more medical practitioners.

In some embodiments, each assigned medical diagnosis score of the plurality of assigned medical diagnosis scores is selected from a set of predefined values.

In some embodiments, the plurality of predicted medical diagnosis scores is a plurality of predicted fibrosis scores, a plurality of predicted lobular inflammation scores, or a plurality of predicted steatosis scores.

An exemplary method of identifying a patient subgroup of interest comprises: inputting a plurality of medical images obtained from a group of clinical subjects into a trained unsupervised machine-learning model to obtain a plurality of embeddings in a latent space; clustering the plurality of embeddings to generate one or more clusters of embeddings; identifying the one or more patient subgroups corresponding to the one or more clusters of embeddings; associating each patient subgroup of the one or more patient subgroups with a covariant to identify the patient subgroup of interest.

In some embodiments, the unsupervised machine-learning model is a contrastive model.

In some embodiments, the contrastive model is a SimCLR model.

In some embodiments, the covariant is a treatment of interest and wherein the patient subgroup of interest is a subgroup in whom the treatment of interest has a significant impact.

In some embodiments, associating each patient subgroup of the one or more patient subgroups with the covariant comprises: generating, for a patient subgroup, a model configured to receive an indication of whether a patient in the patient subgroup received the treatment of interest and output a predicted disease progression; and evaluating the model to determine if the patient subgroup is the patient subgroup of interest.

In some embodiments, evaluating the model comprises determining a correlation metric of the model and comparing the correlation metric against a predefined threshold.

In some embodiments, the correlation metric is a P value.

In some embodiments, the generated model is trained by disease progression values of subjects in the patient subgroup.

In some embodiments, the disease progression values comprise medical diagnosis scores of the subjects in the patient subgroup.

In some embodiments, the disease progression values comprise progression scores of the subjects in the patient subgroup.

In some embodiments, the disease progression values comprise DRP values of the subjects in the patient subgroup.

In some embodiments, the covariant is a progression of a disease of interest and wherein the patient subgroup of interest is a subgroup that has a significant association with the progression of the disease of interest.

In some embodiments, associating each patient subgroup of the one or more patient subgroups with the covariant comprises: generating, for a patient subgroup, a model configured to receive an indication of whether a patient belongs to the patient subgroup and output a predicted disease progression; and evaluating the model to determine if the patient subgroup is the patient subgroup of interest.

In some embodiments, evaluating the model comprises determining a correlation metric of the model and comparing the correlation metric against a predefined threshold.

In some embodiments, the correlation metric is a P value.

In some embodiments, the generated model is trained by disease progression values of the group of clinic subjects.

In some embodiments, the disease progression values comprise medical diagnosis scores of the subjects in the patient subgroup, progression scores of the subjects in the patient subgroup, or DRP values of the subjects in the patient subgroup.

In some embodiments, the covariant is an adverse side effect and wherein the patient subgroup of interest is a subgroup that has a significant association with the adverse side effect.

In some embodiments, associating each patient subgroup of the one or more patient subgroups with the covariant comprises: generating, for a patient subgroup, a model configured to receive an indication of whether a patient in the patient subgroup belongs to the patient subgroup and predict if the patient has the adverse side effect; and evaluating the model to determine if the patient subgroup is the patient subgroup of interest.

In some embodiments, evaluating the model comprises determining a correlation metric of the model and comparing the correlation metric against a predefined threshold.

In some embodiments, the correlation metric is a P value.

An exemplary method of identifying at least one biological target of interest with respect to a disease of interest comprises: inputting a plurality of medical images obtained from a group of clinical subjects into a trained unsupervised machine-learning model to obtain a plurality of embeddings in a latent space, each embedding corresponding to a phenotypic state relative to the disease of interest reflected in one or more of the plurality of medical images; associating the plurality of embeddings with each candidate biological target of a plurality of candidate biological targets to identify a subset of the plurality of candidate biological targets, wherein the subset of the plurality of biological targets is associated with phenotypic features reflected in the plurality of medical images; and associating each candidate biological target of the subset of the plurality of candidate biological targets with the disease of interest to identify the at least one biological target of interest from the subset having a functional impact on the onset of the disease of interest or its progression; and identifying a biological target for modulation, wherein such modulation is designed to alter, offset, mitigate, supplement or complement the functional impact of the at least one biological target on the disease of interest.

An exemplary system comprises: one or more processors; a memory; and one or more programs, wherein the one or more programs are stored in the memory and configured to be executed by the one or more processors, the one or more programs including instructions for performing any of the methods described herein.

An exemplary non-transitory computer-readable storage medium stores one or more programs, the one or more programs comprising instructions, which when executed by one or more processors of an electronic device, cause the electronic device to perform any of the methods described herein.

DESCRIPTION OF THE FIGURES

FIG. 2 illustrates an exemplary method for identifying a genetic variant of interest with respect to a disease of interest, in accordance with some embodiments.

FIG. 7 illustrates an exemplary process for identifying at least one genetic variant of interest with respect to a disease of interest, according to various embodiments.

FIG. 22 illustrates an exemplary method of evaluating a treatment with respect to progression of a disease of interest, in accordance with some embodiments.

DETAILED DESCRIPTION

Figure 1:
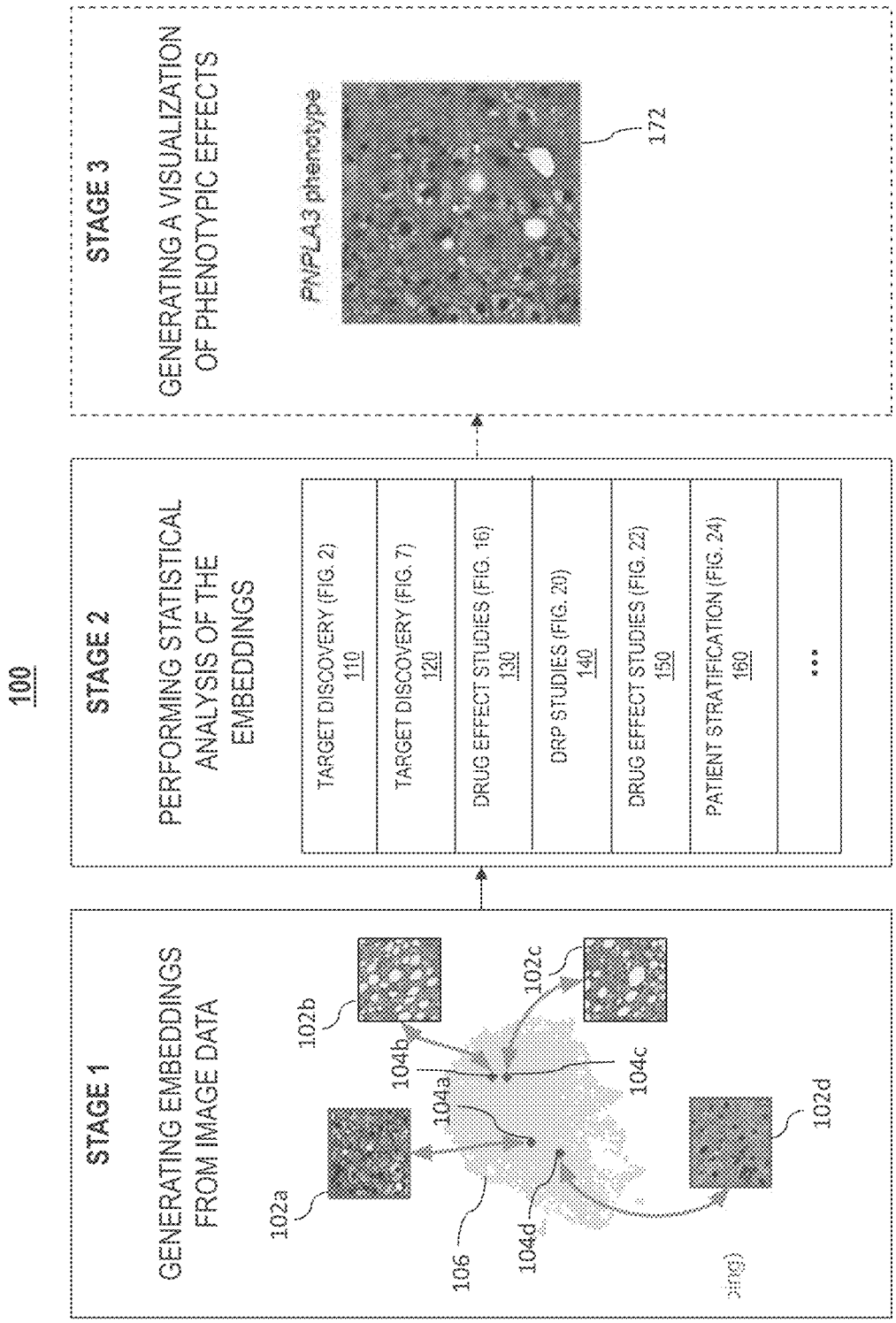
FIG. 1 illustrates an architecture of an exemplary discovery platform, in accordance with some embodiments.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Disclosed herein are methods, systems, electronic devices, non-transitory storage media, and apparatuses directed to providing a discovery platform. The discovery platform can be applied to complex diseases such as polygenic diseases to enable target identification, cross-clinical trial analysis, and enhance interpretability. The discovery platform can be applied to weak or unknown genetic drivers. For example, NASH is a disease with an unknown genetic architecture. In some embodiments, the discovery platform can identify a relationship (e.g., a causal relationship) between the genetic variant of interest and the disease of interest such as NASH. The identified relationship can be used to determine the likelihood that a disease of interest will develop in a new subject or to more confidently diagnose the presence of the disease in a new subject given certain symptoms or the presence of other disease-associated factors. Additionally, if the genetic variant is identified in the new subject, a diagnosis or prognosis of the disease of interest can be provided accordingly, including a prognosis regarding how the disease can be expected to progress. For example, if the genetic variant of interest is discovered for NASH, genomic testing can be performed on a new subject to detect the variant. If the variant is present, the system can predict disease onset, provide a diagnosis, and/or provide a prognosis regarding how the disease may progress for the new subject.

In some embodiments, the discovery platform comprises a plurality of stages. At the first stage, an exemplary system (e.g., one or more electronic devices) generates embeddings based on medical imaging data related to a phenotype of interest such as a disease of interest. An embedding is a mapping of a variable to a vector (an array of numbers). As described herein, an embedding refers to a vector representation of a phenotypic state relative to the disease of interest reflected in the medical imaging data. The embedding captures rich semantic information of the medical imaging data (e.g., features of the microscopic structure of tissues reflected in the image), while excluding information that is not relevant to downstream analyses (e.g., orientation of the image). In an exemplary implementation, the disease of interest is non-alcoholic steatohepatitis (NASH) and the medical images are from hematoxylin & eosin (H&E) stained liver biopsies from a number of clinical trials. The resulting unsupervised embeddings can enable target identification, cross-clinical trial analysis, and enhance interpretability, as described herein.

In some embodiments, the system generates an embedding by inputting medical imaging data into a trained unsupervised machine-learning model such as a contrastive learning algorithm. Contrastive learning models can extract embeddings from imaging data, and the embeddings are linearly predictive of biological endpoints or labels (e.g., progression of the disease of interest) that may otherwise be assigned to such data, as described herein. A suitable contrastive learning model is trained such that it can maximize the similarity between embeddings from different augmentations of the same sample image and minimize the similarity between embeddings of different sample images. For example, the model can extract embeddings from images that are invariant to rotation, flipping, cropping, and color jittering.

In some embodiments, the embeddings can be mean-aggregated and/or normalized before being used for downstream analysis. In some embodiments, normalizing the embeddings comprises performing a variance-stabilizing transformation, which may improve their ability to linearly predict biological endpoints of labels. As described herein, normalization can improve the performance of linear predictive models fitted based on the embeddings. In some embodiments, a linear model fit with normalized embeddings has similar or superior predictive capability as a supervised machine-learning model and is more computationally efficient to generate and apply, as described further herein.

At the second stage, the system performs statistical analysis of the embeddings, for example, using one or more linear regression models. Performing statistical analysis using embeddings rather than imaging data provides a number of technical advantages. First, an embedding captures rich semantic information of the imaging data (e.g., features of the microscopic structure of tissues reflected in the image), while excluding information that is not relevant to the downstream analyses (e.g., orientation of the image). Further, the embedding is of a significantly smaller size than the imaging data it represents. In an exemplary implementation, the embedding can be a 2048-dimensional vector, while the corresponding medical image comprises data corresponding to a large number of pixels (e.g., tens of thousands of pixels, hundreds of thousands of pixels, millions of pixels, and the like).

Further still, the embeddings allow the system to generate (e.g., fit) linear regression models that are configured to receive embeddings as the input and output predictions. In some embodiments, the linear regression models are linear mixed models, which provide a flexible framework for statistical analysis of embeddings of phenotypic variation, including treatments and potential covariate effects. As described herein, linear models generated based on embeddings can provide similar or superior predictive power as supervised machine-learning models (e.g., a neural network configured to receive image data) and are more computationally efficient to train and to apply than supervised machine-learning models.

In some embodiments, the second stage of the discovery platform comprises using the embeddings to obtain fine-grained labels for the medical images, such as continuous scores indicative of the disease of interest. For example, a linear model can be generated (e.g., fitted) based on embeddings and pathologist-assigned, discrete medical diagnosis scores associated with the embeddings. The model can then be applied to the embeddings to predict continuous medical diagnosis scores.

A predicted continuous score has strong advantages over a discrete score assigned by a pathologist. Specifically, the predicted score has a continuous value and thus captures more nuance than a pathologist-assigned, discrete score. The ability to assign continuous scores to the embeddings (and image data) results in higher precision and improved statistical power in downstream analyses, such as obtaining a closer association of each depicted disease state with a genetic variant or variants. For example, the severity of NASH and liver fibrosis is currently histologically assessed by pathologists through the NASH CRN and Ishak stage ordinal scores, such as the Ishak fibrosis score (0-6), the steatosis score (0-3), the lobular inflammation score (0-3), and the ballooning score (0-2). Quantitative analyses of these metrics are challenged by their low-resolution categorization of disease. The linear model can be trained to generate continuous scores from imaging data (e.g., H&E liver biopsy imaging data) that are predictive of pathologist scores. The continuous scores enable a more precise definition of disease progression, empowering longitudinal expression analysis and genetic association studies.

In some embodiments, the system performs association testing between a candidate genetic variant and the disease of interest. Each medical image (e.g., histology image) has associated gene sequences from the human subject from whom the image was taken. The association testing comprises generating (e.g., fitting) a linear model based on the candidate genetic variant and the continuous scores indicative of the disease of interest. The system can generate variant-specific models (e.g., 100,000 models, 1 million models, 10 million models, etc.) for all candidate genetic variants of interest (e.g., 100,000 variants, 1 million variants, 10 million variants, etc.). Each model can be evaluated to determine if there is a significant association between each candidate genetic variant and the disease of interest to identify one or more genetic variants of interest.

In some embodiments, the system associates the plurality of embeddings with each candidate genetic variant of a plurality of candidate genetic variants to identify a subset of candidate genetic variants that have significant associations with the embeddings. By assessing associations between the candidate genetic variants and embeddings, the system identifies the subset of candidate genetic variants that is associated with histological differences reflected in the images. In some embodiments, the system performs the association test by generating, for each candidate variant, a variant-specific model configured to receive an embedding and output a value of the candidate genetic variant. The variant-specific model is then evaluated to determine whether there is a significant association between each candidate genetic variant and the embeddings (e.g., based on a P value associated with the variant-specific model). The system can generate variant-specific models (e.g., 100,000 models, 1 million models, 10 million models) for all candidate genetic variants (e.g., 100,000 variants, 1 million variants, 10 million variants) to identify the subset of candidate genetic variants. The system can further associate each candidate genetic variant in the subset with the disease of interest to identify at least one genetic variant of interest. In some embodiments, the system generates, for a candidate genetic variant in the subset, a variant-specific score prediction model configured to receive a value indicative of the candidate genetic variant and output a medical diagnosis score related to the disease of interest (e.g., based on the continuous scores described above). The model is then evaluated to determine whether there is a significant association between the candidate genetic variant and the disease of interest.

Other association testing procedures can be implemented in the second stage. In some embodiments, the association testing procedure can be based on a univariate linear model for which the outputs are embeddings and the inputs are covariates, a multivariate linear model for which the outputs are embeddings and the inputs are covariates, or a linear model for which the outputs are covariates and the inputs are embeddings. The association testing procedure can be also based on extensions of linear models such as linear mixed models or logistic regression or on nonlinear models (e.g., random forest, SVMs, etc.). The application of the association testing procedure can provide a P value of association between each embedding dimension and every tested covariate or between all embedding dimensions as a whole and every tested covariate. Statistically significant association determined through multiple hypothesis testing procedures (such as Bonferroni or Benjamini Hochberg) can provide factors that are associated with variation in the high content phenotypic dataset (e.g., the medical imaging data).

In the third stage, the system can visualize or facilitate visualization of images for describing the histological effects of an identified covariant of interest, such as an identified generic of interest. In some embodiments, the system uses a linear model to identify biopsy image tiles that are predictive of measured endpoints. Multiple embeddings can be generated via linear interpolation to represent a progression of the disease of interest. The embeddings can be transformed into a series of images representing a phenotypic state of a disease. The series of images can be displayed as an animation to provide a visualization of the associated histological changes, which cannot otherwise be detected by an association study of the pathologist score. The visualizations can help with interpretation of the features used by the model and generation of hypotheses based on the histological changes. Accordingly, the system can discover variants that are not associated with disease labels in the second stage and characterize their effects through novel visualization tools in the third stage.

In some embodiments, predicted images in the form of simulated images are generated by a generator component of a trained generative adversarial network (GAN) model. The generator can generate simulated images conditioned on embeddings (e.g., image tile embeddings), enabling interpolation along a phenotype while holding other features constant. For example, the generator can be configured to receive an embedding x (as the condition) and a noise vector u sampled from a standard normal distribution and output a simulated image. In one exemplary implementation, the embedding x is a 2048-dimensional embedding and the noise vector u is a 512-dimensional vector sampled from a standard normal distribution.

In some embodiments, predicted images may be selected from among actual medical images ranked based on each image's predicted score and/or predicted features generated in connection with such image's embedding. The images that are visualized may be some or all of the ranked images. For example, a top N images from the ranking may be displayed. As another example, a top N and a bottom M images from the ranking may be displayed. Alternative subsets of images may be selected based on the ranking.

The embodiments described herein are merely exemplary and the discovery platform can be applied to discover associations between any phenotype of interest and a covariate. In some examples described herein, the phenotypic data comprises medical images; the phenotype of interest is a disease of interest (e.g., NASH), which can be represented by a medical diagnosis score (e.g., fibrosis score); the covariate of interest is a genetic variant of interest. However, it should be understood that the techniques described herein can be applied to discover associations between another phenotype of interest and another covariate. Exemplary phenotypic data include, but are not limited to, which is not to suggest that other listings are limiting, in vivo medical images (e.g., MRI, X-ray, CT scan), medical images generated from biopsy samples, such as histopathology data (e.g., H&E stained, Trichrome), clinical biomarker data (e.g., blood test measurements, including proteomic and cfDNA, cognitive/psychiatric assessment scores, microbiome assessment, etc.) and genomic biomarker data (e.g., bulk RNA-seq, methylation data, genomic sequence data, epigenetic sequence data, etc.). Exemplary phenotypes include, but are not limited to, which is not to suggest that other listings are limiting, a disease of interest, gene expression, metabolomics, proteomics, transcriptomics, or lipidomics, etc. Exemplary covariates include, but are not limited to, which is not to suggest that other listings are limiting, demographic information (e.g., age, sex), clinical covariates (e.g., a disease state, a clinical score or a blood biomarkers), genomic data (e.g., genetic data, expression data, methylation data, etc.), etc.

In some embodiments, the identified relationship can be used to identify biomarkers or targets for disease intervention. For example, certain genetic variants identified as having a causal relationship with disease onset or progression can be further evaluated for their amenability to therapeutic intervention. Additionally, in view of the functional impact of the genetic variant on the disease of interest, additional biological targets may be identified for therapeutic intervention. Such biological targets, may, for instance, be proteins transcribed by the gene in which the genetic variant of interest is located. Such biological targets may also comprise other genes, proteins, or metabolites anticipated to alter, offset, mitigate, supplement or complement the functional impact of the at least one genetic variant on the disease of interest. In some embodiments, the identified relationship can be used to develop a treatment. For example, the impact of candidate therapies previously administered to a group of subjects having the associated genetic variant can be taken into account in developing candidate therapy modifications or analogs. Both longitudinal and cross sectional data regarding the effects of such previously administered candidate therapies can be compared to a predicted state or progression of a disease of interest to determine, quantitatively, the extent to which a genetic variant of interest affects the impact of previously administered candidate therapy on a state or progression of the disease of interest. Such candidate therapy modifications or analogs may be selected to have an enhanced therapeutic effect or reduced adverse side effects in view of the impact of the genetic variant vis-à-vis the disease and that group of subjects. Additionally, disease models reflecting the genetic variant can be used for screening therapeutic candidates. For example, in the case of association with genomic features, statistically significant associations can lead to discovery of new candidate drug targets or key pathways implicated with human disease. Similarly, the impact of candidate therapies previously administered to a group of subjects having the associated genetic variants, including adverse impact on the disease state or side effects, can be used to develop combination therapies. Thus, techniques described herein can be used for predicting likely responses to therapeutic candidates among subjects with different genetic backgrounds, identifying suitable patient cohorts to receive a particular therapy, and generally designing clinical trials to optimize outcomes.

The discovery platform can be used to selectively administer, adjust, or apply a treatment. In some embodiments, the identified relationship can be used to provide a medical recommendation. The medical recommendation may include a recommendation of a treatment and/or therapy of a patient, and/or an instruction to contact a medical professional for assistance. In some embodiments, a report can be generated based on the identified relationship. In case of association with demographic and clinical features, significant associations can lead to the discovery of new associations (e.g., associations with sex, age, cholesterol levels) and/or detect technical biases in the datasets (e.g., associations with a particular clinical center).

In some embodiments, the identified relationship can be used to identify a biological target (e.g., drug target) for treating the disease of interest. Once the genetic variant is identified to be associated with a particular disease, the genetic variant may serve as a target (e.g., drug target) for treating said disease. In some embodiments, the genetic variant that is correlated with the disease is studied to further understand gene function, disease pathology (e.g., genotype/phenotype correlation), and/or assess the potential for therapeutic targeting of the genetic variant for treatment of the disease in a patient. For example, a genetic variant may be a loss-of-function variant that confers disease pathology due to the absence of expression of the gene comprising the genetic variant. In some embodiments, drug screening is conducted to evaluate the effect of various drugs on the disease phenotype correlated with the genetic variant genotype. In some embodiments, the drug for disease treatment is selected based on alleviation of the disease phenotype following treatment with said drug. In some embodiments, the genetic variant is correlated with NASH disease. In some embodiments, the genetic variant correlated with NASH disease is a drug target for the treatment of NASH disease. While a biological target may be an associated genetic variant itself, targets can also comprise (a) a protein or metabolite transcribed by the gene containing the variant, (b) a protein or metabolite that can offset/supplement a deficit caused by the variant, (c) a gene, protein or metabolite that is an inverse agonist of the variant and its functional impact, etc.

The following description sets forth exemplary methods, parameters, and the like. It should be recognized, however, that such description is not intended as a limitation on the scope of the present disclosure but is instead provided as a description of exemplary embodiments.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1 illustrates an architecture 100 of an exemplary discovery platform, in accordance with some embodiments. At Stage 1, an exemplary system (e.g., one or more electronic devices) generates embeddings based on medical imaging data related to a phenotype of interest such as a disease of interest. An embedding is a vector representation of a phenotypic state relative to the disease of interest reflected in the medical imaging data. The embedding captures rich semantic information of the medical imaging data (e.g., features of the microscopic structure of tissues reflected in the image), while excluding information that is not relevant to the downstream analysis (e.g., orientation of the image). As shown in FIG. 1, four medical images 102a, 102b, 102c, and 102d can be transformed into four embeddings, which are depicted as four points 104a, 104b, 104c, and 104d, respectively, in an embedding space 106, which is also referred to herein interchangeably as a latent space 106. In the depicted example, the disease of interest is non-alcoholic steatohepatitis (NASH) and the medical images are from H&E stained liver biopsies from a number of clinical trials. The resulting unsupervised embeddings can enable target identification, cross-clinical trial analysis, and enhance interpretability, as described herein.

In some embodiments, the system generates an embedding (e.g., embeddings represented by points 104a-104d) by inputting medical imaging data into a trained unsupervised machine-learning model, such as a contrastive learning algorithm. Contrastive learning models can extract embeddings from imaging data that are linearly predictive of biological endpoints or labels (e.g., progression of the disease of interest) that may otherwise be assigned to such data, as described herein. A suitable contrastive learning model is trained such that it can maximize the similarity between embeddings from different augmentations of the same sample image and minimize the similarity between embeddings of different sample images. For example, the model can extract embeddings from images that are invariant to rotation, flipping, cropping, color jittering, or other image augmentations, or combinations thereof.

In some embodiments, the embeddings can be mean-aggregated and/or normalized before being used for downstream analysis (e.g., Stage 2). In some embodiments, normalizing the embeddings comprises performing a variance-stabilizing transformation, which allows for the application of simple regression-based analysis downstream. As described herein, normalization can improve the performance of linear predictive models fit based on the embeddings. In some embodiments, a linear model fit with normalized embeddings has similar or superior predictive capability as a supervised machine-learning model and is more computationally efficient to generate and apply, as described further herein.

In some embodiments, predictive images can be identified for determining a covariate of interest. In some embodiments, predictive features may be generated at the tile-level in histopathology data. This may be accomplished using various techniques. For example, a mean aggregate tile embedding may be obtained to generate biopsy embeddings. A linear model may be fit using this data such that covariates can be predicted from biopsy embeddings. A linear model may also be applied to the tile embeddings to generate tile-level scores. As another example, multiple instances of a machine learning model may be fit directly on tile embeddings. For instance, a model may be fit that predicts both a score and a weight for each tile and then performs a weighted average of the scores. Both the score and the weight(s) may be considered as two-dimensional predictive features.

In some embodiments, predictive images may be identified based on predictive features associated with those images. For example, tiles with a highest or lowest predicted score may be analyzed to identify predictive images. As another example, a condition of interest may be defined (e.g., high fibrosis score versus a low fibrosis score, a first genetic sequence versus a second genetic sequence, and the like). Models of the probability of a given tile's features with respect to a first condition of interest (e.g., P(tile features|condition 1)) and the probability of a given tile's features with respect to a second condition (e.g., P(tile features|condition 2)) may be fit. The tile images can then be visualized (e.g., rendered on a user interface). In some embodiments, P(tile features|condition 1)/P(tile features|condition 2) may represent a probability of observing a tile with the given features is more likely under condition 1 or condition 2 (or other conditions if defined). The ratio may be sufficiently large or small indicating the likelihood of condition 1 or condition 2 being more likely. In some embodiments, tiles with low predicted probability may be filtered to ignore outliers.

At Stage 2, the system (e.g., one or more electronic devices that are the same or similar to the one or more electronic devices used at Stage 1) may perform a statistical analysis of the embeddings, for example, using one or more linear regression models. Performing statistical analysis using embeddings rather than imaging data provides a number of technical advantages. First, an embedding captures rich semantic information of the imaging data (e.g., features of the microscopic structure of tissues reflected in the image), while excluding information that is not relevant to the downstream analysis (e.g., orientation of the image). Further, the embedding is of a significantly smaller size than the imaging data it represents. In an exemplary implementation, the embedding can be a 2048-dimensional vector, while the corresponding medical image comprises data corresponding to a large number of pixels (e.g., tens of thousands of pixels, hundreds of thousands of pixels, millions of pixels). Therefore, storing the embeddings can conserve memory while also decreasing processing time to perform the analysis as compared to using the medical image data.

Further still, the embeddings may allow the system to generate (e.g., fit) linear regression models that are configured to receive embeddings as the input and output a variety of useful predictions. In some embodiments, the linear regression models are linear mixed models, which provide a flexible framework for statistical analysis of embeddings of phenotypic variation, including treatments and potential covariate effects. As described herein, linear models generated based on embeddings can provide similar or superior predictive power as supervised machine-learning models (e.g., a neural network configured to receive image data) and are more computationally efficient to train and to apply than supervised machine-learning models.

In some embodiments, Stage 2 comprises using the embeddings to obtain fine-grained labels for medical images 102a-102d, such as continuous scores indicative of the disease of interest. For example, a linear model can be generated (e.g., fit) based on embeddings and pathologist-assigned, discrete medical diagnosis scores associated with the embeddings. The model can then be applied to the embeddings to predict continuous medical diagnosis scores.

In many cases, a predicted continuous score has strong advantages over a discrete score assigned by a pathologist. Specifically, the predicted score has a continuous value and thus captures more nuance than a pathologist-assigned, discrete, score. The ability to assign continuous scores to the embeddings (and image data) results in higher precision and improved statistical power in downstream analyses, such as obtaining a closer association of each depicted disease state with a genetic variant or variants. For example, the severity of NASH and liver fibrosis is currently histologically assessed by pathologists through the NASH CRN and Ishak stage ordinal scores, such as the Ishak fibrosis score (integers 0-6), the steatosis score (integers 0-3), the lobular inflammation score (integers 0-3), and the ballooning score (integers 0-2). Quantitative analyses of these metrics are challenged by their low-resolution categorization of disease. On the other hand, the linear model can be trained to generate continuous scores from imaging data (e.g., H&E liver biopsy imaging data) that are predictive of pathologist scores. The continuous scores enable a more precise definition of disease progression, empowering longitudinal expression analysis and genetic association studies.

In some embodiments, Stage 2 includes blocks 110-160. Each block is a functional representation of the functionality performed by one or more computing systems. In some embodiments, a same computing system or systems may effectuate the operations of two or more blocks. For example, Stage 2 comprises block 110. In block 110, the system (e.g., one or more computing systems) may be configured to perform association testing between a candidate genetic variant and the disease of interest. The association testing comprises generating (e.g., fitting) a linear model based on the candidate genetic variant and the continuous scores indicative of the disease of interest. The system can generate variant-specific models (e.g., 100,000 models, 1 million models, 10 million models) for all candidate genetic variants of interest (e.g., 100,000 variants, 1 million variants, 10 million variants). Each model can be evaluated to determine if there is a significant association between each candidate genetic variant and the disease of interest. Details of block 110 are provided herein with reference to FIG. 2.

In some embodiments, Stage 2 comprises a block 120. In block 120, the system may be configured to associate the plurality of embeddings with each candidate genetic variant of a plurality of candidate genetic variants to identify a subset of candidate genetic variants that have significant associations with the embeddings. By assessing associations between the candidate genetic variants and embeddings, the system can identify the subset of candidate genetic variants that are associated with histological differences (if any) reflected in the images. The techniques described herein can identify variants that affect histology that would not be discovered by focusing the analysis on specific diagnostic scores.

In some embodiments, the system performs the association test by generating, for each candidate variant, a variant-specific model configured to receive an embedding and output a value of the candidate genetic variant. The variant-specific model is then evaluated to determine whether there is a significant association between each candidate genetic variant and the embeddings (e.g., based on a P value associated with the variant-specific model). The system can generate variant-specific models (e.g., 100,000 models, 1 million models, 10 million models) for all candidate genetic variants (e.g., 100,000 variants, 1 million variants, 10 million variants).

In block 120, the system can further associate each candidate genetic variant in the subset with the disease of interest to identify at least one genetic variant of interest from the subset. In some embodiments, the system generates, for a candidate genetic variant in the subset, a variant-specific score prediction model configured to receive a value indicative of the candidate genetic variant and output a medical diagnosis score related to the disease of interest (e.g., based on the continuous scores described above). The model may then be evaluated to determine whether there is a significant association between the candidate genetic variant and the disease of interest. Details of block 120 are provided herein with reference to FIG. 7.

In block 130, the system can further evaluate a treatment with respect to a progression of a disease of interest. The progression of the disease can be quantified using progression embeddings as described herein. The system may be configured to impute drug response phenotype (DRP) as the predictions from a model that receives input progression embeddings and output a classification result indicating placebo or the treatment. The system can determine if there is a significant association between the DRP and the treatment. If there is a significant association, the treatment can be further analyzed in downstream analyses (e.g., block 140). Details of block 130 are provided herein with reference to FIG. 16.

In block 140, the system may be further configured to identify a covariant of interest with respect to the DRP associated with a treatment. The imputation of DRP can be performed using clinical trial datasets as long as the progression embeddings are available. Significant associations between DRP and molecular data (e.g., expression and genetics) can be retrieved through an association test. Association with expression identifies genes that could not be detected in a placebo-vs-drug differential expression analysis. In some cases, the analysis of the DRP can identify a correlated set of genes as case control of the true placebo-vs-drug differential expression analysis. In some cases, the analysis of DRP can identify a larger set of genes due to the analysis of a larger cohort, which can help interpret correlates of the DRP.

Figure 28:
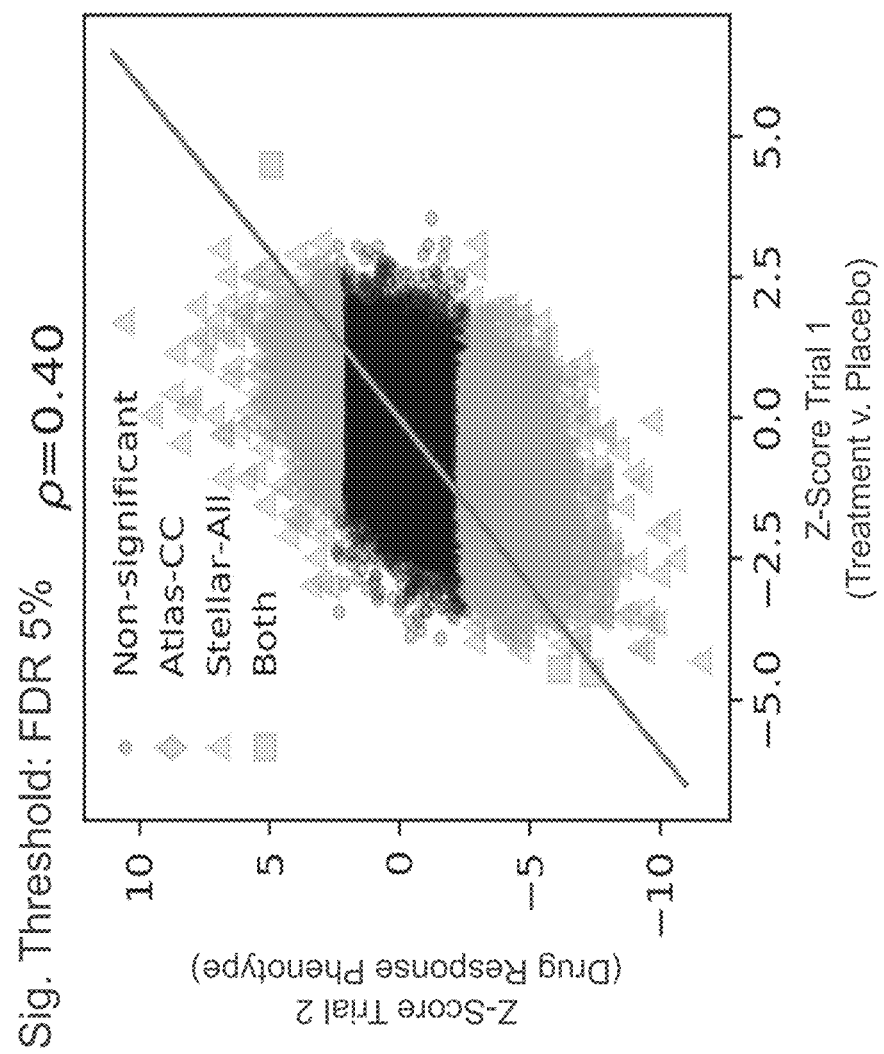
FIG. 28 illustrates a comparison of z-scores, in accordance with some embodiments.

In some embodiments, a comparison of z-scores of the analysis of treatment vs placebo in small trials versus the analysis of imputed DRP in larger trials may be used to identify the correlation, as seen, for example, with respect to FIG. 28. Details of block 140 are provided herein with reference to FIG. 20.

Figure 26:
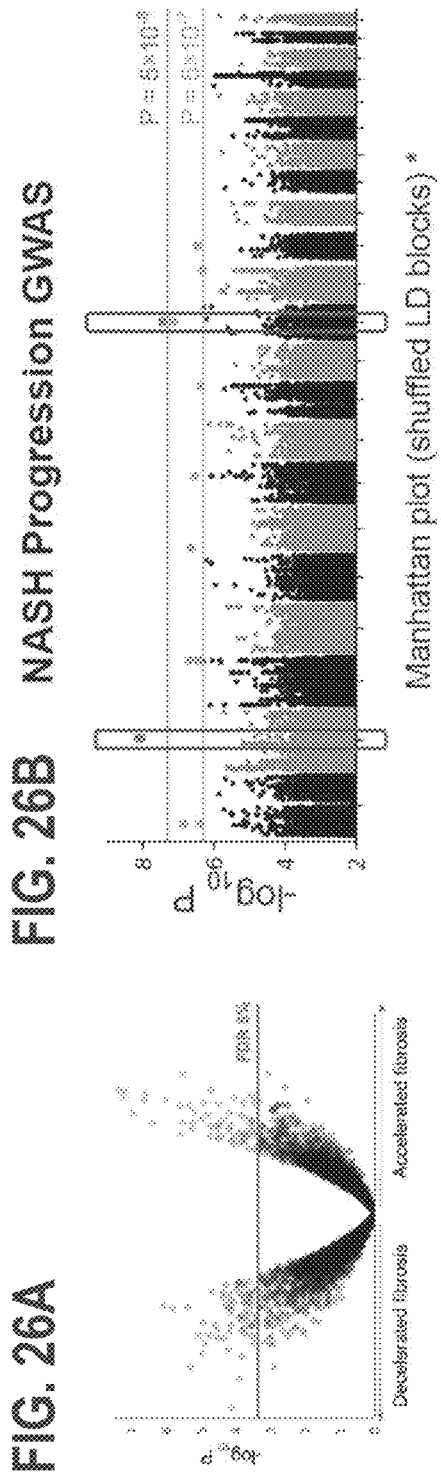
FIG. 26A illustrates an exemplary longitudinal expression analysis, in accordance with some embodiments.
FIG. 26B illustrates exemplary genetic association studies, in accordance with some embodiments.

In block 150, the system may further be configured to evaluate a treatment with respect to progression of a disease of interest. The disease progression can be quantified by continuous medical diagnosis scores. Significant associations between high resolution NASH scores and various treatments are retrieved through an association test. This process can retrieve drug effects on medical diagnosis scores that could not be detected using pathologist-assigned, discrete scores. The continuous scores enable a more precise definition of disease progression, empowering longitudinal expression analysis (e.g., FIG. 26A) and genetic association studies (e.g., FIG. 26B). Details of block 150 are provided herein with reference to FIG. 22.

In block 160, the system can be further configured to identify a patient subgroup of interest. The system can obtain embeddings from patient image data and identify clusters of embeddings to identify subgroups of patients. Significant associations between each patient cluster identity and disease biomarkers, genetic variants, and expression levels are retrieved from an association test. This procedure retrieves patient segments and associated clinical labels and molecular drivers. Details of block 160 are provided herein with reference to FIG. 24.

Other association testing procedures can be implemented in Stage 2. In some embodiments, the association testing procedure can be based on a univariate linear model for which the outputs are embeddings and inputs are covariates, a multivariate linear model for which the outputs are embeddings and inputs are covariates, a linear model for which the outputs are covariates and inputs are embeddings. The association testing procedure can be also based on extensions of linear models such as linear mixed models or logistic regression or on nonlinear models (random forest, SVMs, etc.). The application of the association testing procedure can provide a P value of association between each embedding dimension and every tested covariate or between all embedding dimensions as a whole and every tested covariate. Statistically significant associations determined through multiple hypothesis testing procedures (such as Bonferroni or Benjamini Hochberg) can provide factors that are associated with variation in the high content phenotypic dataset (e.g., the medical imaging data).

In an optional Stage 3, the system can be configured to generate simulated images, such as simulated image 172, to visualize the histological effects of an identified covariant of interest, such as an identified generic of interest. As shown in FIG. 1, an embedding in the latent space can be generated and then transformed into an image to visualize the phenotypic state relative to the disease of interest. In some embodiments, the system uses a linear model to identify biopsy image tiles that are predictive of measured endpoints. Multiple embeddings can be generated via linear interpolation to represent a progression of the disease of interest. The embeddings can be transformed into a series of images. The series of images can be displayed as an animation to provide a visualization of the associated histological changes, which cannot otherwise be detected by an association study of the pathologist score. In an exemplary implementation, the procedure takes as input a discovered genetic variant of interest in Stage 2, biopsy embeddings (matrix with analyzed biopsies as rows and embedding dimension as columns), and tile embeddings (matrix with the corresponding tiles as rows and embedding dimension as columns), and outputs a series of n 256×256 tile image. The visualizations can help with interpretation of the features used by the model and generation of hypotheses based on the histological changes. Accordingly, the system can discover variants that are not associated with disease labels in Step 2 and characterize their effects through novel visualization tools in Step 3.

In some embodiments, the simulated images are generated by a generator component of a trained generative adversarial network (GAN) model. The generator can generate images conditioned on embeddings (e.g., image tile embeddings), enabling interpolation along a phenotype while holding other features constant. For example, the generator can be configured to receive an embedding x (as the condition) and a noise vector u sampled from a standard normal distribution and output a simulated image. In one exemplary implementation, the embedding x is a 2048-dimensional embedding and the noise vector u is a 512-dimensional vector sampled from a standard normal distribution.

In some embodiments, the simulated images may be ranked. The ranking of the simulated images may be used as a basis for which simulated images are to be presented and/or stored for further analysis. In some embodiments, the simulated images may be ranked based on medical diagnosis score.

The embodiments described herein are merely exemplary and the discovery platform can be applied to discover associations between any phenotype of interest and a covariate. In some examples described herein, the phenotypic data comprises medical images; the phenotype of interest is a disease of interest (e.g., NASH), which can be represented by a medical diagnosis score (e.g., fibrosis score); the covariate of interest is a genetic variant of interest. However, it should be understood that the techniques described herein can be applied to discover associations between another phenotype of interest and another covariate. Exemplary phenotypic data include medical images (e.g., MRI, X-ray, CT scan), histopathology data (e.g., H&E stained, Trichrome), clinical biomarker data (e.g., blood test measurements, including proteomic and cfDNA, cognitive/psychiatric assessment scores, microbiome assessment, etc.) and genomic biomarker data (e.g., bulk RNA-seq, methylation data, genomic sequence data, epigenetic sequence data, etc.). Exemplary phenotypes include: a disease of interest, gene expression, metabolomics, proteomics, transcriptomics, lipidomics, etc. Exemplary covariate classes include: demographic information (e.g., age, sex), clinical covariates (e.g., disease state, a clinical score or a blood biomarkers), genomic data (e.g., genetic data, expression data, methylation data, etc.), etc.

FIG. 2 illustrates an example process 200 for identifying a genetic variant of interest with respect to a disease of interest, according to various examples. Process 200 is performed, for example, using one or more electronic devices implementing a software platform. In some examples, process 200 is performed using a client-server system, and the steps of process 200 are divided up in any manner between the server and one or more client devices. Thus, while portions of process 200 are described herein as being performed by particular devices of a client-server system, it will be appreciated that process 200 is not so limited. In other examples, process 200 is performed using only a client device or only multiple client devices. In process 200, some blocks are, optionally, combined, the order of some blocks is, optionally, changed, and some blocks are, optionally, omitted. In some examples, additional steps may be performed in combination with the process 200. Accordingly, the operations as illustrated (and described in greater detail below) are exemplary by nature and, as such, should not be viewed as limiting.

With reference to FIG. 2, an exemplary system (e.g., one or more electronic devices) can obtain a plurality of medical images obtained from a group of clinical subjects. The medical images depict a state of a disease of interest. In some embodiments, the plurality of medical images comprises a plurality of biopsy images of biopsy samples from the group of clinical subjects. For example, in a biopsy, one or more tissue slides can be obtained from a subject, and one or more digital images can be taken to capture each tissue slide.

Figure 3A:
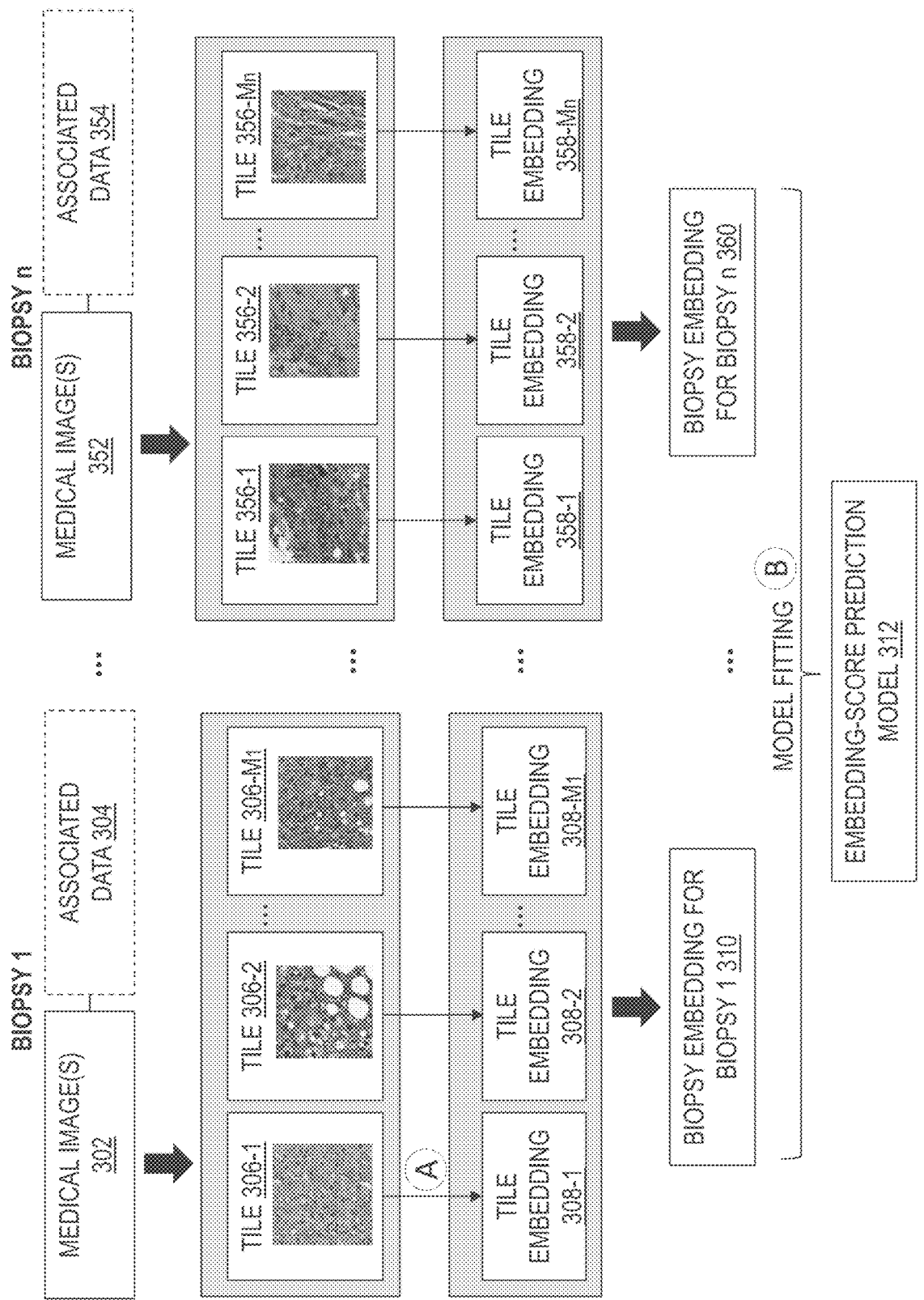
FIGS. 3A and 3B illustrate an exemplary workflow for identifying a genetic variant of interest with respect to a disease of interest, in accordance with some embodiments.

In an exemplary workflow depicted in FIG. 3A, biopsies 1-n have been performed. Biopsies 1-n may correspond to multiple subjects (e.g., cancer patients) and/or multiple visits (e.g., screening visit, follow-up visit). In the depicted example, the disease of interest is non-alcoholic steatohepatitis (NASH) and the biopsies are H&E stained liver biopsies from a number of clinical trials (however similar workflows may be implemented for other dieses of interest). Each biopsy (e.g., biopsy 1) results in one or more biopsy images (e.g., medical image(s) 302 for biopsy 1). Thus, biopsy 1-n result in a plurality of medical images including medical image(s) 302, medical image(s) 352, etc.

The medical images can be associated with various data. For example, with reference to FIG. 3A, associated data 304 is associated with biopsy 1, data 354 is associated with biopsy n, etc. As described below, the data may include known information about the disease of interest and the subject, including information related to the genetic variant of interest.

In some embodiments, the data associated with a medical image can include an assigned medical diagnosis score related to the disease of interest. The assigned medical diagnosis score can indicate the state of a disease. In some embodiments, a medical diagnosis score can be a biopsy-level score assigned by one or more pathologists based on their review of the biopsy slides. For example, for the NASH disease, the severity of NASH, and liver fibrosis can be histologically assessed by pathologists through the NASH CRN and Ishak stage ordinal scores. In some embodiments, the assigned medical diagnosis score can be a biopsy-level fibrosis score, such as the Ishak fibrosis score, which is a score having a discrete value 0, 1, 2, 3, 4, 5, or 6 to indicate the extent of fibrosis. In some embodiments, the assigned medical diagnosis score can be a biopsy-level steatosis score, which is a score having a discrete value 0, 1, 2, and 3 to indicate the extent of steatosis. In some embodiments, the assigned medical diagnosis score can be a biopsy-level lobular inflammation score, which is a score having a discrete value 0, 1, and 2 to indicate the extent of lobular inflammation. In some embodiments, the assigned medical diagnosis score can be a biopsy-level ballooning score, which is a score having a discrete value 0, 1, and 2 to indicate the extent of ballooning. Quantitative analyses of these metrics are challenged by their low-resolution categorization of disease. As described below, a linear model can be trained to generate continuous scores from imaging data (e.g., H&E liver biopsy imaging data) that are predictive of pathologist scores. The continuous scores enable a more precise definition of disease progression, empowering longitudinal expression analysis and genetic association studies.

In some embodiments, the data associated with a medical image can include genetic data of the subject from whom the biopsy sample is taken. For example, the data (e.g., associated data 304) can include the subject's genetic information related to a plurality of genetic variants (e.g., 100,000 variants, 1 million variants, 10 million variants). For example, the data can indicate whether the subject has each of the plurality of genetic variants. For example, for a genetic variant with two alleles in the population, the medical image may be associated with a genetic variant value of 0, 1, or 2 depending on if the individual has 0, 1, or 2 copies of the least frequent allele. In some embodiments, the genetic data of the subject may be a polygenic risk score, indicating a likelihood of the subject incurring a disease of interest.

In some embodiments, the data associated with a medical image (e.g., associated data 304, data 354, etc.) can include demographic data of the subject from whom the biopsy sample is taken. The demographic data can include, for example, sex, age, and/or treatment group (e.g., placebo, treatment x, treatment y).

With reference to FIG. 3A, a medical image can be split into a plurality of image tiles. For example, medical image(s) 302 of biopsy 1 can be split to obtain image tiles 306-1, 306-2, . . . , 306-$M_1$; medical image(s) 352 of biopsy n can be split to obtain image tiles 356-1, 356-2, . . . , 356-$M_n$. In some embodiments, image tiles can be extracted from a medical image using a predefined grid and stored as image tiles of a uniform size. In one exemplary implementation, the image tiles are extracted using a predefined grid with tile dimensions 192 m×192 m and the image tiles are saved as images sized 224 pixels×224 pixels.

Turning back to FIG. 2, at block 202, the system may be configured to input the plurality of medical images obtained from the group of clinical subjects into an unsupervised machine-learning model to obtain a plurality of embeddings in a latent space. In some embodiments, the system splits the plurality of medical images into a plurality of image tiles as described above and inputs each image tile into the unsupervised machine-learning model to obtain a corresponding tile embedding. With reference to FIG. 3A, each image tile of image tiles 306-1-306-$M_1$ may be input to the unsupervised machine-learning model to obtain a tile embedding. For example, image tile 306-1 is input into the unsupervised machine-learning model (represented by process A) to obtain a tile embedding 308. Accordingly, for biopsy 1, the system obtains tile embeddings 308-1-308-$M_1$ respectively corresponding to image tiles 306-1-306-$M_1$. Similarly, for biopsy n, the system may obtain tile embeddings 358-1-358-$M_n$ corresponding to image tiles 306-1-306-$M_n$.

In some embodiments, the system selects only a subset of the plurality of image tiles for further processing by the unsupervised machine-learning model. For example, the system can determine the portion of a given image tile that depicts biopsy material and only input the image tile if the portion exceeds a predefined threshold (e.g., >90%). As another example, the system can determine the count of image tiles resulting from a given biopsy, and only input the image tiles if the count exceeds a predefined threshold (e.g., >70 tiles).

Figure 4A:
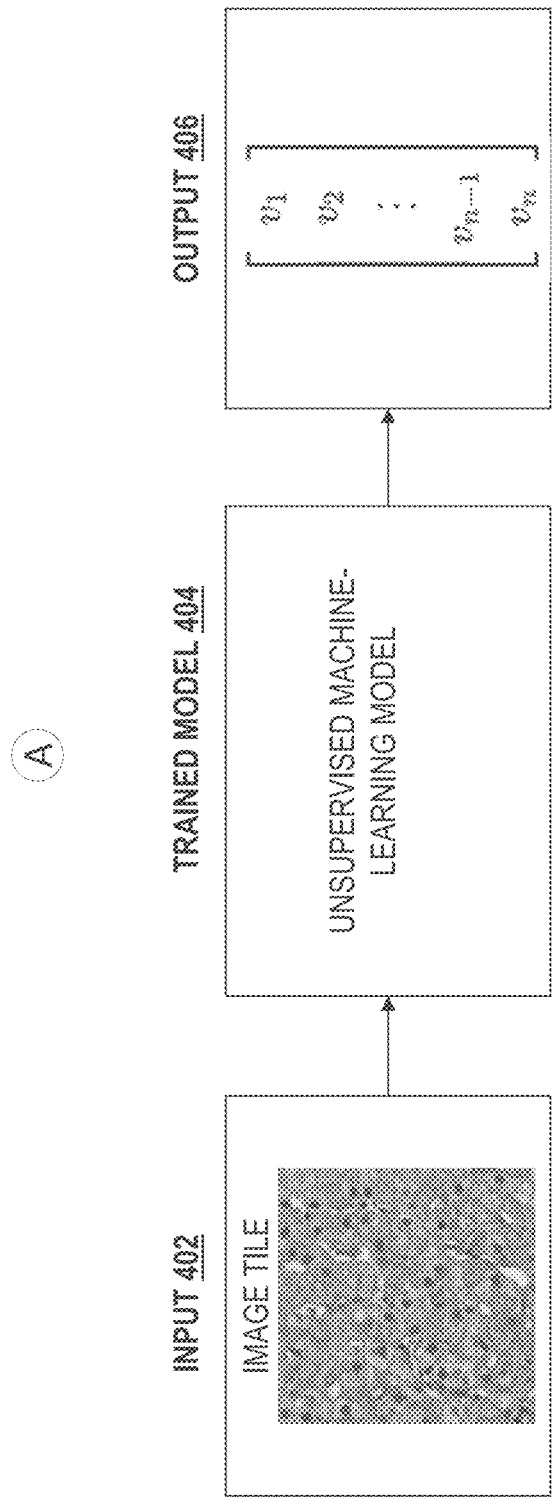
FIG. 4A illustrates an exemplary unsupervised machine-learning model, in accordance with some embodiments.

FIG. 4A illustrates an exemplary unsupervised machine-learning model used in block 202. With reference to FIG. 4A, an unsupervised machine-learning model 404 may be configured to receive an input image tile 402 (e.g., one of the image tiles in FIG. 3A) and provide an output tile embedding 406. Tile embedding 406 can be a vector representation of an input image tile 402 (e.g., tile 306-1) in the latent space. Translating an input image into an embedding can significantly reduce the size and dimension of the original data. As an example, an image tile sized 224 pixels×224 pixels can be reduced to a 2,048-dimensional vector. The lower-dimension embedding can be used for downstream processing 476, as described below.

In some embodiments, unsupervised machine-learning model 404 is a trained contrastive learning algorithm. Contrastive learning can refer to a machine learning technique used to learn the general features of a dataset without labels by teaching the model which data points are similar or different. Contrastive learning models can extract embeddings from imaging data that are linearly predictive of labels that might otherwise be assigned to such data. A suitable contrastive learning model is trained by minimizing a contrastive loss, which maximizes the similarity between embeddings from different augmentations of the same sample image and minimizes the similarity between embeddings of different sample images. For example, the model (e.g., unsupervised machine-learning model 404) can extract tile embeddings from tile images (e.g., input image tile 402) that are invariant to rotation, flipping, cropping, and/or color jittering. Exemplary contrastive learning models include SimCLR and SwAV, but it should be appreciated that any contrastive learning algorithm can be used as unsupervised machine-learning model 404.

Figure 4B:
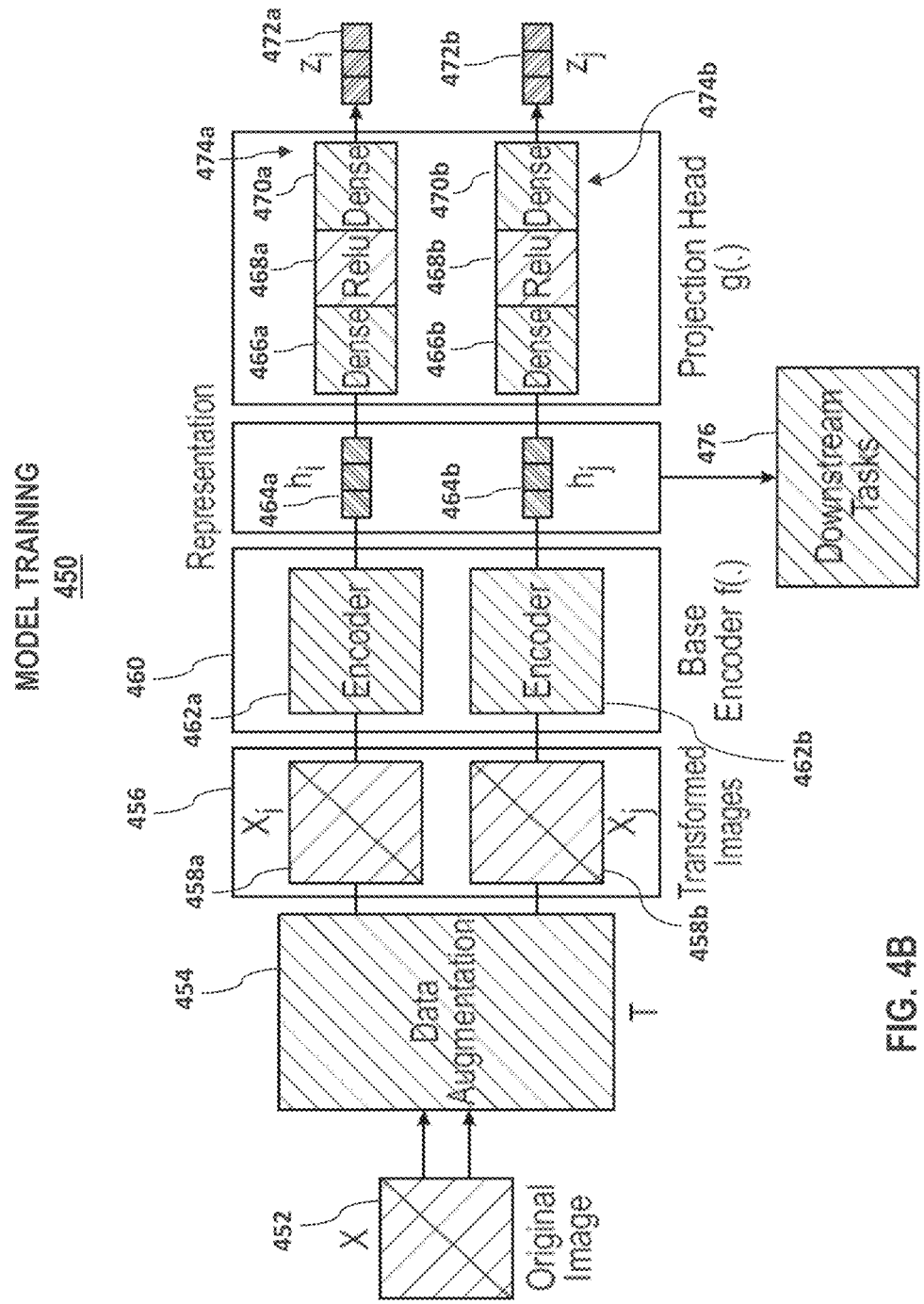
FIG. 4B illustrates a data architecture for training of an exemplary contrastive learning algorithm, in accordance with some embodiments.

Before unsupervised machine-learning model 404 is used to process input images (e.g., input image tile 402), it needs to be trained. FIG. 4B illustrates a data architecture 450 for training of an exemplary contrastive learning algorithm, in accordance with some embodiments. In some embodiments, unsupervised machine-learning model 404 in FIG. 4A can be one of the encoders in FIG. 4B (e.g., encoder 462a, 462b). During training, an original image 452 may be obtained. Data transformations or augmentations 454 can be applied to the original image 452 to obtain, at a viewing stage 456, two augmented images 458a and 458b. For example, the system can randomly apply two separate data augmentation operators (e.g., crop, flip, color jitter, grayscale, blur) to obtain augmented images 458a, 458b. In some embodiments, more than two images may be produced. For example, N data augmentations 454 (which may be similar or different) may be performed to original image 452 to obtain N augmented images.

Data architecture 450 may include an encoding stage 460 within the model training 450 where each augmented image (e.g., augmented images 458a, 458b) may be encoded by a respective one of encoders 462a, 462b. Each of augmented images 458a, 458b may be passed through an encoder to obtain respective vector representations 464a, 464b in a latent space. In some embodiments, encoders 462a and 462b have shared weights. In some embodiments, each encoder 462a, 462b is implemented as a neural network. For example, an encoder can be implemented using a variant of the residual neural network ("ResNet") architecture. As shown, encoders 462a and 462b output vector representation 464a (e.g., hi vector output by encoder 462a based on augmented image 458a) and vector representation 464b (e.g., $h_j$ vector output by encoder 462b based on augmented image 458b), respectively.

Vector representations 464a, 464b may be passed through projection head 474a, 474b, respectively, to obtain two projections 472a, 472b. In some embodiments, projection head 474a, 474b comprises a series of non-linear layers (e.g., Dense-Reu-Dense layers) to apply non-linear transformation on the vector representation to obtain the projection. For example, projection head 474a may include a dense layer 466a, a ReLu layer 468a, and a dense layer 470a, and projection head 474b may include a dense layer 466b, a ReLu layer 468b, and a dense layer 470b. Each of projection heads 474a, 474b may be configured to amplify the invariant features and maximizes the ability of the network to identify different transformations of the same image.

During training, the similarity between projections 472a, 472b for the same input image (e.g., original image 452) may be maximized. For example, a loss is calculated based on projections 472a, 472b, and each encoder 462a, 462b may be updated based on the loss to maximize a similarity between the two latent representations (e.g., representations 464a, 464b). Similarly, the similarity between projections of different input images may be minimized during training. In some examples, to maximize agreement (i.e., similarity) between the projections, the system can define the similarity metric as cosine similarity:

$$sim(u, v) = \frac{u^T v}{\|u\|\|v\|}$$

In some examples, the system trains the network by minimizing the normalized temperature-scaled cross-entropy loss:

$$\ell_{i,j} = -\log \frac{\exp\left(\frac{sim(z_i, z_j)}{\tau}\right)}{\sum_{k=1}^{2N} \mathbb{1}_{[k \neq i]} \exp\left(\frac{sim(z_i, z_j)}{\tau}\right)}$$

where, τ denotes an adjustable temperature parameter, and $z_i$, $z_j$ correspond to projections 472a, 472b, respectively.

Accordingly, via training 450, encoders 462a, 462b of data architecture 450 can be configured to learn to output a vector representation that preserves the invariant features of the input image while minimizing image-specific characteristics (e.g., imaging angle, resolution, artifacts).

Returning to FIG. 2, in some embodiments, unsupervised machine-learning model 404 can be trained using non-medical images and then used to process medical images in block 204. In some embodiments, the model is first trained using non-medical images, then fine-tuned (e.g., retrained) using medical images for a number of epochs, and then used to process input medical images in block 204. In some embodiments, the medical images used to fine-tune unsupervised machine-learning model 404 can be selected from the image tiles from biopsies 1-n. In other words, image tiles 306-1-306-$M_1$, ..., 356-1-356-$M_n$, from biopsies 1-n may be first used to train the model, and then inputted into the trained model to obtain tile embeddings.

Tile embeddings 308-1-308-$M_1$, ..., 358-1-358-$M_n$, can be aggregated on the biopsy level. The aggregation can comprise averaging the tile embeddings across all tiles in a biopsy. With reference to FIG. 3A, tile embeddings 308-1-308-$M_1$ of biopsy 1 can be aggregated to obtain a biopsy embedding 310. Similarly, tile embeddings 358-1-358-$M_n$ of biopsy n can be aggregated to obtain a biopsy embedding 360. Each biopsy embedding corresponds to a phenotypic state relative to the disease of interest reflected in the biopsy. In an exemplary implementation, 6,782 biopsies result in 6,782 biopsy embedding. Each biopsy embedding is a 2048-dimensional vector calculated by averaging multiple 2048-dimensional tile embedding vectors. This data can be represented as a 6,782×2,048 matrix ($X \in R^{N \times L}$, N=6,782 and L=2,048).

In some embodiments, biopsy embeddings 310, 360 are standardized and then rescaled by the inverse of the square root of the number of embedding dimensions before further processing. The normalization can improve the performance of linear predictive models fitted based on the biopsy embeddings, as discussed herein.

At block 204, the system may obtain a plurality of predicted continuous medical diagnosis scores corresponding to the plurality of embeddings using a linear regression model. As described above, each of the embeddings may correspond to a phenotypic state relative to the disease of interest reflected in the image data and captures rich semantic information (e.g., of features of the microscopic structure of tissues) reflected in the image data. An embedding can be used to generate fine-grained disease-related labels for the image data. For example, each embedding can be used by a linear model to predict a continuous medical diagnosis score related to the disease of interest. A predicted continuous score is superior to an assigned score of the biopsy described above with reference to associated data 304 in FIG. 3A. Specifically, the predicted score has a continuous value rather than a discrete value (e.g., a value of 0, 1, 2, 3, 4, 5, and 6 assigned by a pathologist) and captures more nuance than a pathologist-assigned score. The ability to assign continuous scores to the embeddings (and image data) provides higher precision and improved statistical power in downstream analyses, such as obtaining a closer association of each depicted disease state with a genetic variant or variants.

Figure 3B:
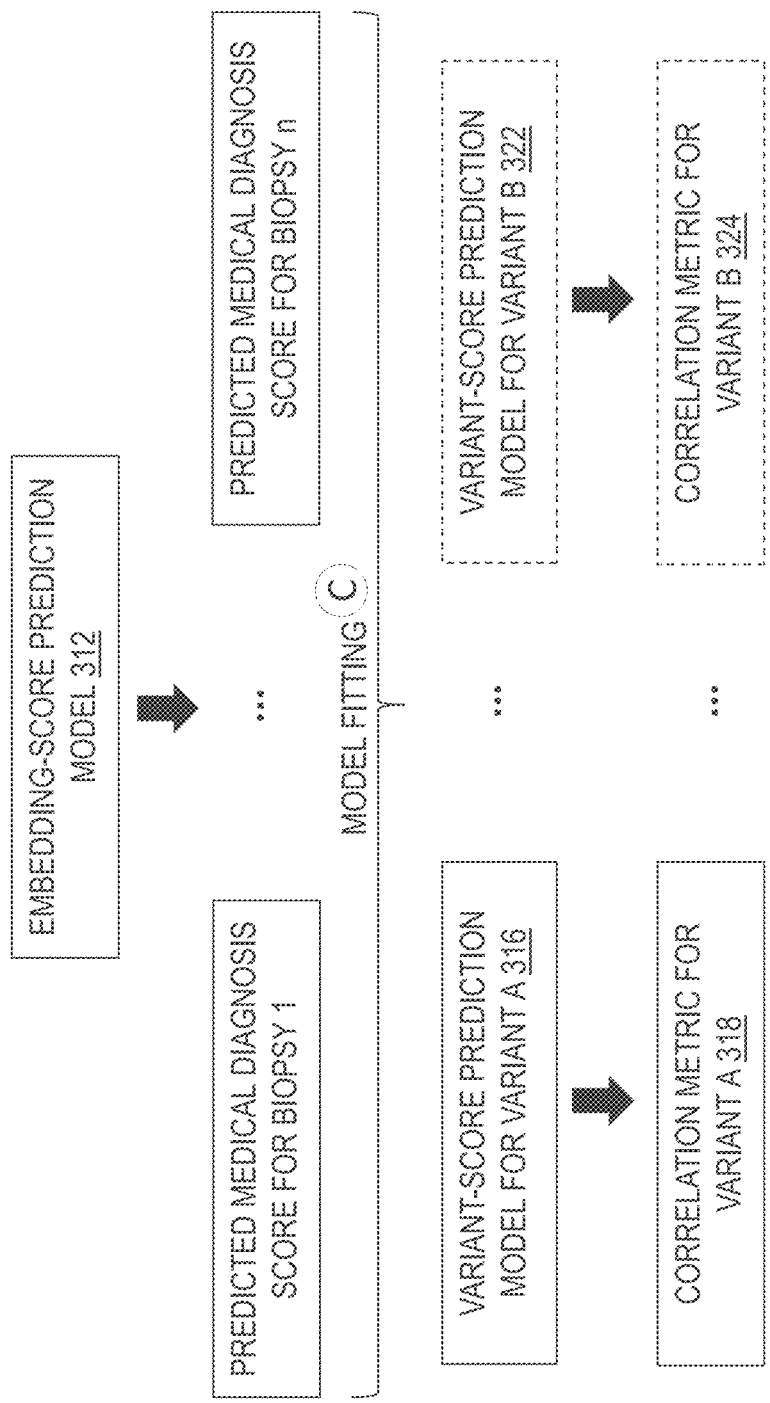

In the depicted example in FIG. 3A and FIG. 3B, the biopsy embeddings for biopsies 1-n may be used to generate (e.g., fit) a linear regression model (i.e., embedding-score prediction model 312), which may then be used to generate predicted medical diagnosis scores for biopsies 1-n.

In some embodiments, the linear regression model (e.g., embedding-score prediction model 312) is configured to receive embeddings as input and output predicted medical diagnosis scores. In some embodiments, the linear regression model can be implemented as a linear mixed model (LMM), which is an extension of simple linear models to allow both fixed and random effects. The linear mixed model allows for performing association testing while accounting for covariates (such as sex, age, and/or clinical trial arm), as shown below.

In some embodiments, the linear regression model can be:

$$y = Fb + u + \psi \text{ where:}$$

$y \in R^{N \times 1}$ represents medical diagnosis scores (e.g., biopsy level fibrosis score) for N individuals.

$F \in R^{N \times K}$ represents a matrix of K covariates (e.g., sex, age, clinical trial arm).

$b \in R^{K \times 1}$ represents a covariate effect size vector. The vector includes various model parameters and are the weights of the covariates in a linear model. Specifically, there are K weights for the K covariates respectively.

$u \sim N(0, \sigma_x^2 XX^T)$ models the contribution from histological embeddings.

$\psi \sim N(0, \sigma_e^2 I_N)$ is residual iid gaussian noise.

$X \in R^{N \times L}$ represents a matrix of biopsy embeddings with dimension L for N individuals (e.g., L=2048).

$I_N \in R^{N \times N}$ represents the N×N identity matrix.

$\sigma_x^2$ and $\sigma_e^2$ are scalar model parameters.

In some embodiments, the system generates parameters for the linear regression model (i.e., fits the model) for predicting medical diagnosis scores. The model can be fit using biopsy data, including biopsy embeddings and the corresponding medical diagnosis scores. In the depicted example in FIG. 3A, the biopsy embeddings for biopsies 1-n are used to fit the embedding-score prediction model 312.

Figure 5:
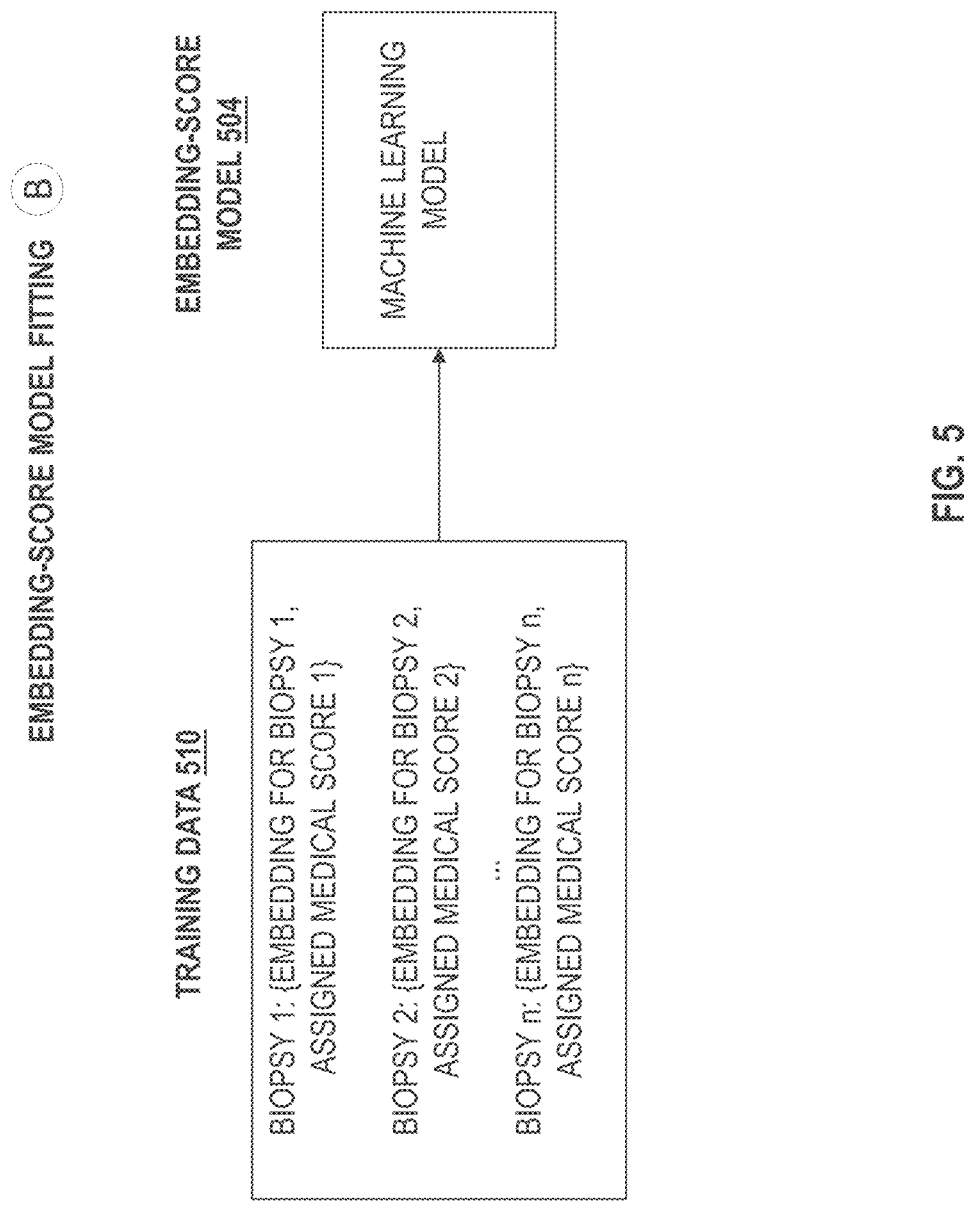
FIG. 5 illustrates fitting of an exemplary linear regression model for predicting medical diagnosis scores, in accordance with some embodiments.

FIG. 5 illustrates fitting of an exemplary machine learning model (e.g., embedding-score prediction model 312) for predicting medical diagnosis scores. In some embodiments, the machine learning model may be a linear regression model. As shown, embedding-score prediction model 504 may be fit using training data 510. Training data 510 may comprise data of biopsies 1-n, including the biopsy embeddings (e.g., biopsy embedding 310) and the corresponding biopsy-level assigned medical scores. For example, the embeddings are biopsy embeddings for biopsies 1-n described with reference to FIG. 3A, and the medical diagnosis scores are assigned fibrosis scores for biopsies 1-n (e.g., stored as part of associated data 304, 354 in FIG. 3A).

In an exemplary implementation, 6,782 biopsies result in 6,782 biopsy embeddings. Each biopsy embedding may be a 2048-dimensional vector calculated by averaging multiple 2048-dimensional tile embedding vectors. This data can be represented as a 6,782×2,048 matrix ($X \in R^{N \times L}$, N=6,782 and L=2,048). The matrix is used as the input matrix X to fit a machine learning model (e.g., linear regression model). The covariate matrix $F \in R^{N \times K}$ contains an intercept (i.e., a single column (K=1) with all ones).

The negative log marginal likelihood of the machine learning model can be:

$$f(b, \sigma_x^2, \sigma_e^2) = -\log N(y; Fb, \sigma_x^2 XX^T + \sigma_e^2 I_N), \text{ with} \\ \text{parameters } b, \sigma_x^2 \text{ and } \sigma_e^2.$$

Maximum likelihood estimators (MLE) of b, $\sigma_x^2$, $\sigma_e^2$ can be obtained by minimizing $f(b, \sigma_x^2, \sigma_e^2)$ using a similar efficient procedure. In some embodiments, this can be achieved by (i) rotating the data in a space where the covariance is diagonal, such as $f(b, \sigma_x^2, \sigma_e^2) = -\log N(U^T y;$ $U^T$Fb, $\sigma_x^2 S + \sigma_e^2 I_N$) (where the eigenvalue decomposition of $XX^T$ is indicated as $USU^T$), and (ii) reparameterizing the model as f(b, $\sigma^2$, $\delta$)=-log $N(U^T y; U^T$ Fb, $\sigma^2 \delta S + \sigma^2(1-\delta)I_N)$. In the new form, optimization can proceed by performing a grid search on delta $\delta$ with closed form solutions for MLEs of b, $\sigma^2$ for each value of delta $\delta$. This optimization is also computationally efficient. After optimization, the MLEs of $\sigma_x^2$ and $\sigma_e^2$ can be computed as $\hat{\sigma}_x^2 = \hat{\sigma}^2 \hat{\delta}$ and $\hat{\sigma}^2 = \hat{\sigma}^2(1-\hat{\delta})$ respectively from the MLEs $\hat{\delta}$ and $\hat{\sigma}^2$.

After the machine learning regression model (e.g., embedding-score prediction model 312, 504) is fit, the predicted continuous medical diagnosis scores can be obtained. In some embodiments, the predicted continuous medical diagnosis scores can be obtained as leave-one-out predictions using biopsy embeddings. Leave-one-out (LOO) prediction uses an entire model fit to all the data except a single point, and then makes a prediction at that point. The LOO approach is computationally inexpensive and can bias the predictions to better results. For example, leave-one-out prediction $\hat{y}_i$ for predicted score y can be obtained from the fitted LMM as:

$$\hat{y}_i = \frac{H_{i,:}\tilde{y} - H_{ii}\tilde{y}}{1 - H_{ii}}$$

where $\tilde{y} = y - F\hat{b}$, $H = \hat{\sigma}_x^2 XX^T(\hat{\sigma}_x^2 XX^T + \hat{\sigma}_e^2 I_N)^{-1}$, and $\hat{b}$, $\hat{\sigma}_x^2$ and $\hat{\sigma}_e^2$ are MLE of $b$, $\sigma_x^2$ and $\sigma_e^2$.

Thus, the system obtains predicted medical diagnosis scores $\tilde{y} \in R^{N \times 1}$ predicted from the biopsy embeddings (e.g., biopsy embeddings 310, 360).

With reference to FIG. 3B, embedding-score prediction model 312 can be used to generate predicted scores for biopsies 1-n. For example, the medical diagnosis score can be a biopsy-level fibrosis score. The predicted score of a biopsy is different from an assigned score of the biopsy described above with reference to associated data 304 in FIG. 3A. Specifically, the predicted score has a continuous value rather than a discrete value (e.g., a value of 0, 1, 2, 3, 4, 5, and 6 assigned by a pathologist) and thus provides higher precision and improved statistical power in downstream analyses.

Turning back to FIG. 2, at block 206, the system may associate (e.g., tests for association) the plurality of medical diagnosis scores with each candidate genetic variant of a plurality of candidate genetic variants expressed by the group of clinical subjects from whom the plurality of medical images was taken. In doing so, the system determines whether there is a statistically significant association between a particular candidate genetic variant and the disease of interest.

In some embodiments, associating the plurality of medical diagnosis scores with the candidate genetic variant comprises generating a variant-specific model configured to receive a candidate genetic variant value and output a medical diagnosis score. For example, if the candidate genetic variant is genetic variant A, the system can generate a model configured to receive a value indicative of genetic variant A and output a predicted fibrosis score. In the depicted example in FIG. 3B, a variant-specific variant-score prediction model 316 can be generated as described below.

The variant-specific model (e.g., variant-specific variant-score prediction model 316) can be a linear regression model. In some embodiments, a linear regression model is:

$$y = Fb + x\beta + \psi$$

where $\psi \sim N(0, \sigma_e^2 I_N)$.

$y \in R^{N \times 1}$ represents medical diagnosis scores (e.g., biopsy level fibrosis scores) for N individuals.

$X \in R^{N \times 1}$ represents genotype vector of the genetic variant being tested. For example, for a genetic variant with two alleles in the population, the genotype vector has values 0, 1, or 2 depending on if each individual has 0, 1, or 2 copies of the least frequent allele.

$F \in R^{N \times K}$ represents a matrix of K covariates (e.g., sex, age, clinical trial arm). In one exemplary implementation, there are 5 covariates: sex, age, and three treatment groups. The first column of F is a binary indicator of patients' sex (e.g., 0 for XX chromosomes and 1 for XY chromosomes), the second column contains patients' age, and the remaining columns are binary indicators for the three treatments (e.g., 1 if the patient received a specific treatment, 0 otherwise).

Figure 6:
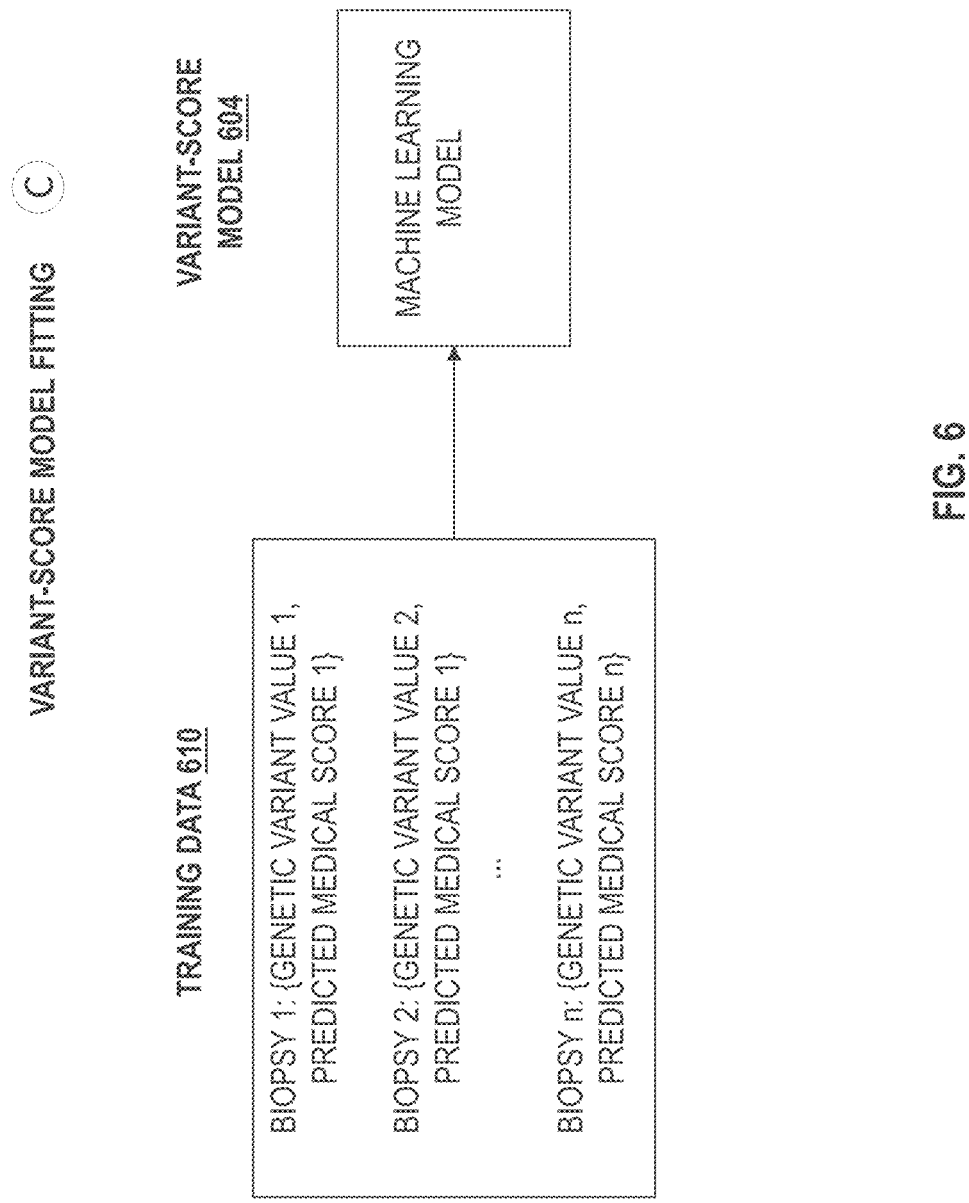
FIG. 6 illustrates fitting of an exemplary variant-specific model for predicting medical diagnosis scores, in accordance with some embodiments.

FIG. 6 depicts fitting an exemplary variant-specific model for predicting medical diagnosis scores, in accordance with some embodiments. As shown, variant-score prediction model 604 is fitted using training data 610. Training data 610 comprises data of biopsies 1-n, including genetic variant values of the subjects and the corresponding predicted medical scores. For example, the data comprises a genetic variant value of the subject that biopsy 1 is performed on, and the predicted fibrosis score for biopsy 1, etc.

Turning back to FIG. 3B, as shown, variant-specific model 316 may be fit using the predicted fibrosis scores for biopsies 1-n. In some embodiments, the system fits a plurality of variant-specific models, such as variant-score prediction models 316 and 322, corresponding to a plurality of candidate genetic variants. For example, variant-specific model 316 can be specific to candidate genetic variant A and is configured to receive a value indicative of candidate genetic variant A and predict a medical diagnosis score, while variant-score prediction model 322 can be specific to candidate genetic variant B and is configured to receive a value indicative of candidate genetic variant B and predict a medical diagnosis score. Thus, the system can generate variant-specific models (e.g., 100,000 models, 1 million models, 10 million models, or other quantities of models) for all candidate genetic variants (e.g., 100,000 variants, 1 million variants, 10 million variants, or other quantities of variants).

At block 208, the system may determine, based on the association, a correlation metric between the disease of interest and each candidate genetic variant to identify at least one genetic variant of interest. The correlation metric is indicative of an impact of the candidate genetic variant on the disease of interest. In some embodiments, the correlation metric quantifies the association between the genetic variant and the disease of interest. With reference to FIG. 3B, variant-specific model 316 may be used to determine a correlation metric 318 between the disease of interest (represented by the medical diagnosis score) and genetic variant A, and variant-score prediction model 322 may be used to determine a correlation metric 324 between the disease of interest and genetic variant B, etc. Thus, a correlation metric may be calculated for each genetic variant of interest.

In some embodiments, the correlation metric is the P value of a linear regression model (such as, for example, variant-score model 604). The system tests $\beta \neq 0$. P values can be obtained through a standard log likelihood ratio test procedure and the effect size and standard errors can be obtained through classical linear model theory. The procedure returns the P value of association between the tested variant and the medical diagnosis score, the effect size of the variant (the estimator of the weight β in the linear model), the standard error (the error on the effect size estimate from the model), or other information.

In some embodiments, the correlation metric is compared with one or more predefined threshold to determine if there is a significant association between the genetic variant of interest and the disease of interest. For example, if the P value is smaller than a predefined threshold (e.g., $5 \times 10^{-8}$), the system may determine that there is a significant association. In some embodiments, the system identifies, based on the comparison, a relationship between the genetic variant of interest and the disease of interest. In some embodiments, the relationship is a causal relationship. The identified relationship or association can be used for diagnosis and development of treatments and drugs, as described below.

The techniques described herein with reference to FIGS. 2-6 are merely exemplary and similar techniques can be applied to discover associations between any phenotype of interest and a covariate. In some examples described herein with reference to FIGS. 2-6, the phenotypic data comprises medical images; the phenotype of interest is a disease of interest (e.g., NASH), which can be represented by a medical diagnosis score (e.g., fibrosis score); and the covariate of interest is a genetic variant of interest. However, it should be understood that the techniques described herein can be applied to discover associations between another phenotype of interest and another covariate. Exemplary phenotypic data include, but is not limited to, medical images (e.g., MRI, X-ray, CT scan), histopathology data (e.g., H&E stained, Trichrome), clinical biomarker data (e.g., blood test measurements, including proteomic and cfDNA, cognitive/psychiatric assessment scores, microbiome assessment, etc.), or genomic biomarker data (e.g., bulk RNA-seq, methylation data, genomic sequence data, epigenetic sequence data, etc.). Exemplary phenotypes include: a disease of interest, gene expression, metabolomics, proteomics, transcriptomics, lipidomics, etc. Exemplary covariate classes include: demographic information (e.g., age, sex), clinical covariates (e.g., a disease state, a clinical score or a blood biomarkers), genomic data (e.g., genetic data, expression data, methylation data, etc.), etc.

In some embodiments, the system identifies, based on the comparison, a relationship between the genetic variant of interest and the disease of interest. In some embodiments, the relationship is a causal relationship. The identified relationship can be used to determine the likelihood that a disease of interest will develop in a new subject or to more confidently diagnose the presence of the disease in a new subject given certain symptoms or the presence of other disease-associated factors. Additionally, if the genetic variant is identified in the new subject, a diagnosis or prognosis of the disease of interest can be provided accordingly, including a prognosis regarding how the disease can be expected to progress. For example, if the genetic variant of interest is discovered for NASH, genomic testing can be performed on a new subject to detect the variant. If the variant is present, the system can predict disease onset, provide a diagnosis, and/or a prognosis regarding how the disease can progress.

In some embodiments, the identified relationship can be used to identify biomarkers or targets for disease intervention. For example, certain genetic variants identified as having a causal relationship with disease onset or progression can be further evaluated for their amenability to therapeutic intervention. Additionally, in view of the functional impact of the genetic variant on the disease of interest, additional biological targets may be identified for therapeutic intervention. Such biological targets, may, for instance, be proteins transcribed by the gene in which the genetic variant of interest is located. Such biological targets may also comprise other genes, proteins or metabolites anticipated to alter, offset, mitigate, supplement or complement the functional impact of the at least one genetic variant on the disease of interest. In some embodiments, the identified relationship can be used to develop a treatment. For example, the impact of candidate therapies previously administered to a group of subjects having the associated genetic variant can be taken into account in developing candidate therapy modifications or analogs. Both longitudinal and cross sectional data regarding the effects of such previously administered candidate therapies can be compared to a predicted state or progression of a disease of interest to determine, quantitatively, the extent to which a genetic variant of interest affects the impact of previously administered candidate therapy on a state or progression of the disease of interest. Such candidate therapy modifications or analogs may be selected to have an enhanced therapeutic effect or reduced adverse side effects in view of the impact of the genetic variant vis-à-vis the disease and that group of subjects. Additionally, disease models reflecting the genetic variant can be used for screening therapeutic candidates. For example, in the case of association with genomic features, statistically significant associations can lead to discovery of new candidate drug targets or key pathways implicated with human disease. Similarly, the impact of candidate therapies previously administered to a group of subjects having the associated genetic variants, including adverse impact on the disease state or side effects, can be used to develop combination therapies. Thus, techniques described herein can be used for predicting likely responses to therapeutic candidates among subjects with different genetic backgrounds, identifying suitable patent cohorts to receive a particular therapy, and generally designing clinical trials to optimize outcomes.

In some embodiments, the identified relationship can be used to selectively administer, adjust, or apply a treatment. In some embodiments, the identified relationship can be used to provide a medical recommendation. In some embodiments, a report can be generated based on the identified relationship. In case of association with demographic and clinical features, significant associations can lead to the discovery of new associations (e.g., associations with sex, age, cholesterol levels) and/or detect technical biases in the datasets (e.g., associations with a particular clinical center).

FIG. 7 illustrates a process 700 for identifying at least one genetic variant of interest with respect to a disease of interest, according to various examples. Process 700 is performed, for example, using one or more electronic devices implementing a software platform. In some examples, process 700 is performed using a client-server system, and the blocks of process 700 are divided up in any manner between the server and one or more client devices. Thus, while portions of process 700 are described herein as being performed by particular devices of a client-server system, it will be appreciated that process 700 is not so limited. In other examples, process 700 is performed using only a client device or only multiple client devices. In process 700, some blocks are, optionally, combined, the order of some blocks is, optionally, changed, and some blocks are, optionally, omitted. In some examples, additional steps may be performed in combination with the process 700. Accordingly, the operations as illustrated (and described in greater detail below) are exemplary by nature and, as such, should not be viewed as limiting.

With reference to FIG. 7, at block 702, an exemplary system (e.g., one or more electronic devices) may be configured to input a plurality of medical images obtained from a group of clinical subjects into a trained unsupervised machine-learning model to obtain a plurality of embeddings in a latent space, each embedding corresponding to a phenotypic state relative to the disease of interest reflected in one or more of the plurality of medical images.

Figure 8A:
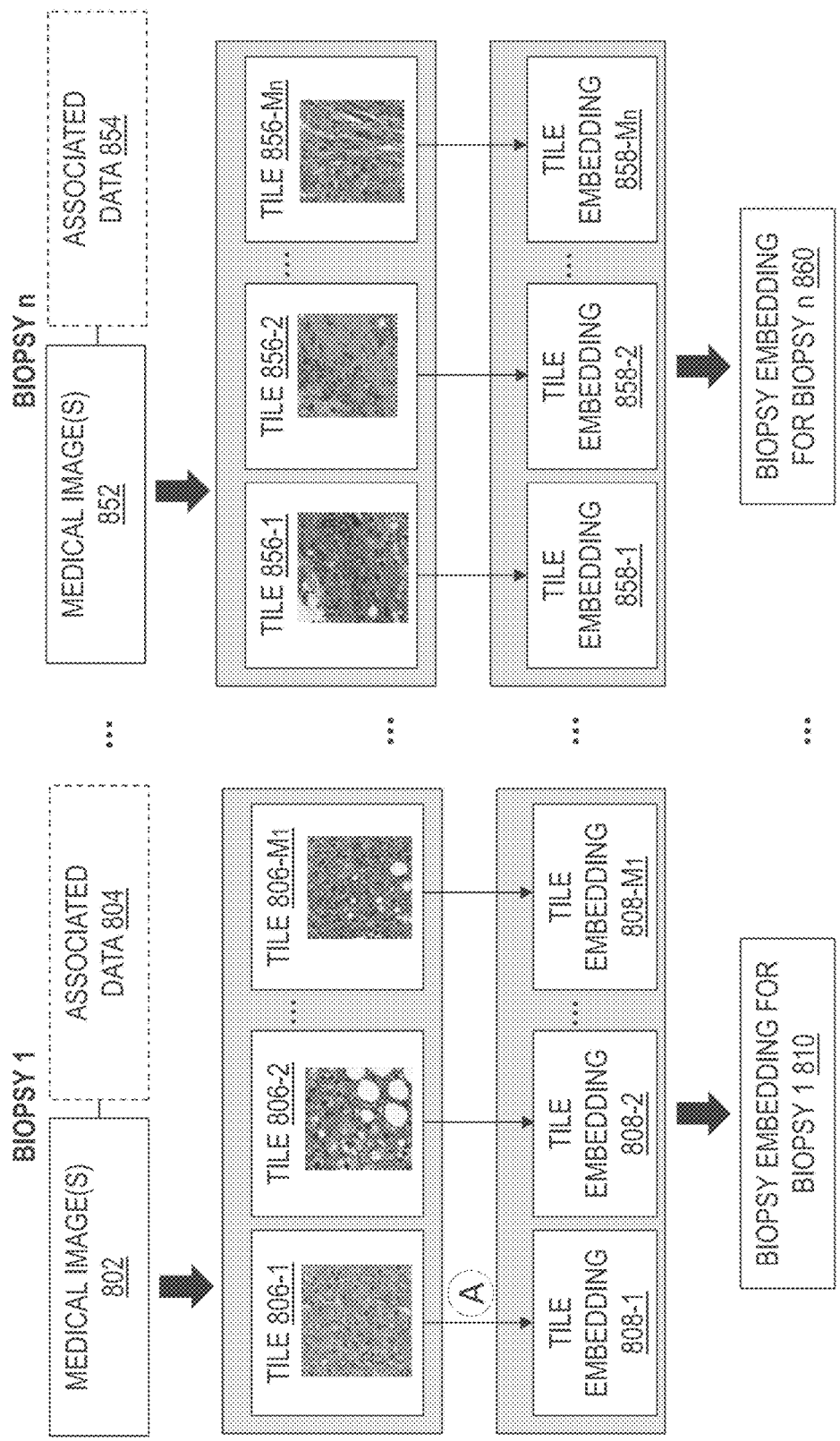
FIGS. 8A and 8B illustrate an exemplary workflow for identifying a genetic variant of interest with respect to a disease of interest, in accordance with some embodiments.

In an exemplary workflow depicted in FIG. 8A, biopsies 1-n have been performed. Biopsies 1-n may correspond to multiple subjects (e.g., cancer patients) and/or multiple visits (e.g., screening visit, follow-up visit) of a same subject. In the depicted example, the disease of interest is non-alcoholic steatohepatitis (NASH) and the biopsies are H&E stained liver biopsies from a number of clinical trials. Each biopsy (e.g., biopsy 1) results in one or more biopsy images (e.g., medical image(s) 802 for biopsy 1). Thus, biopsy 1-n result in a plurality of medical images including medical image(s) 802, medical image(s) 852, etc.

The medical images can be associated with various data. For example, with reference to FIG. 8A, data 804 is associated with medical image 802 for biopsy 1, data 854 is associated with medical image 852 for biopsy n, etc. As described below, the data include known information about the disease of interest and the subject, including information related to the genetic variant of interest.

In some embodiments, the data associated with a medical image can include an assigned medical diagnosis score related to the disease of interest. The assigned medical diagnosis score can indicate the state or the progression of a disease. In some embodiments, a medical diagnosis score can be a biopsy-level score assigned by one or more pathologists based on their review of the biopsy slides. For example, for the NASH disease, the assigned medical diagnosis score can be a biopsy-level fibrosis score, such as the Ishak fibrosis score, which is a score having a discrete value 0, 1, 2, 3, 4, 5, or 6 to indicate the extent of fibrosis.

In some embodiments, the data associated with a medical image can include genetic data of the subject from whom the biopsy sample is taken. For example, the data can include the subject's genetic information related to a plurality of genetic variants (e.g., 100,000 variants, 1 million variants, 10 million variants). For example, the data can indicate whether the subject has each of the plurality of genetic variants. For example, for a genetic variant with two alleles in the population, the medical image may be associated with a genetic variant value of 0, 1, or 2 depending on if the individual has 0, 1, or 2 copies of the least frequent allele. In some embodiments, the genetic data of the subject may be a polygenic risk score, indicating a likelihood of the subject incurring a disease of interest.

In some embodiments, the data associated with a medical image can include demographic data of the subject from whom the biopsy sample is taken. The demographic data can include, for example, sex, age, treatment group (e.g., placebo, treatment x, treatment y), or other data.

With reference to FIG. 8A, a medical image can be split into a plurality of image tiles. For example, medical image(s) 802 of biopsy 1 can be split to obtain image tiles 806-1-806-$M_1$, and medical image(s) 852 of biopsy n can be split to obtain image tiles 856-1-856-$M_n$. In some embodiments, image tiles can be extracted from a medical image using a predefined grid and stored as image tiles of a uniform size. In one exemplary implementation, the image tiles are extracted using a predefined grid with tile dimensions 192 m×192 m and the image tiles are saved as images sized 224 pixels×224 pixels. In some embodiments, the image tile size may be dynamically configurable and adjusted on a case by case basis.

In some embodiments, the system is configured to split the plurality of medical images into a plurality of image tiles and input each image tile into the unsupervised machine-learning model to obtain a corresponding tile embedding. With reference to FIG. 8A, each of image tiles 806-1-806-$M_1$ is input into the unsupervised machine-learning model (represented by process A) to obtain a tile embedding 808-1-808-$M_1$. Accordingly, for biopsy 1, the system may obtain tile embeddings 808-1-808-$M_1$ corresponding to image tiles 806-1-806-$M_1$. Similarly, for biopsy n, the system may obtain tile embeddings 858-1-858-$M_n$ corresponding to image tiles 856-1-856-$M_n$.

In some embodiments, the system selects a subset of the plurality of image tiles for further processing by the unsupervised machine-learning model. For example, the system can determine the portion of a given image tile that depicts biopsy material and only input the image tile if the portion exceeds a predefined threshold (e.g., >90%). As another example, the system can determine the count of image tiles resulting from a given biopsy, and only input the image tiles if the count exceeds a predefined threshold (e.g., >70 tiles).

An exemplary unsupervised machine-learning model used in block 702 is illustrated in FIG. 4A, as described in detail above. Training of an exemplary contrastive learning algorithm is illustrated in FIG. 4B, as described in detail above. In some embodiments, the model can be trained using non-medical images and then used to process medical images in block 702 in FIG. 7. In some embodiments, the model is first trained using non-medical images, then fine-tuned (e.g., retrained) using medical images for a number of epochs (e.g., 5 epochs, 10 epochs, 50 epochs, 100 epochs), and then used to process input medical images in block 702 in FIG. 7. In some embodiments, the medical images used to fine-tune the model can be selected from the image tiles from biopsies 1-n. In other words, the image tiles from biopsies 1-n may be first used to train the model, and then inputted into the trained model to obtain tile embeddings.

The tile embeddings can be aggregated on the biopsy level. The aggregation can comprise averaging the tile embeddings across all tiles in a biopsy. With reference to FIG. 8A, tile embeddings 808-1-808-$M_1$ of biopsy 1 can be aggregated to obtain a biopsy embedding 810. Similarly, tile embeddings 858-1-858-$M_n$ of biopsy n can be aggregated to obtain a biopsy embedding 860. Each biopsy embedding corresponds to a phenotypic state relative to the disease of interest reflected in the biopsy. In an exemplary implementation, 6,782 biopsies result in 6,782 biopsy embedding. Each biopsy embedding is a 2048-dimensional vector calculated by averaging multiple 2048-dimensional tile embedding vectors. This data can be represented as a 6,782×2,048 matrix ($X \in R^{N \times L}$, N=6,782 and L=2,048). In some embodiments, the biopsy embeddings are normalized before further processing. For example, the biopsy embeddings can be standardized and then rescaled by the inverse of the square root of the number of embedding dimensions before further processing. The normalization can improve the performance of predictive models fitted based on the biopsy embeddings, as discussed herein.

At block 704, the system may be configured to associate the plurality of embeddings with each candidate genetic variant of a plurality of candidate genetic variants to identify a subset of candidate genetic variants that are associated with microscopic structure of tissues (histology). Specifically, by assessing association between genetic variants and biopsy embeddings, the system can identify a subset of the plurality of genetic variants that are associated with histological differences. The techniques described herein can identify variants that affect histology that would not be discovered by focusing the analysis on specific diagnostic scores.

In some embodiments, the association comprises generating (e.g., fitting), for each candidate genetic variant of the plurality of candidate genetic variants, a variant-specific model and evaluating the variant-specific model to determine whether there is an association between the genetic variant and the embeddings based on one or more thresholds. If there is an association, the system may include the candidate genetic variant in the subset of candidate genetic variants for further downstream processing. The system can generate variant-specific models (e.g., 100,000 models, 1 million models, 10 million models, etc.) for all genetic variants of interest (e.g., 100,000 variants, 1 million variants, 10 million variants, etc.).

Figure 8B:
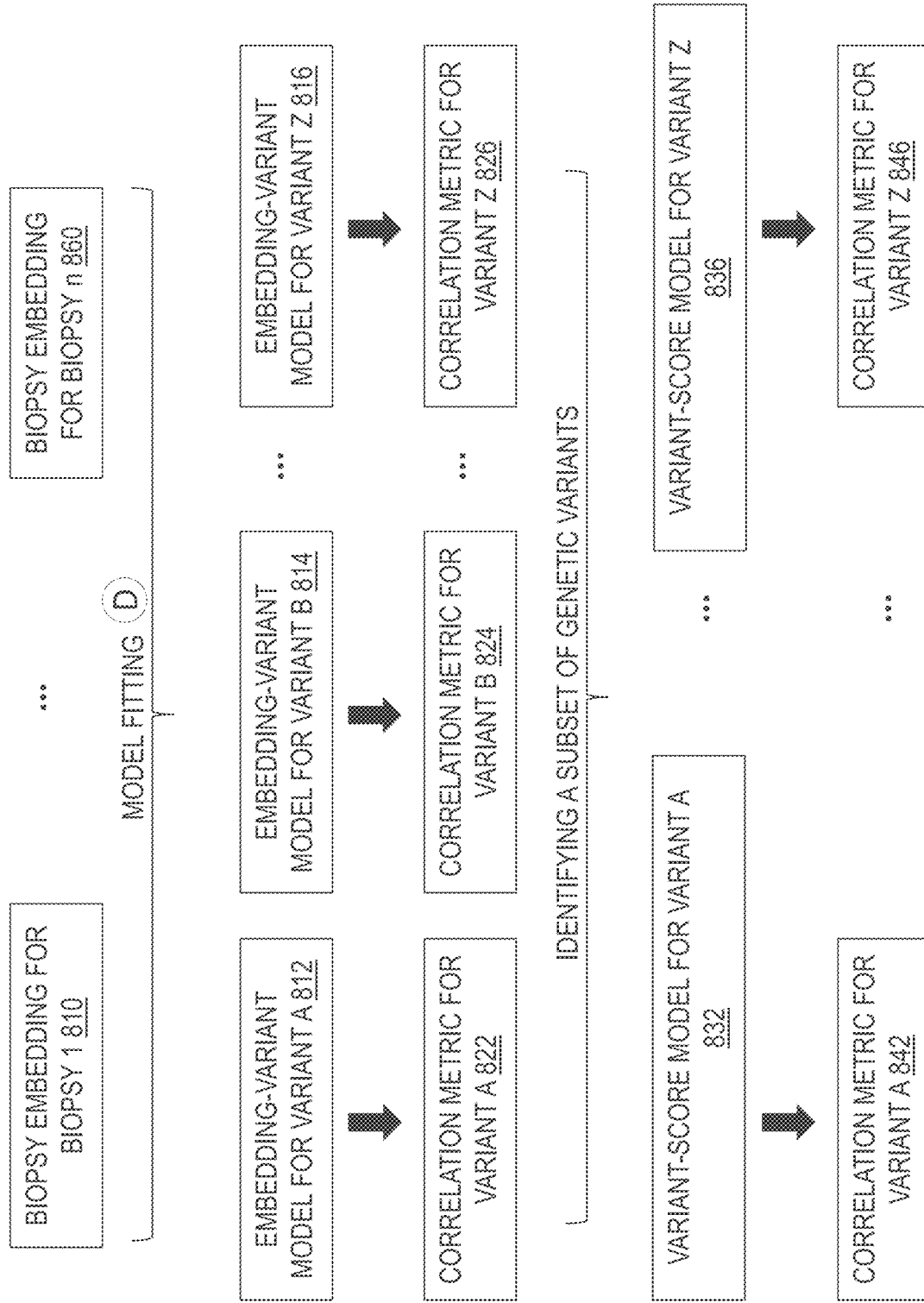

In the depicted example in FIG. 8B, the biopsy embeddings may be used to generate (e.g., fit) an embedding-variant model 812 for variant A, an embedding-variant model 814 for variant B, an embedding-variant model 816 for variant Z, etc. The system can then evaluate each model by calculating a correlation metric for each model. For example, the system can calculate a correlation metric 822 for embedding-variant model 812, a correlation metric 824 for embedding-variant model 814, and a correlation metric 826 for embedding-variant model 816. Each correlation metric can be evaluated (e.g., compared against a predefined threshold) to determine whether there is a significant association between the genetic variant and the embeddings. In the depicted example, the system determines that: an association exists between variant A and the embeddings based on the correlation metric 822, an association exists between variant Z and the embeddings based on the correlation metric 826, and an association does not exist between variant B and the embeddings based on the correlation metric 824. Accordingly, the system may include variant A and variant Z in the subset for further processing, while excluding variant B from the subset. By identifying the subset of genetic variants, the system can identify the genetic variants that are associated with the depicted histological features of the medical images (e.g., biopsy images) for further processing. This smaller set of genetic variants are explored in downstream analyses, for example, to identify the association between each genetic variant and the disease of interest as described below.

In some embodiments, the variant-specific model (e.g., embedding-variant model 812, 814, 816) is a linear regression model configured to receive embeddings as input and output a value indicative of a genetic variant. In some embodiments, the linear regression model can be implemented as a linear mixed model.

In some embodiments, the linear regression model can be:

$$g = Fb + u + \psi \text{ where:}$$

$g \in R^{N \times 1}$ represents the genotype vector of the genetic variant being tested. N is the number of individuals for which both biopsy imaging data and genetic data are available.

$F \in R^{N \times K}$ represents matrix of K covariates (e.g., sex, age, clinical trial arm). In an exemplary implementation, the matrix contains information on sex, age and the three treatment groups (K=5). Specifically, the first column of F is a binary indicator of patients' sex (0 if the patient's chromosomes are XX, 1 if the patient's chromosomes are XY), the second column contains the patients' age, and the remaining columns are binary indicators for the three treatments (1 if the patient received that specific treatment, 0 otherwise).

$X \in R^{N \times L}$ represents the input matrix of biopsy embeddings with dimension L for N individuals (e.g., L=2048).

$b \in R^{K \times 1}$ represents a covariate effect size vector. The vector includes various model parameters and are the weights of the covariates in a linear model. Specifically, there are K weights for the K covariates respectively.

$u \sim N(0, \sigma_x^2 XX^T)$ models the contribution from histological embeddings.

$\psi \sim N(0, \sigma_e^2 I_N)$ is residual iid gaussian noise.

$I_N \in R^{N \times N}$ represents the N×N identity matrix.

$\sigma_x^2$ and $\sigma_e^2$ are scalar model parameters.

In some embodiments, the system generates parameters for the linear regression model (i.e., fits the model). The model can be fit using biopsy data, including biopsy embeddings (e.g., biopsy embeddings 810, 860) and the corresponding medical diagnosis scores. In the depicted example in FIG. 8B, the biopsy embeddings 810, 860 for biopsies 1-n can be used to fit each of the embedding-variant models 812, 814, and 816.

Figure 9:
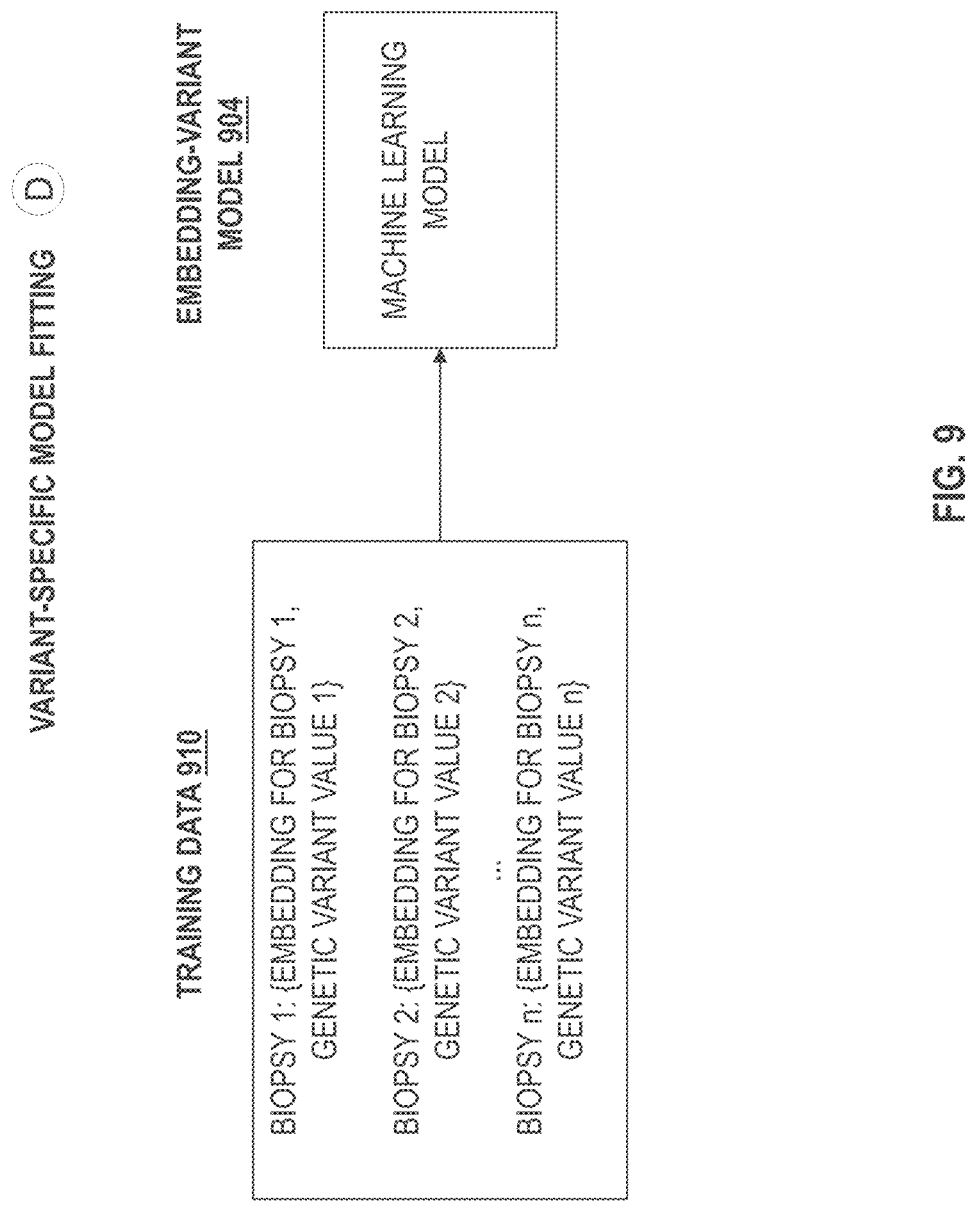
FIG. 9 illustrates fitting of an exemplary linear regression model, in accordance with some embodiments.

FIG. 9 illustrates fitting of an exemplary linear regression model (e.g., embedding-variant model 812). As shown, an embedding-variant model 904 may be fit using training data 910. In some embodiments, model 904 may be a linear regression model. Training data 910 comprises data of biopsies 1-n, including the biopsy embeddings and the corresponding genetic variant values. For example, the embeddings are biopsy embeddings 810, 860 for biopsies 1-n described with reference to FIG. 8B, and the genetic variant values are values indicative of a specific genetic variant (e.g., variant A) in biopsies 1-n (e.g., stored as part of associated data 804, 854 in FIG. 8A).

In an exemplary implementation, 6,782 biopsies result in 6,782 biopsy embeddings. Each biopsy embedding may be a 2048-dimensional vector calculated by averaging multiple 2048-dimensional tile embedding vectors. This data can be represented as a 6,782×2,048 matrix ($X \in R^{N \times L}$, N=6,782 and L=2,048). The matrix is used as the input matrix X to fit the linear regression model. The covariate matrix $F \in R^{N \times K}$ contains an intercept (i.e., a single column (K=1) with all ones).

The negative log marginal likelihood of the linear regression model can be:

$$f(b, \sigma_x^2, \sigma_e^2) = -\log N(y; Fb, \sigma_x^2 XX^T + \sigma_e^2 I_N), \text{with parameters } b, \sigma_x^2 \text{ and } \sigma_e^2.$$

Maximum likelihood estimators (MLE) of b, $\sigma_x^2$, $\sigma_e^2$ can be obtained by minimizing $f(b, \sigma_x^2, \sigma_e^2)$ using a similar efficient procedure. In some embodiments, this can be achieved by (i) rotating the data in a space where the covariance is diagonal $f(b, \sigma_x^2, \sigma_e^2) = -\log N(U^T y; U^T Fb, \sigma_x^2 S + \sigma_e^2 I_N)$ (where the eigenvalue decomposition of $XX^T$ is indicated as $USU^T$), and (ii) reparametrizing the model as $f(b, \sigma^2, \delta) = -\log N(U^T y; U^T Fb, \sigma^2 \delta S + \sigma^2 (1-\delta) I_N)$. In the new form, optimization can proceed by performing a grid search on delta with close form solutions for MLEs of b, $\sigma^2$ for each value of $\delta$. This optimization is also computational efficient. After optimization, the MLEs of $\sigma_x^2$ and $\sigma_e^2$ can be computed as $\hat{\sigma}_x^2 = \hat{\sigma}^2 \hat{\delta}$ and $\hat{\sigma}_e^2 = \hat{\sigma}^2 (1-\hat{\delta})$ respectively from the MLEs $\hat{\delta}$ and $\hat{\sigma}^2$.

After the variant-specific models (e.g., embedding-variant models 812, 814, and 816) are fit, each fitted model is evaluated to determine whether there is an association between the corresponding genetic variant and the embeddings. In some embodiments, evaluating the variant-specific model comprises calculating a correlation metric based on the variant-specific model and comparing the correlation metric with a predefined threshold.

In some embodiments, the correlation metric is a P value associated with the variant-specific model. The P value can be obtained through a permutation procedure where the log likelihood ratio (LLR) statistic from the real data is compared to LLRs obtained when permuting the individuals in the embedding matrix (LLRs from null model). In some embodiments, the P value is defined as the fraction of LLRs under permutations that are greater than the real data LLR.

For example, for each genetic variant, the variant-specific model can be fit on K permutations of the rows of X. For each genetic variant, this procedure produces K number of LLRs. Specifically, fitting the variant-specific model using real data can result in one LLR. Fitting the variant-specific model on K permutations of the rows of X can result in K LLRs. For each genetic variant, the P value is the fraction of K LLRs that are greater than the LLR from real data.

The correlation metric for each genetic variant can be compared against a predefined threshold to determine whether there is an association between the genetic variant and the embeddings. In some embodiments, the threshold can be set to $5 \times 10^{-8}$. For example, variants with P values lower than the threshold are determined to be associated with the embeddings. In the depicted example, the system may be configured to determine that an association exists between variant A and the embeddings based on the correlation metric 822, an association exists between variant Z and the embeddings based on the correlation metric 826, and an association does not exist between variant B and the embeddings based on the correlation metric 824. Accordingly, the system includes variant A and variant Z in the subset for further processing, while excluding variant B from the subset.

At block 706, the system associates each candidate genetic variant of the subset of genetic variants with the disease of interest to identify the at least one genetic variant of interest. In doing so, the system determines whether there is a statistically significant association between a particular genetic variant and the disease of interest. The identified genetic variant of interest is associated with both histology and the disease of interest.

In some embodiments, associating a genetic variant with the disease of interest comprises generating (e.g., fitting) a variant-specific score prediction model configured to receive a genetic variant value and output a medical diagnosis score related to the disease of interest. For example, if the genetic variant to be tested is genetic variant A, the system can generate a model configured to receive a value indicative of genetic variant A and output a predicted medical diagnosis score. With reference to FIG. 8B, a variant-specific score prediction model 832 may be generated for variant A; a variant-specific score prediction model 836 may be generated for variant Z. No variant-specific score prediction model may be generated for variant B because correlation metric 824 for variant B exceeds the predefined threshold and thus variant B can be excluded from further processing.

The variant-score model (e.g., variant-specific score prediction model 832) can be a linear regression model. In some embodiments, the linear regression model is:

$$y = Fb + x\beta + \psi$$

where $\psi \sim N(0, \sigma_e^2 I_N)$.

$y \in R^{N \times 1}$ represents medical diagnosis scores (e.g., biopsy level fibrosis scores) for N individuals.

$X \in R^{N \times 1}$ represents genotype vector of the genetic variant being tested. For example, for a genetic variant with two alleles in the population, the genotype vector has values 0, 1, or 2 depending on if each individual has 0, 1, or 2 copies of the least frequent allele.

$F \in R^{N \times K}$ represents a matrix of K covariates (e.g., sex, age, clinical trial arm). In one exemplary implementation, there are 5 covariates: sex, age, and three treatment groups. The first column of F is a binary indicator of patients' sex (e.g., 0 if the patient's chromosomes are XX and 1 if the patient's chromosomes are XY), the second column contains the patients' age, and the remaining columns are binary indicators for the three treatments (e.g., 1 if the patient received the specific treatment, 0 otherwise). Fitting of an exemplary variant-specific score prediction model is described with reference to FIG. 6.

After a variant-specific score prediction model is fit, the system can determine a correlation metric between the disease of interest and the genetic variant of interest. The correlation metric is indicative of impact of the genetic variant of interest on the disease of interest. With reference to FIG. 8B, variant-specific score prediction model 832 is used to determine a correlation metric 842 between the disease of interest (represented by the medical diagnosis score) and genetic variant A, and the variant-score model 836 is used to determine a correlation metric 846 between the disease of interest and genetic variant Z, etc. Thus, a correlation metric is calculated for each genetic variant of interest in the subset of candidate genetic variants.

In some embodiments, the correlation metric is the P value of the linear regression model. The system tests $\beta \neq 0$. P values may be obtained through a standard log likelihood ratio test procedure and the effect size and standard errors are obtained through classical linear model theory. The procedure returns the P value of association between the tested variant and the medical diagnosis score, the effect size of the variant (the estimator of the weight $\beta$ in the linear model) and the standard error (the error on the effect size estimate from the model).

In some embodiments, the correlation metric is compared with one or more predefined thresholds to determine if there is a significant association between the genetic variant of interest and the disease of interest. For example, if the P value is smaller than a predefined threshold (e.g., $5 \times 10^{-8}$), the system determines that there is a significant association. In some embodiments, the system may identify, based on the comparison, a relationship between the genetic variant of interest and the disease of interest. In some embodiments, the relationship is a causal relationship. The identified relationship or association can be used for diagnosis and development of treatments and drugs, as described herein. For example, the system is robust in that it can take embeddings generated from one data set (i.e., images from a first clinical trial) and apply them with the same predictive effect to images and associated genetic variant data from another data set (i.e., images and associated genetic variants from a second clinical trial), as described herein with reference to FIGS. 16-24.

Turning back to FIG. 7, the system can generate simulated images to visualize the histological effects of an identified generic of interest. This procedure provides visualizations of the associated histological changes, which could not be detected by an association study of the pathologist score. Specifically, at block 708, the system may be configured to generate a plurality of simulated images depicting the disease of interest. The plurality of simulated images corresponds to different values of the at least one genetic variant of interest, as described below.

Figure 10:
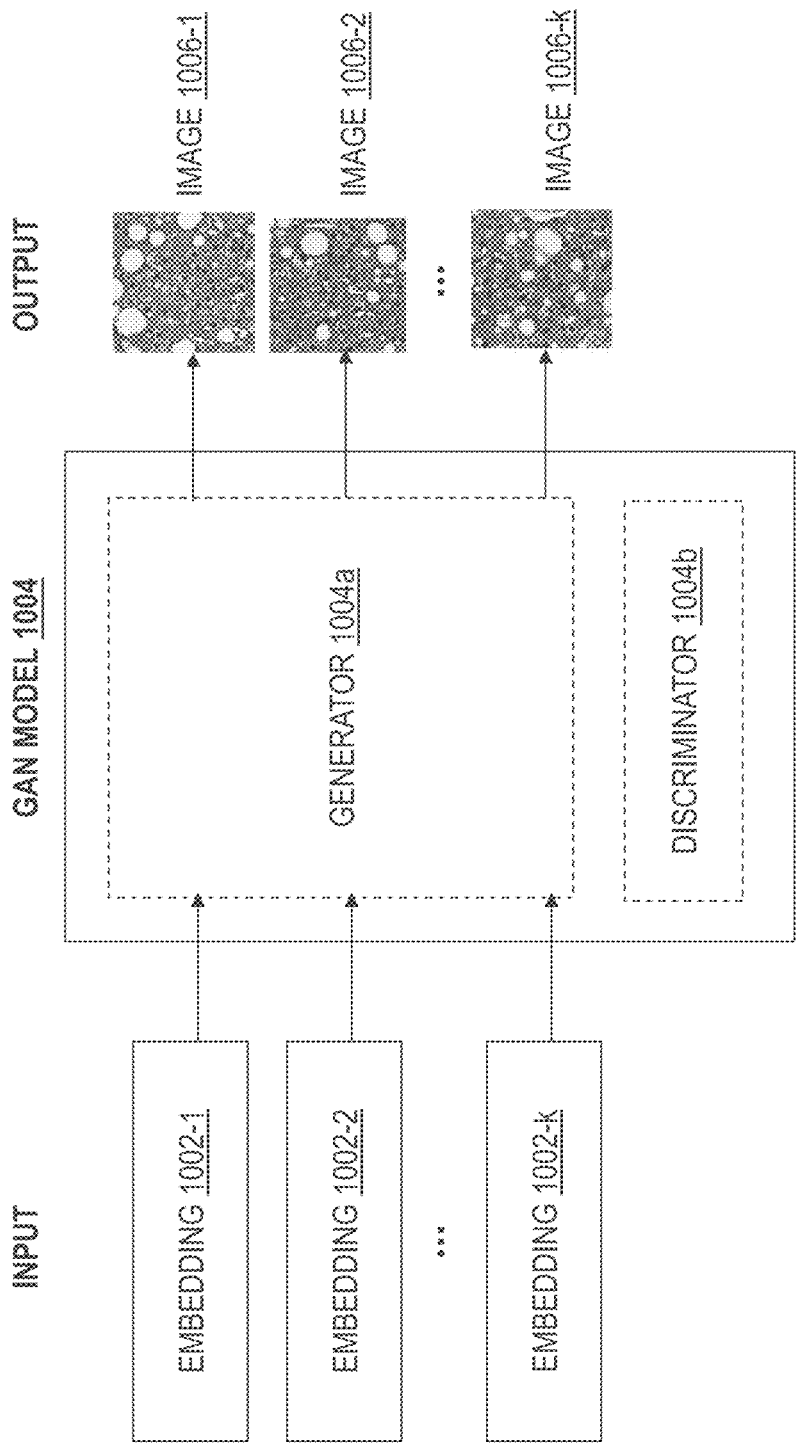
FIG. 10 illustrates an exemplary GAN model, in accordance with some embodiments.

In some embodiments, the system may be configured to generate the predicted images in the form of simulated images using a trained generative model. In some embodiments, the trained generative model is a generative adversarial network (GAN) model. FIG. 10 illustrates an exemplary GAN model 1004, in accordance with some embodiments. In some embodiments, GAN model 1004 may be comprised of a trained generator component 1004a and a trained discriminator component 1004b. Trained generator component 1004a may be configured to receive an embedding (e.g., embeddings 1002-1-1002-$k$) and a noise (not depicted) and output a simulated image (e.g., simulated images 1006-1-1006-$k$). As shown in FIG. 10, trained generator component 1004a may receive embedding 1002-1 and output a simulated image 1006-1, receive embedding 1002-2 and output a simulated image 1006-2, . . . , and receive embedding 1002-$k$ and output a simulated image 1006-$k$.

In some embodiments, to generate embeddings 1002-1-1002-$k$, the system can generate (e.g., fit) a model configured to receive an embedding and output a medical diagnosis score related to the disease of interest. In some embodiments, the model is a linear regression model such as embedding-variant model 812 in FIG. 8B. The model can be then used to predict medical diagnosis scores. For example, each tile embedding (e.g., tile embedding 808-1-808-$M_1$) can be input into the linear regression model to generate a tile-level medical diagnosis score. Tile embeddings from biopsies 1-n can be input to the linear regression model to generate a set of tile-level medical diagnosis scores. The system can identify a first group of tile embeddings having corresponding medical diagnosis scores in the 1-5 percentile and a second group of tile embeddings having corresponding medical diagnosis scores in the 95-99 percentile. A first average embedding can generated by aggregating (as well as taking the average of) the first group of embeddings, and a second average embedding can generated by aggregating (as well as taking the average of) the second group of embeddings. The system can then linearly interpolate between the two average embeddings to obtain embeddings 1-k. Simulated images 1006-1-1006-$k$ corresponding to embeddings 1002-1-1002-$k$ can demonstrate the histological effects associated with progression of the disease of interest.

In some embodiments, to generate embeddings 1002-1-1002-$k$, the system can generate (e.g., fit) a model configured to receive an embedding and output a value of a genetic variant of interest (e.g., the genetic variant of interest identified in FIGS. 2 and 7). The genetic variant values are indicative of genotype information for the genetic variant of interest (e.g., if the individual has 0, 1, or 2 copies of the minor allele at that genetic locus). In some embodiments, the model is a linear regression model similar to as the embedding-score prediction model 312 in FIG. 3A. The model can be then used to predict values of the genetic variant of interest. For example, each tile embedding (e.g., tile embeddings 808) can be input to the linear regression model to generate a tile-level genetic variant value. Tile embeddings from biopsies 1-n can be input to the linear regression model to generate a set of tile-level medical diagnosis scores. The system can identify a first group of tile embeddings having corresponding genetic variant values in the 1-5 percentile and a second group of tile embeddings having corresponding genetic variant values in the 95-99 percentile. A first average embedding can be generated by aggregating (e.g., taking the average of) the first group of embeddings, and a second average embedding can generated by aggregating (e.g., taking the average of) the second group of embeddings. The system can then linearly interpolate between the two average embeddings to obtain embeddings 1-k. The simulated images corresponding to the embeddings 1-k can demonstrate the histological effects associated with the genetic variant of interest.

In some embodiments, the GAN model is a conditional GAN model. For instance, the generator may be configured to receive an embedding, as the condition, and a noise and output a simulated image. The discriminator may be configured to receive an input image, which may be a simulated image or a real image, and classify the input image as simulated or real. During training, the generator generates simulated images, and the simulated images and real images are provided to the discriminator for classification. Based on the outputs of the discriminator, the generator and the discriminator can be updated accordingly to minimize loss. In some embodiments, the generator and the discriminator are neural networks.

Figure 11:
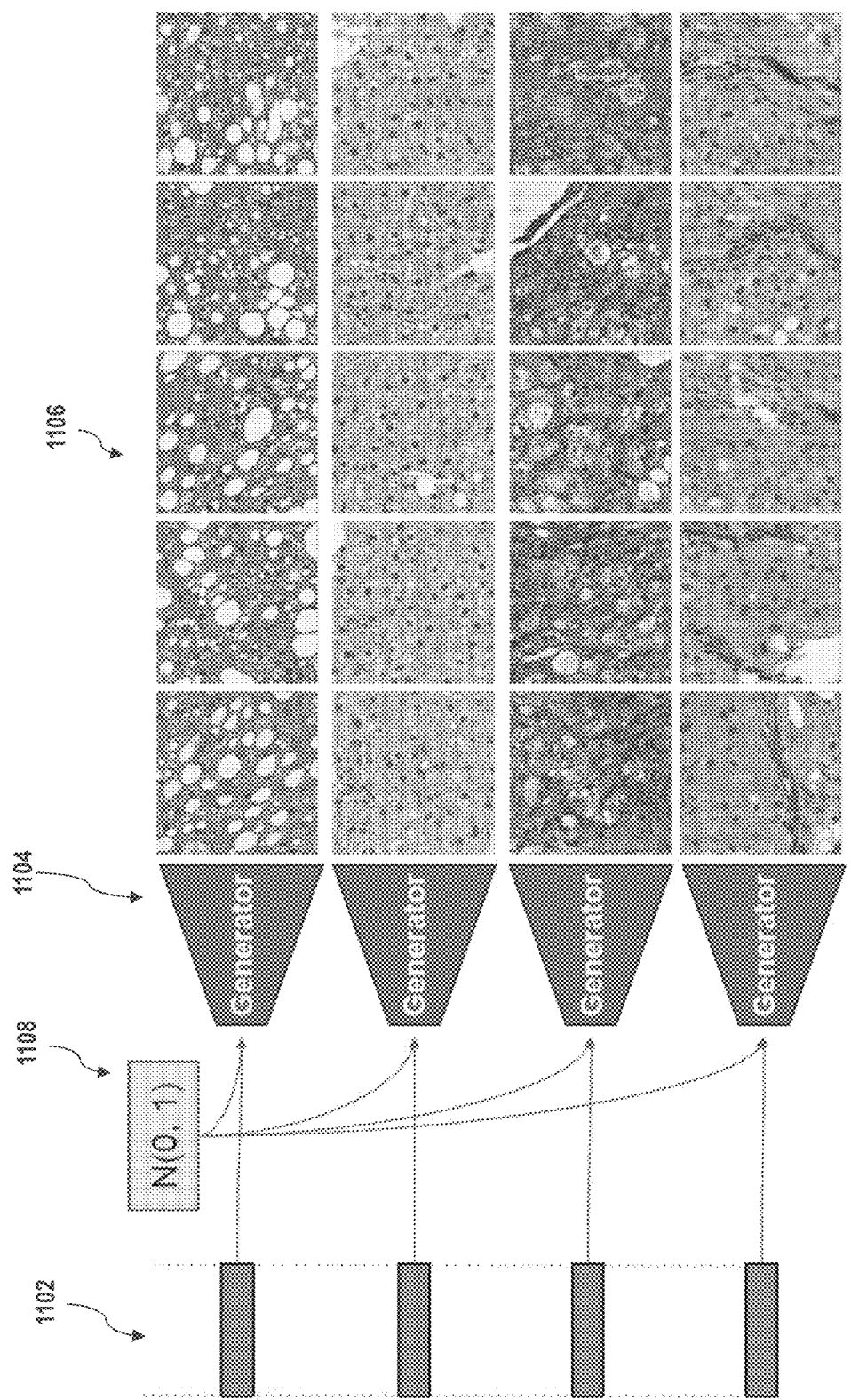
FIG. 11 illustrates generation of predicted simulated images, in accordance with some embodiments.

In some embodiments, the GAN model builds on a progressive GAN (pGAN) model. The pGAN model is trained progressively with increasing image resolution to stabilize training and prevent mode collapse. The system is extended to progressive conditional GAN (pcGAN) model to enable conditioning on the embeddings generated based on medical imaging data described herein. In particular, the generator is configured to receive an embedding x (as the condition) and a noise vector u sampled from a standard normal distribution. Additionally, the discriminator receives generated and real images and the corresponding embedding. FIG. 11 illustrates generation of simulated images process, in accordance with some embodiments. As shown, generators 1104 can receive an embedding 1102 and a noise vector 1108 and output an image 1106. Further, when the same embedding and different noises are provided, different simulated images can be generated. In particular, when each of generators 1104 receives the same embedding 1102 but different noise vectors 1108, different simulated images with the same semantic biological content can be generated. Accordingly, the embedding can be visualized in multiple images to aid the identification and understanding of the histological features associated with the embedding.

In one exemplary implementation, embedding 1102 is a 2048-dimensional embedding and noise vector 1108 is a 512-dimensional vector sampled from a standard normal distribution. Embedding 1102 and noise vector 1108 may be combined into a 512-dimensional vector t that becomes the input of the pGAN generator. The discriminator may be configured to receive an embedding x (as the condition), such as embedding 1102, as input in addition to an image i. This addition enables the discriminator to classify real and fake images also based on the consistency with the input embedding. In an exemplary implementation, the embedding is a 2048-dimensional embedding and the image is a 256×256 image.

In an exemplary implementation, the pcGAN model is first trained on tile images and corresponding embeddings using the same parameters as in pGAN. After training, the generator of the pcGAN model can receive, as input, a 2048-dimensional embedding and a 512-dimensional vector sampled from a standard normal distribution and output a 256×256 simulated tile image (whose content is consistent with the input embedding). Given the 512-dimensional noise vector 1108 sampled from a normal distribution, the system can use pcGAN to generate k images giving as input each of the k interpolation embeddings and the sampled noise from noise vector 1108. Accordingly, this procedure takes as input a covariate of interest (vector across the analyzed biopsies), biopsy embeddings (matrix with analyzed biopsies as rows and embedding dimension as columns), and tile embeddings (matrix with the corresponding tiles as rows and embedding dimension as columns), and may output a series of k 256×256 tile images.

At block 710, the system may be configured to display (or cause to be displayed), on a display, the plurality of predicted simulated images 1106. The display, for example, may correspond to a display screen of a user device, such as a computing device (e.g., computing device 2900 of FIG. 29). In some embodiments, predicted simulated images 1106 can be used to create an animation of histological changes. Multiple animations can be created for the same covariate of interest by providing different 512-dimensional samples from a normal distribution as input to the GAN, as shown in FIG. 11. In some embodiments, the same sample is used across images from the same series of predicted simulated images 1106. In some embodiments, the predicted simulated images may be ranked. The displayed simulated images may include some or all of the predicted simulated images, and may be selected from the predicted simulated images based on the ranking. In some embodiments, the ranking may be based on a corresponding medical diagnosis score. For example, the predicted simulated images may be ranked based on the computed medical diagnosis score of that predicted simulated image (which may be determined based on the embeddings). In some embodiments, the predicted simulated images to be displayed may be selected based on their corresponding medical diagnosis scores. For example, predicted simulated images having a medical diagnosis score in the $1^{st}$-$5^{th}$ percentile, which may represent predictive tiles corresponding to low fibrosis, may be selected for display and/or caused to be displayed within a user interface. As another example, predicted simulated images having a medical diagnosis score in the $95^{th}$-$99^{th}$ percentile, which may represent predictive tiles corresponding to high fibrosis, may be selected for display and/or caused to be displayed. Alternative percentile ranges may be used for selecting predicted simulated images, and the aforementioned ranges are merely exemplary.

Figures 12A, 12B:
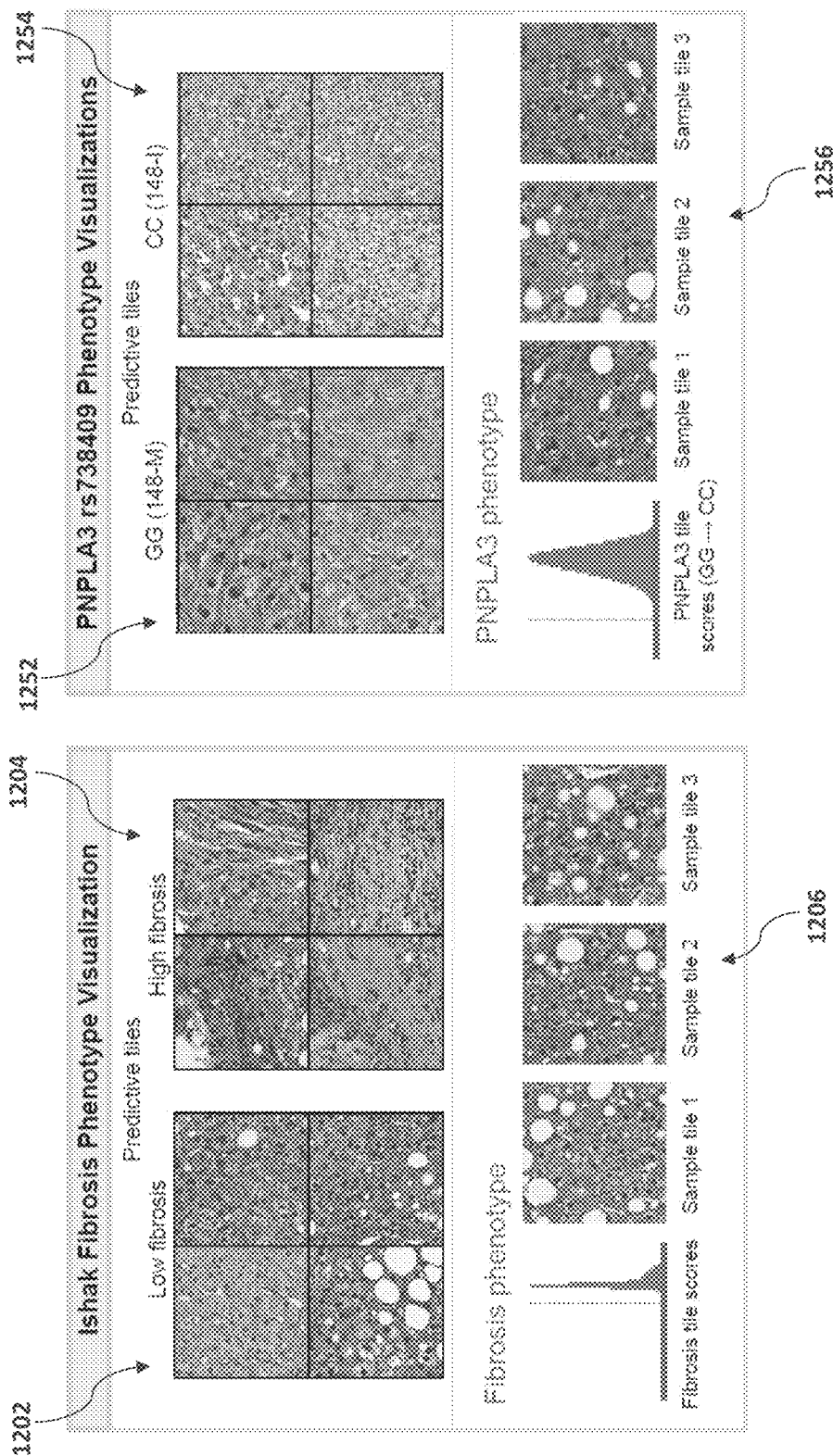
FIG. 12A illustrates an exemplary set of predictive image tiles and an exemplary series of three simulated images to visualize an increasing fibrosis score, in accordance with some embodiments.
FIG. 12B illustrates an exemplary set of predictive image tiles and an exemplary series of three simulated images to visualize an increasing PNPLA3 tile score, in accordance with some embodiments.

FIG. 12A illustrates an exemplary set of predictive image tiles and an exemplary series of three predicted simulated images to visualize an increasing fibrosis score, in accordance with some embodiments. As described above, the system can identify a first group of tile embeddings of images 1202 having corresponding medical diagnosis scores in the $1^{st}$-$5^{th}$ percentile, thus identifying predictive tiles corresponding to low fibrosis. The system can also identify a second group of tile embeddings of images 1204 having corresponding medical diagnosis scores in the $95^{th}$-$99^{th}$ percentile, thus identifying predictive tiles corresponding to high fibrosis. The system can obtain a first average embedding of the first group of tile embeddings and a second average embedding of the second group of tile embeddings. Linear interpolation can be performed to obtain k embeddings. For example, if k=3, the system obtains three embeddings: a first embedding (e.g., the first average embedding), a second embedding (e.g., an average of the first embedding and the third embedding), and a third embedding (e.g., the second average embedding). The three embeddings can be inputted into the generator to obtain a series of images 1206 to visualize the histological changes associated with the increase of the fibrosis score.

FIG. 12B illustrates an exemplary set of predictive image tiles 1252, 1254 and an exemplary series of three simulated images 1256 to visualize an increasing PNPLA3 tile score, in accordance with some embodiments. Images 1256, in some embodiments, may be obtained using similar techniques as described above with reference to FIG. 12A.

In some embodiments, the plurality of predicted simulated images may be ranked. The ranking may be based on fibrosis score or other measures. In some embodiments, some or all of the plurality of predicted simulated images may be displayed. A subset (or all) of the plurality of predicted simulated images may be selected based on the ranking and the predicted simulated images may be selected for display based on the ranking.

Figure 13:
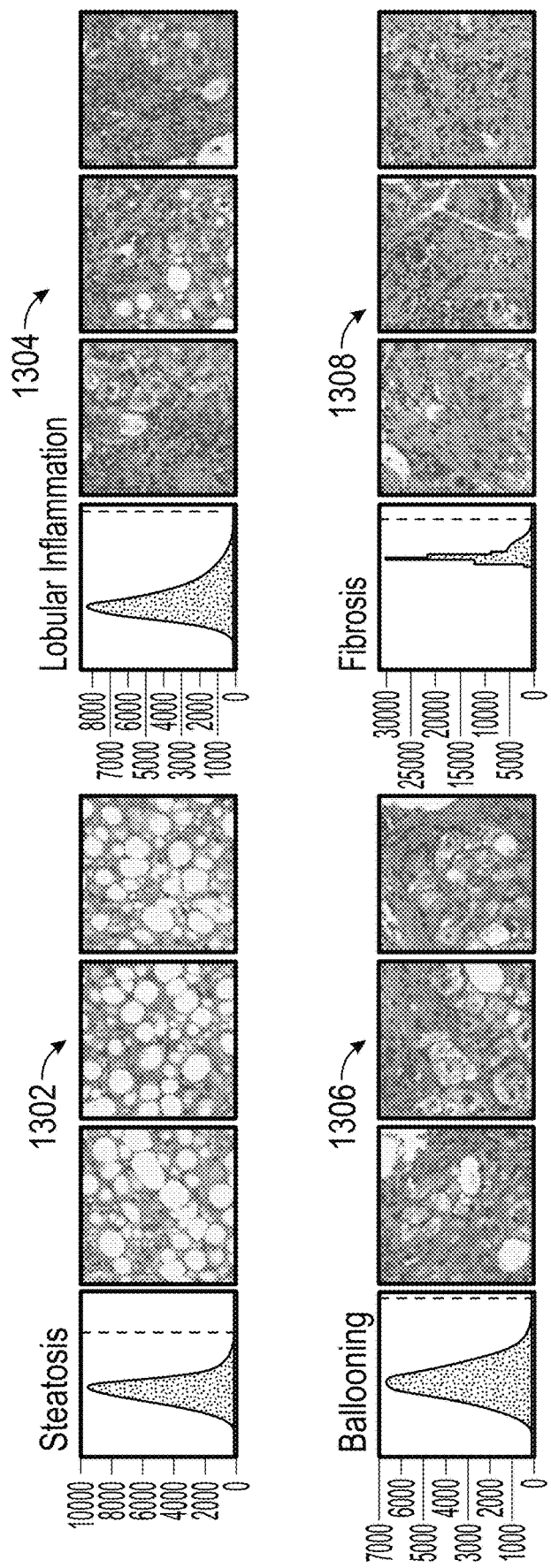
FIG. 13 illustrates an exemplary series of predicted simulated images to visualize histological effects associated with various scores, in accordance with some embodiments.

FIG. 13 illustrates an exemplary series of predicted simulated images 1302 to visualize histological effects associated with the steatosis score, an exemplary series of predicted simulated images 1304 to visualize histological effects associated with the lobular inflammation score, an exemplary series of predicted simulated images 1306 to visualize histological effects associated with the ballooning score, and an exemplary series of predicted simulated images 1308 to visualize histological effects associated with the fibrosis score, which are generated using techniques described herein. In some embodiments, the visualized image tiles (e.g., images 1302-1308) may correspond to tiles predicted to have low scores for a particular phenotype.

Figure 14:
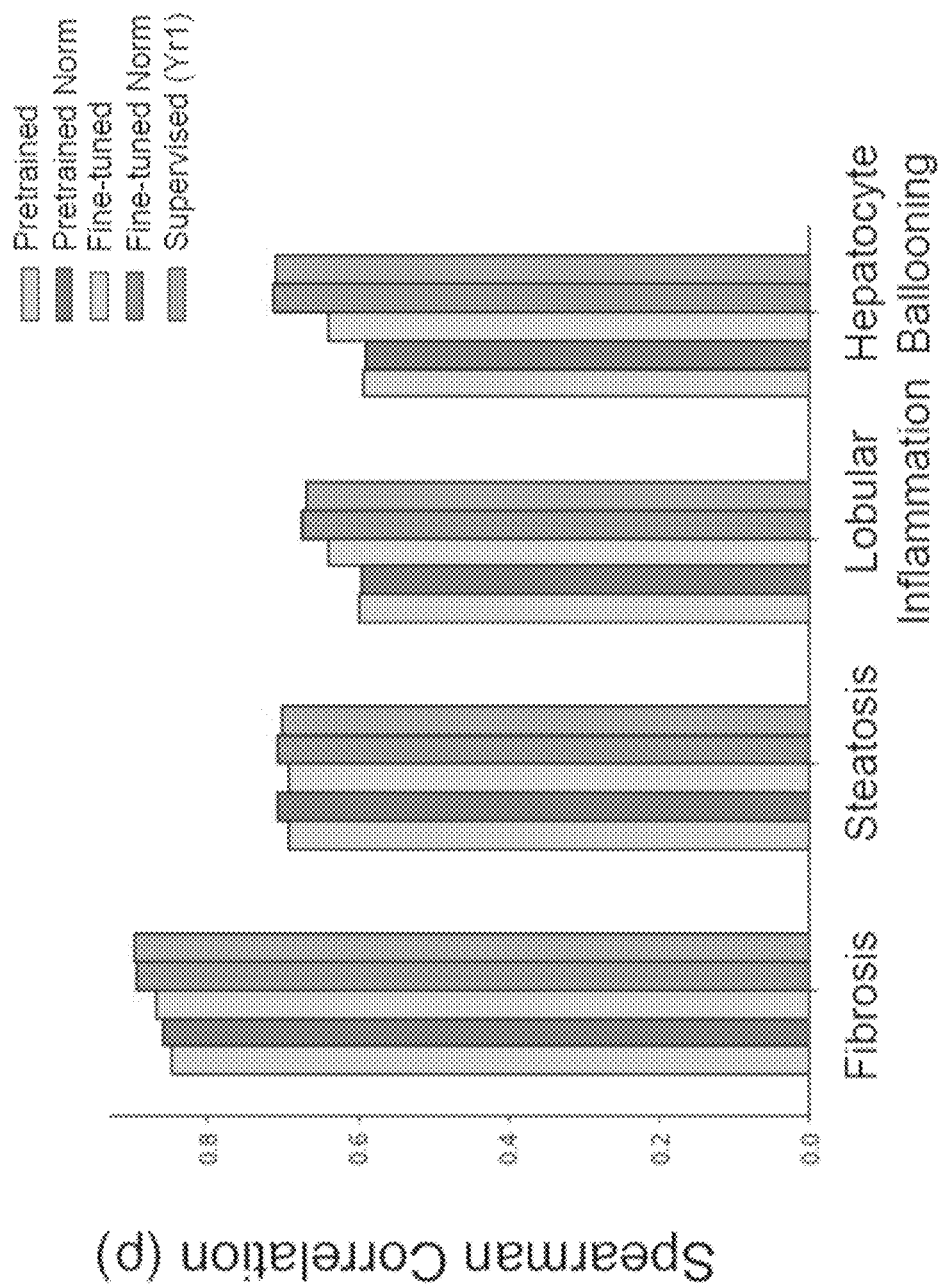
FIG. 14 illustrates the performance of the various linear models configured to predict medical diagnosis scores, in accordance with some embodiments.

FIG. 14 illustrates the performance of the various linear models configured to predict medical diagnosis scores, in accordance with some embodiments. As shown, five models are trained to: predict fibrosis scores; predict steatosis scores; predict lobular inflammation scores; and predict hepatocyte ballooning scores. For each score type, the colors of the bars are in the same order as the colors in the legend.

The first four models are examples of the embedding-score prediction model 312 in FIG. 3A. A pre-trained model refers to a linear model that is fit based on embeddings generated by a pre-trained contrastive model (e.g., SimCLR). A pre-trained contrastive model has not been fine-tuned using images in the same image domain (e.g., liver biopsy images). A pre-trained normalized model refers to a linear model that is fit based on embedding that are both generated by a pre-trained contrastive model and normalized. In some embodiments, the embeddings are standardized and then rescaled by the inverse of the square root of the number of embedding dimensions. A fine-tuned model refers to a linear model that is fit based on embeddings generated by a fine-tuned contrastive model (e.g., SimCLR). A fine-tuned contrastive model has been re-trained using images in the same image domain (e.g., liver biopsy images). A fine-tuned normalized model refers to a linear model that is fit based on embedding that are both generated by a fine-tuned contrastive model and are normalized.

In contrast, a supervised model (e.g., Yr1) refers to a non-linear machine-learning model (e.g., a neural network) configured to receive imaging data and predict a medical diagnosis score. Linear regression models, such as the first four models, are more computationally efficient to train and to apply than the supervised model. As shown in FIG. 14, linear models generated based on embeddings can provide a similar, and in some cases superior, predictive power than supervised machine-learning model, while requiring significantly less resources and time to train and to apply.

Figures 15A, 15B:
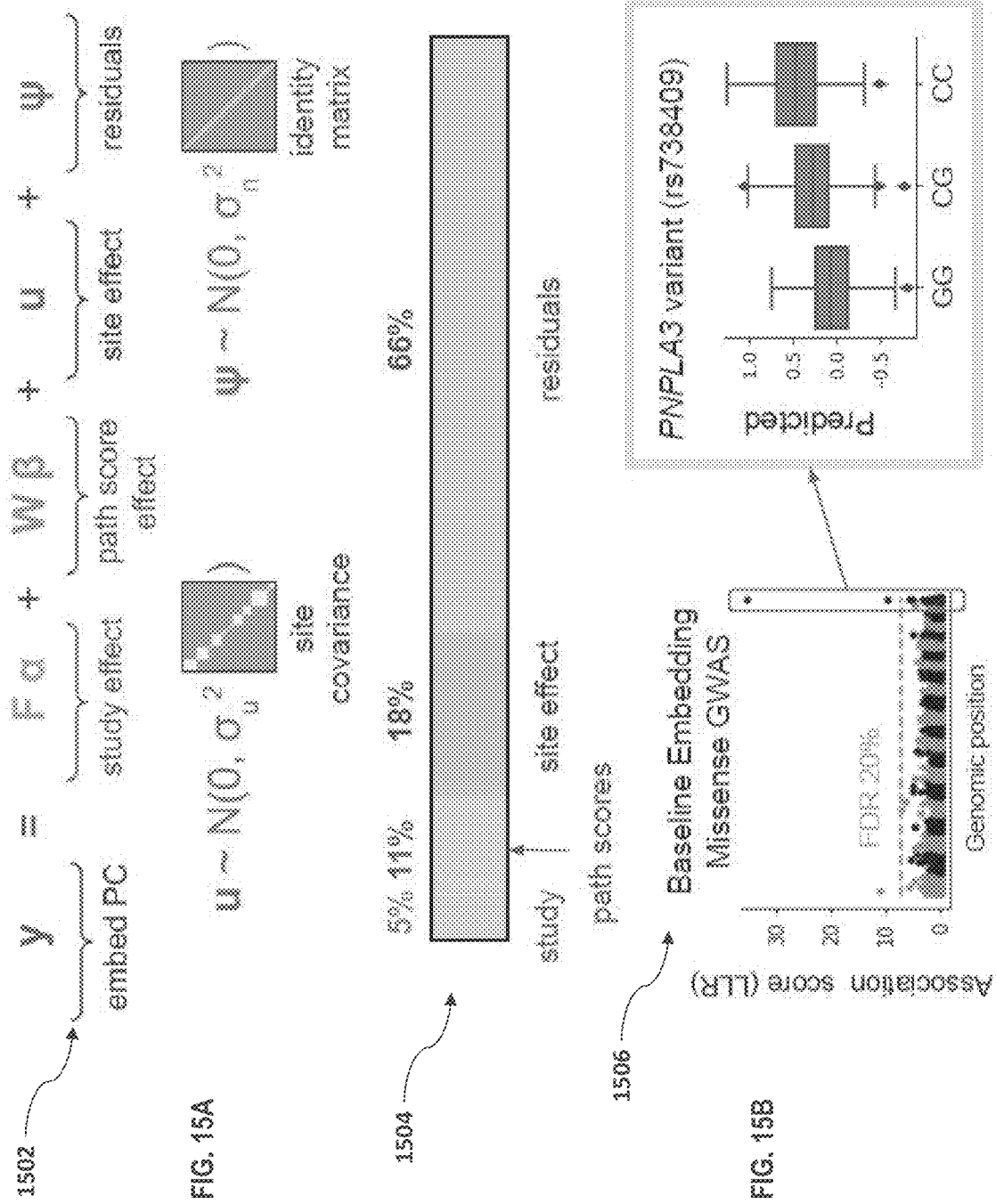
FIG. 15A illustrates a variant component model with study, site, and pathologist score effects, in accordance with some embodiments.
FIG. 15B illustrates an exemplary genome-wide association study (GWAS) of embeddings controlling for site and study affects, in accordance with some embodiments.

FIG. 15A illustrates a variant component model 1502 with study, site, and pathologist score effects. As shown, variant component model 1502 can only explain 34% of the embedding variance, as detailed in plot 1504. FIG. 15B illustrates a genome-wide association study (GWAS) plot 1506 of embeddings controlling for site and study affects. As shown, GWAS plot 1506 identifies three missense variants associated with baseline embeddings. The subset of variants can be further analyzed, as described.

Figure 15C:
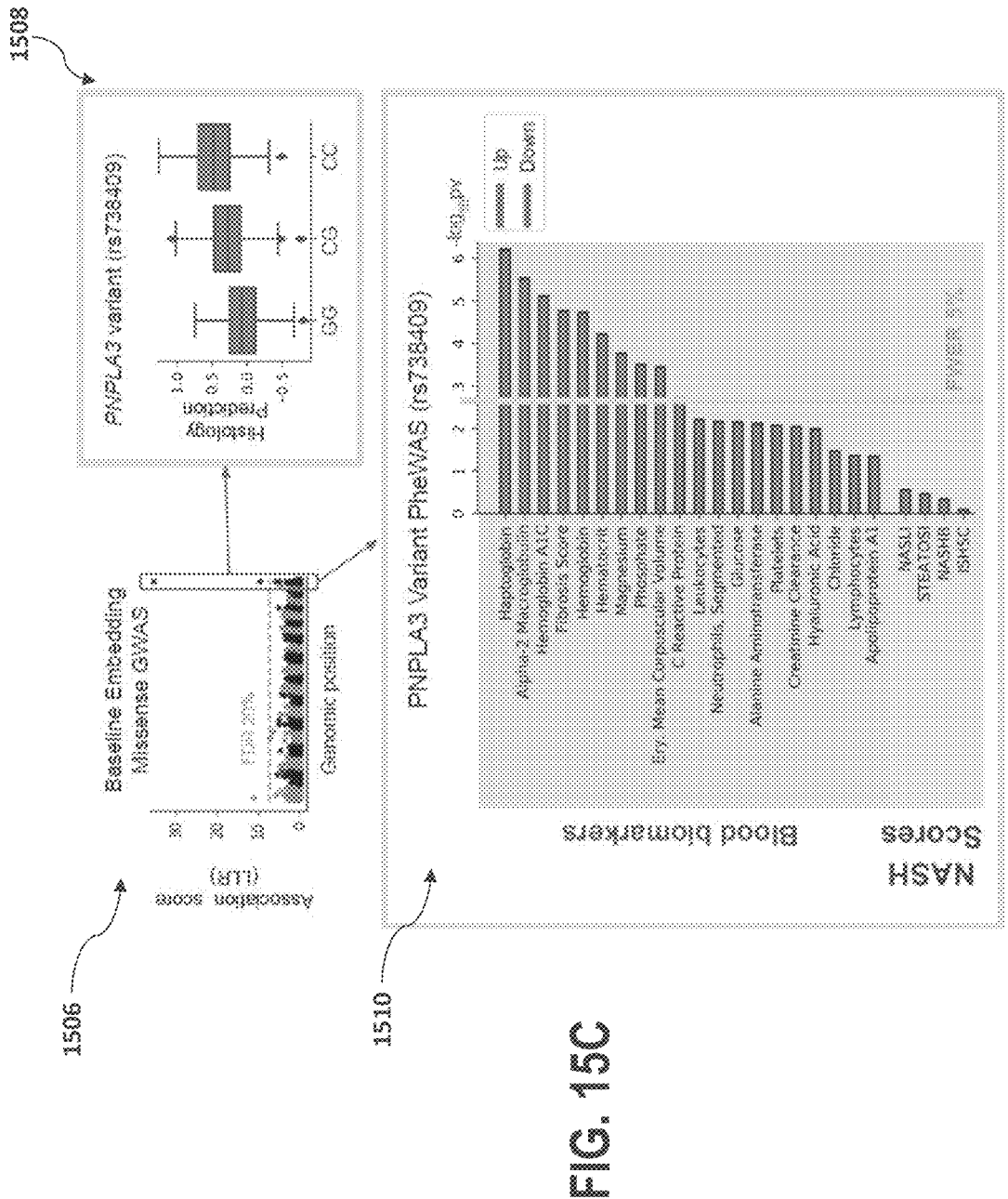
FIG. 15C illustrates an exemplary phenome-wide association study (PheWAS), in accordance with some embodiments.

Genetic variants prioritized through histology analysis, as shown by plot 1508 in FIG. 15B, can be associated with available endpoints to gain insight into associated biology. For example, PheWAS of the lead variant in PNPLA3 rs738409 identifies effects on baseline blood biomarkers and RNA-seq, but not on pathologist or continuous NASH scores. FIG. 15C illustrates a plot 1510 describing that PheWAS of the lead variant in PNPLA3 rs738409 identifies effects on several blood biomarkers and expression pathways. Further, rs738409 is not found to be associated with histological disease labels. Thus, PheWAS in clinical trial data supports interpretation of the discovered genetic effects.

FIGS. 16, 20, 22, and 24 illustrate techniques directed to longitudinal studies (e.g., of treatment effects). It should be appreciated by one of ordinary skill in the art that the longitudinal studies described herein leverage the various techniques for baseline analysis described herein, including trained models and systems. For example, the system receiving longitudinal, progression embeddings for specific subjects as inputs and outputting placebo vs. treatment determinations (e.g., a DRP classification model 1730) may be based on a system that has previously been trained to predict a state or progression of the disease based on a covariant of interest (e.g., genetic variants).

Figure 16:
FIG. 16 illustrates an exemplary method of evaluating a treatment with respect to a disease of interest, in accordance with some embodiments.

FIG. 16 illustrates an exemplary method of evaluating a treatment with respect to a disease of interest, in accordance with some embodiments. In process 1600, the progression of the disease is quantified using progression embeddings. The system may impute drug response phenotype (DRP) as the predictions from a model that receives progression embeddings as inputs and outputs a classification result indicating placebo or the treatment. The system can determine if there is a significant association between the DRP and the treatment. If there is a significant association, the treatment can be further analyzed in downstream analyses (e.g., as described in greater detail below with respect to FIG. 20).

Process 1600 is performed, for example, using one or more electronic devices implementing a software platform. In some examples, process 1600 is performed using a client-server system, and the blocks of process 1600 are divided up in any manner between the server and one or more client devices. Thus, while portions of process 1600 are described herein as being performed by particular devices of a client-server system, it will be appreciated that process 1600 is not so limited. In other examples, process 1600 is performed using only a client device or only multiple client devices. In process 1600, some blocks are, optionally, combined, the order of some blocks is, optionally, changed, and some blocks are, optionally, omitted. In some examples, additional steps may be performed in combination with the process 1600. Accordingly, the operations as illustrated (and described in greater detail below) are exemplary by nature and, as such, should not be viewed as limiting.

Figure 17:
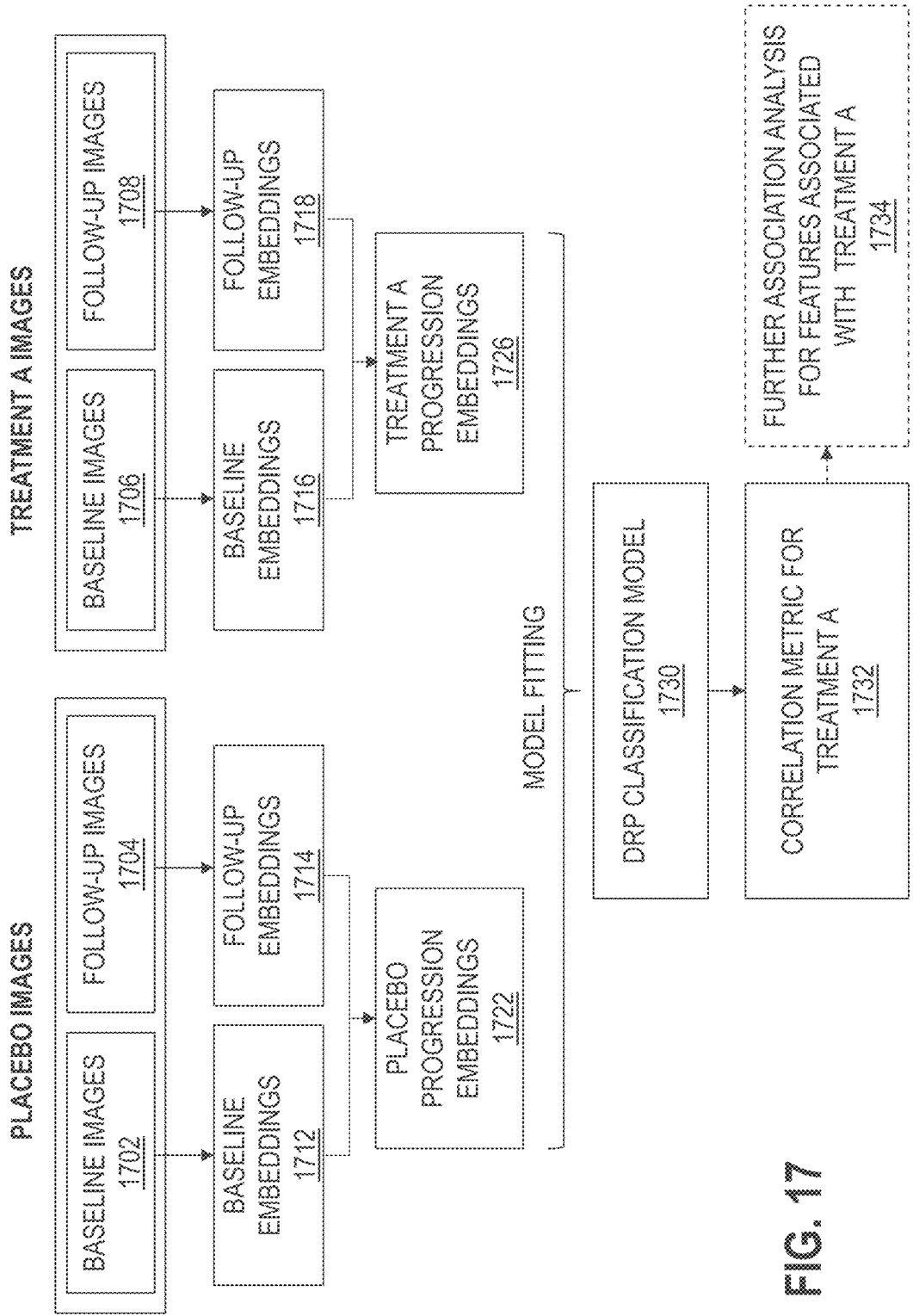
FIG. 17 illustrates an exemplary process for evaluating a treatment with respect to a disease of interest, in accordance with some embodiments.

At block 1602, an exemplary system (e.g., one or more electronic devices) may be configured to obtain a plurality of baseline placebo images of a placebo group of subjects captured before a placebo is administered to the placebo group, and a plurality of follow-up placebo images of the placebo group of subjects captured after the placebo is administered to the placebo group. FIG. 17 illustrates an exemplary process for evaluating a treatment with respect to a disease of interest, in accordance with some embodiments. As shown, the system obtains a plurality of baseline placebo images 1702 of a placebo group of subjects captured before a placebo is administered to the placebo group. The system further obtains a plurality of follow-up placebo images 1704 of the placebo group of subjects captured after the placebo is administered to the placebo group.

At block 1604, the system may be configured to obtain a plurality of placebo progression embeddings based on the plurality of baseline placebo images and the plurality of follow-up placebo images. With reference to FIG. 17, the system may obtain a plurality of baseline placebo embeddings 1712 and a plurality of follow-up placebo embeddings 1714. In some embodiments, baseline placebo embeddings 1712 may be obtained based on baseline placebo images 1702, while follow-up placebo embeddings 1714 may be obtained based on follow-up placebo images 1704. Based on embeddings 1712 and 1714, the system may obtains placebo progression embeddings 1722.

Figure 18A:
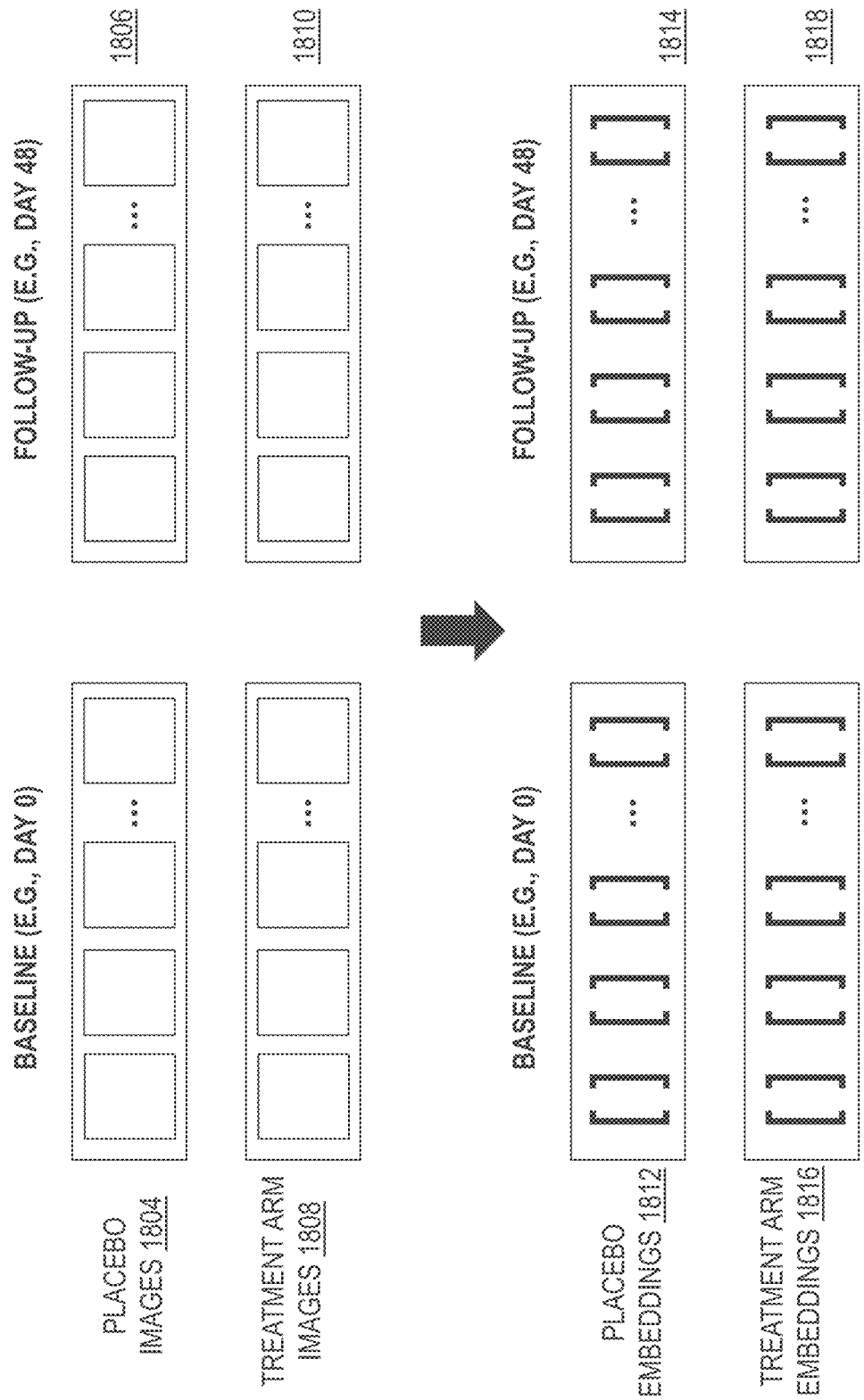
FIGS. 18A-B and 18D illustrate exemplary generation of progression embeddings, in accordance with some embodiments.
Figure 18B:
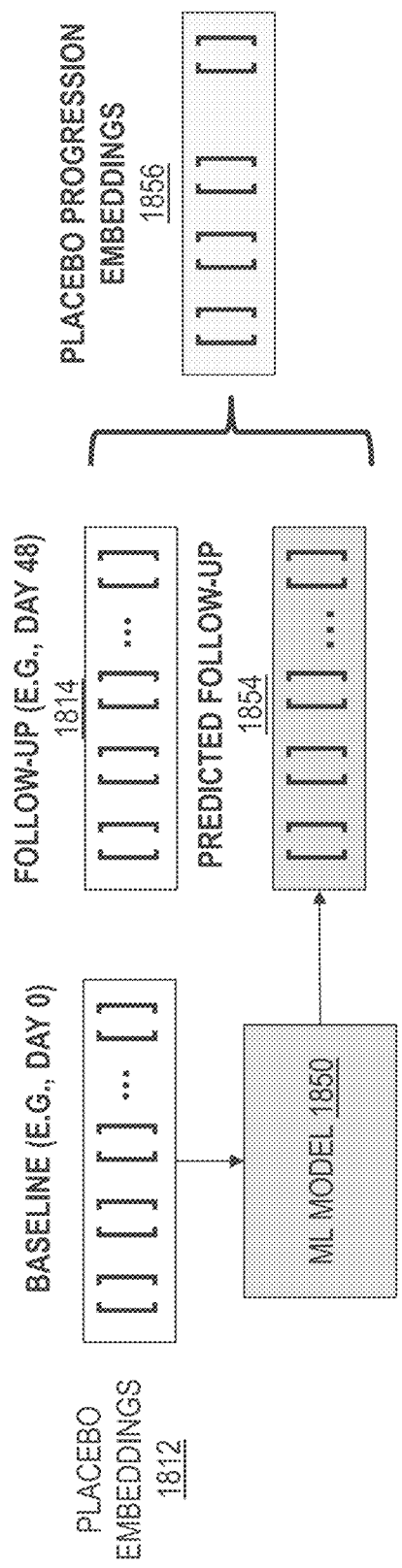

FIGS. 18A-B illustrate an exemplary generation of progression embeddings, in accordance with some embodiments. As shown in FIG. 18A, the system can input a plurality of baseline placebo images 1804 into a trained unsupervised machine-learning model (not depicted) to obtain a plurality of baseline placebo embeddings 1812 in a latent space. Similarly, the system can input a plurality of follow-up placebo images 1806 into the trained unsupervised machine-learning model to obtain a plurality of follow-up placebo embeddings 1814 in the latent space. In some embodiments, the system can input a plurality of baseline treatment images 1808 into the trained unsupervised machine-learning model (not depicted) to obtain a plurality of baseline treatment embeddings 1816 in a latent space. Further still, in some embodiments, the system can input a plurality of follow-up treatment images 1810 into the trained unsupervised machine-learning model to obtain a plurality of follow-up treatment embeddings 1818 in the latent space. In some embodiments, the unsupervised machine-learning model is a contrastive model similar to the model described above with reference to FIGS. 4A-B. In some embodiments, the contrastive model is a SimCLR model. In some embodiments, the unsupervised machine-learning model is a system designed and trained in accordance with those described in connection with FIGS. 8A-B and related figures.

As shown in FIG. 18B, the system can then input baseline placebo embeddings 1812 into a trained machine learning model 1850 to obtain a plurality of predicted follow-up placebo embeddings 1854 in the latent space. The system can then determine the plurality of placebo progression embeddings 1856 by calculating differences between follow-up placebo embeddings 1814 and predicted follow-up placebo embeddings 1854. In some embodiments, for a patient in the placebo group, the system performs a subtraction between the patient's follow-up placebo embedding and the patient's predicted follow-up placebo embedding to obtain the patient's placebo progression embedding.

Figure 18C:
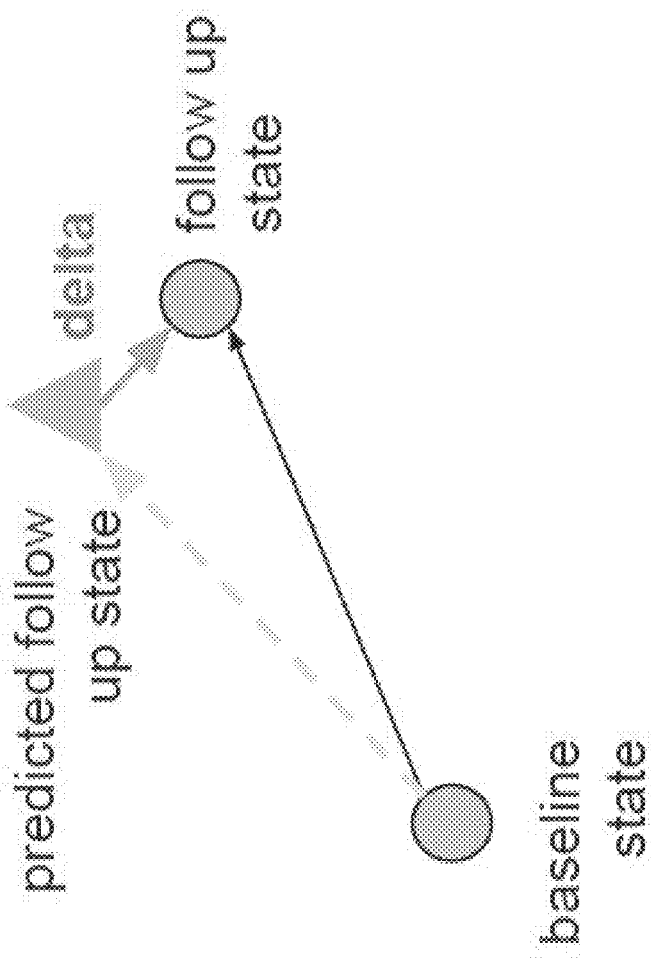
FIG. 18C illustrates an exemplary definition of progression embedding, in accordance with some embodiments.

FIG. 18C illustrates an exemplary definition of progression embedding, in accordance with some embodiments. In some embodiments, each predicted follow-up embedding takes into account whether the patient possesses or is associated with a covariant of interest previously evaluated by a system designed and trained in accordance with those described in connection with FIGS. 8A-B and related figures.

Figure 18D:
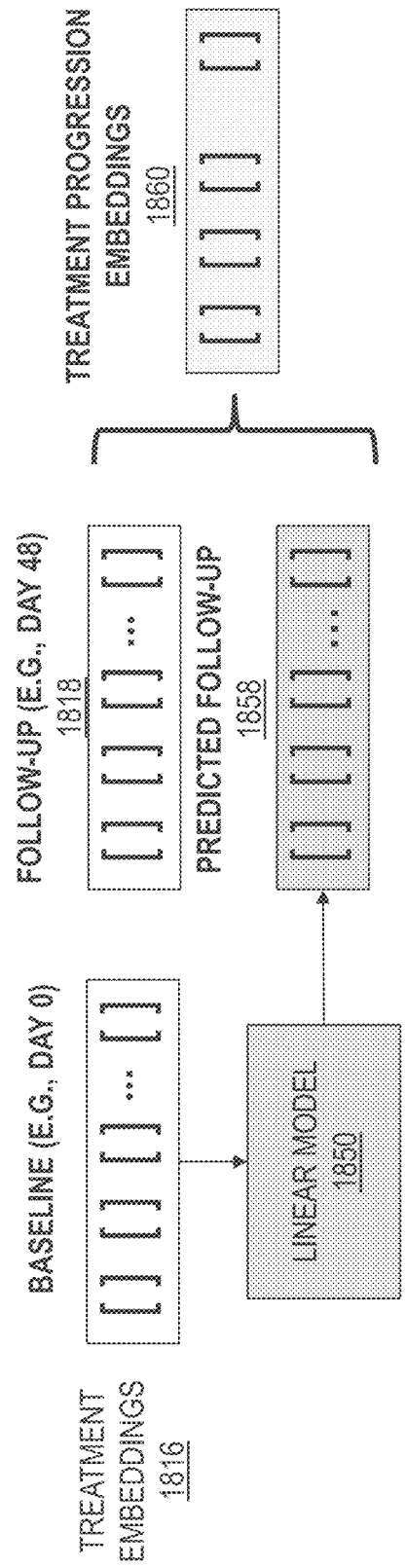

Similarly, as seen with respect to FIG. 18D, the system can input a plurality of baseline treatment embeddings 1816 into a trained machine learning model 1850 to obtain a plurality of predicted follow-up treatment embeddings 1858 in the latent space. The system can then determine a plurality of treatment progression embeddings 1860 by calculating differences between follow-up treatment embeddings 1818 and predicted follow-up treatment embeddings 1858. In some embodiments, for a patient in the treatment group, the system performs a subtraction between the patient's follow-up treatment embedding and the patient's predicted follow-up treatment embedding to obtain the patient's treatment progression embedding.

Figure 19:
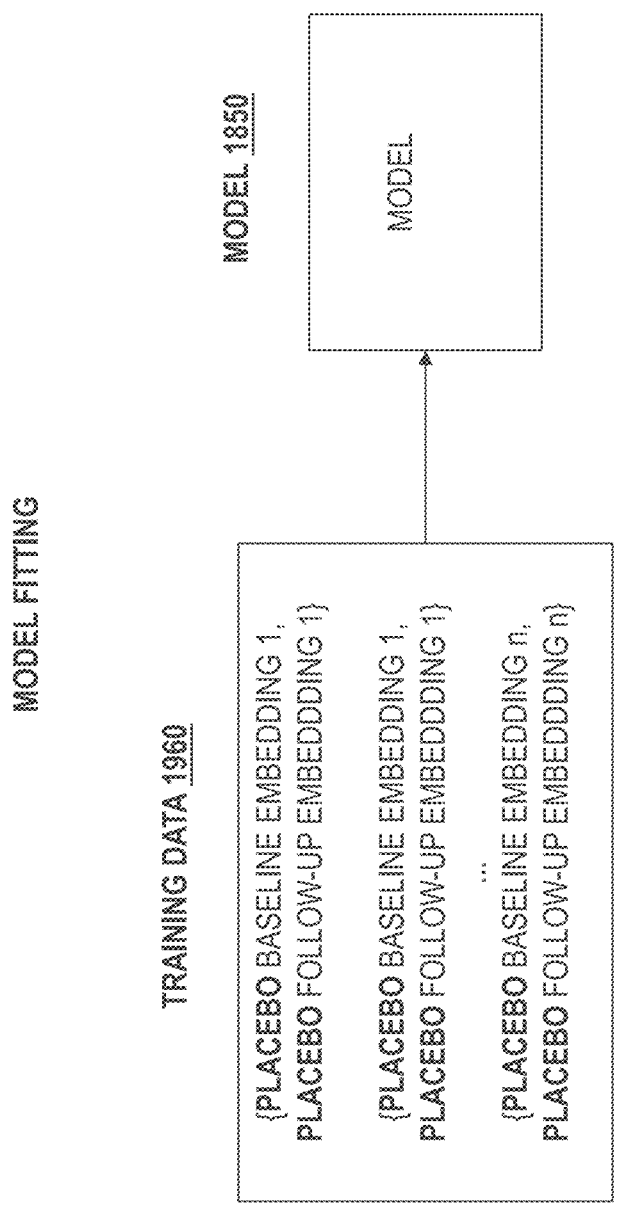
FIG. 19 illustrates an exemplary training process of the linear model, in accordance with some embodiments.

In some embodiments, trained machine learning model 1850 is configured to receive a baseline embedding and output a predicted follow-up embedding. In some embodiments, the trained linear model is a linear mixed model similar to other linear mixed models described herein. FIG. 19 illustrates an exemplary training process of trained machine learning model 1850, in accordance with some embodiments. As shown, trained machine learning model 1850 is trained using training data 1960, which may comprise placebo data. In some embodiments, training data 1960 is obtained from a different placebo group from the one being analyzed in FIGS. 18A-B.

At block 1606, the system may obtain a plurality of baseline treatment images of a treatment group of subjects captured before the treatment is administered to the treatment group and a plurality of follow-up treatment images of the treatment group of subjects captured after the treatment is administered to the treatment group. With reference to FIG. 17, the system may obtain a plurality of baseline treatment images 1706 of a treatment group of subjects captured before the treatment is administered to the treatment group and a plurality of follow-up treatment images 1708 of the treatment group of subjects captured after the treatment is administered to the treatment group At block 1608, the system may obtain a plurality of treatment progression embeddings based on the plurality of baseline treatment images and the plurality of follow-up treatment images. For example, with reference to FIG. 17, the system obtains a plurality of baseline treatment embeddings 1716 and a plurality of follow-up treatment embeddings 1718. In some embodiments, baseline treatment embeddings 1716 are obtained based on baseline treatment images 1706, and follow-up treatment embeddings 1718 are obtained based on follow-up treatment images 1708. Based on embeddings 1716 and 1718, the system may obtain treatment progression embeddings 1726. The generation of progression embeddings is described with reference to FIGS. 18A-C.

At block 1610, the system may generate a classification model for determining whether a patient has received the placebo or the treatment based on the plurality of treatment progression embeddings, wherein outputs of the classification model are indicative of a drug response histological phenotype (DRP). With reference to FIG. 17, the system generates a DRP classification model 1730 based on placebo progression embeddings 1722 and treatment progression embeddings 1726. In some embodiments, the classification model (e.g., DRP classification model 1730) is configured to receive an input progression embedding and output a classification result indicating whether a patient has received the placebo or the treatment. The classification model can be implemented, for example, as a logistic regression model, an artificial neural network model, a random forest model, a naïve Bayes model, etc.

At block 1612, the system may be configured to determine, based on the classification model, a correlation metric 1732 between the treatment and the disease of interest. Correlation metric 1732 may indicate whether the treatment and the progression of the disease of interest are significantly associated. In some embodiments, correlation metric 1732 is a P value.

In some embodiments, the system may be configured to compare correlation metric 1732 with a predefined threshold. In some embodiments, the system may be further configured to identify, based on the comparison, further association analysis for features associated with treatment A 1734.

In some embodiments, the system may be configured to prescribe the treatment (e.g., the treatment performed to the subjects associated with images 1706 and 1708) in a new subject based on the association. For example, if the treatment and the progression of the disease of interest are significantly associated, the same treatment can be prescribed to a new subject having the disease. As another example, if the treatment and the progression of the disease of interest are not significantly associated, the same treatment may not be prescribed to the new subject having the disease.

In some embodiments, the system may be configured to administer the treatment based on the association. For example, if the treatment and the progression of the disease of interest are significantly associated, the same treatment can be administered to a new subject having the disease. As another example, if the treatment and the progression of the disease of interest are not significantly associated, the same treatment may not be administered to the new subject having the disease.

In some embodiments, the system may be configured to adjust the treatment based on the association. For example, if the treatment and the progression of the disease of interest are significantly associated, the treatment may be increased. As another example, if the treatment and the progression of the disease of interest are not significantly associated, the treatment may be reduced or stopped.

In some embodiments, the system may be configured to provide a medical recommendation based on the association. In some embodiments, the system may be configured to generate a report based on the association. In some embodiments, if the treatment and the progression of the disease of interest are significantly associated, the system can further study the treatment, for example, as described in FIG. 21.

In some embodiments, the disease of interest is non-alcoholic steatohepatitis (NASH).

In an exemplary implementation, two clinical trials have been conducted. The smaller clinical trial obtains baseline and follow-up liver biopsy imaging data and pathologist-assigned scores associated with the imaging data. In particular, the smaller clinical trial is a NASH Ph2 trial with around 380 samples, and liver biopsy imaging data are obtained at baseline and 48 weeks follow-up. The larger clinical trial obtains aligned baseline and follow-up liver biopsy imaging data and associated pathologist scores. In particular, the larger clinical trial comprises two NASH Ph3 trials with around 1,600 samples, and liver biopsy imaging data are obtained at baseline and 48 weeks follow-up.

The system then obtains biopsy embeddings from all H&E-stained liver biopsy images (e.g., baseline placebo embeddings 1712, follow-up placebo embeddings 1714, baseline treatment embeddings 1716, and follow-up treatment embeddings 1718 in FIG. 17) through the unsupervised learning procedure.

The system further obtains progression embeddings (e.g., placebo progression embeddings 1722, treatment progression embeddings 1726). First, the system trains a phenotypic prediction model (e.g., trained machine learning model 1850) to predict every dimension of the biopsy embedding at follow-up (i.e., week 48) from a biopsy embedding at baseline solely considering patients in the placebo group of the larger trial. Trained machine learning model 1850 can be configured in a similar manner to embedding-score prediction model 312 (which may also be a linear model) in FIG. 3A. In some embodiments, machine learning model 1850 may be a linear regression model, such as a linear mixed model.

After the phenotypic prediction model is trained, the system may use the trained phenotypic prediction model to predict follow-up liver state embeddings under placebo given baseline liver state embedding in patients in the smaller trial. These predicted follow-up embeddings capture the expected histological state at follow-up in placebo patients. The system defines progression embeddings as the difference between the observed follow-up embeddings and the predicted follow-up embedding from the previous step. As defined, the progression embeddings describe histological differences in patients from the smaller trial between their histological state at follow-up versus the expected histological state in placebo patients.

For each treatment arm, the system may train a treatment-specific model (e.g., DRP classification model 1730) to classify patients from placebo and the treatment arm from progression embeddings in the small trial. The predictions from this model provide a measure for each patient of the Drug Response histological Phenotype (DRP) at follow-up. In some embodiments, the input of the classification model is a progression embedding (e.g., placebo progression embeddings 1856, 1860). In some embodiments, the output of the classification model is a binary indicator for each patient indicating whether that patient is in the treatment or placebo group. The DRP classification can be configured in a similar manner to embedding-score prediction model 312 in FIG. 3A.

Statistical significance of the predicted DRP can be assessed, for example, using the permutation procedure described herein. For example, the system can calculate a correlation metric for the model. In some embodiments, the correlation metric is a P value. The P value can be obtained through a permutation procedure where the log likelihood ratio (LLR) statistic from the real data is compared to LLRs obtained when permuting the individuals in the embedding matrix (LLRs from null model). In some embodiments, the P value is defined as the fraction of LLRs under permutations that are greater than the real data LLR, as described above.

The correlation metric for each genetic variant can be compared against a predefined threshold to determine whether there is an association between the genetic variant and the embeddings. In one exemplary implementation, the system uses a Bonferroni-adjusted P value threshold of 0.05 to define significant treatment histological effects and assess whether the treatment has an effect on progression embeddings. In some embodiments, only treatments with significant P values are further studied, for example, using the process 2000 in FIG. 20.

In some embodiments, when analyzing a treatment, the effect of the treatment may be analyzed directly using follow-up embeddings. In such cases, baseline embeddings/images may be excluded from the analysis.

Figure 20:
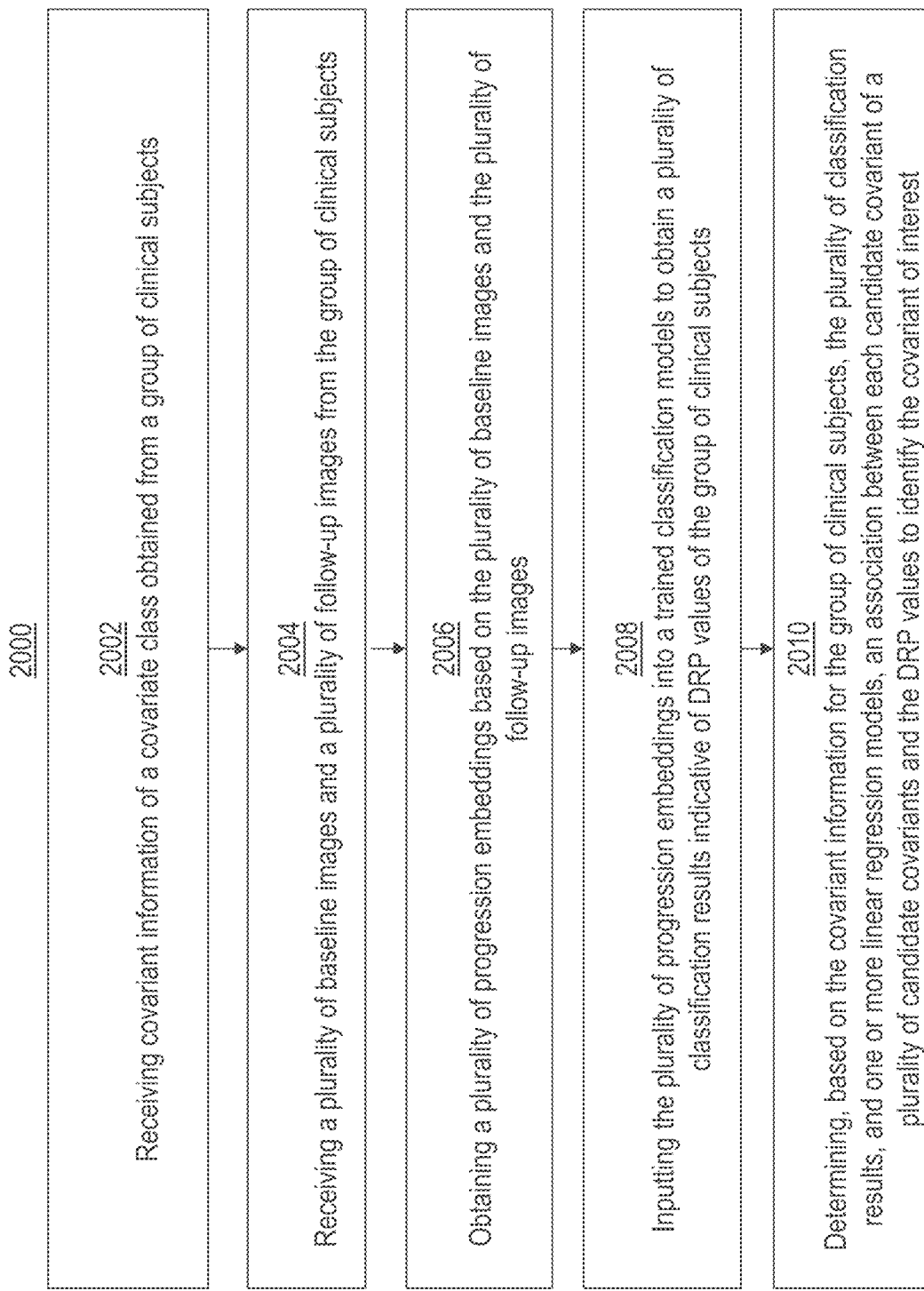
FIG. 20 illustrates an exemplary method of identifying a covariant of interest with respect to drug response histological phenotype (DRP) of a treatment, in accordance with some embodiments.

FIG. 20 illustrates an exemplary method of identifying a covariant of interest with respect to drug response histological phenotype (DRP) of a treatment. The imputation of DRP can be performed using clinical trial datasets as long as the progression embeddings are available. Significant associations between DRP and molecular data (e.g., expression and genetics) can be retrieved through an association test. Association with expression identifies genes that could not be detected in a placebo-vs-drug differential expression analysis. Association with genetics identifies a candidate target gene for the disease of interest (e.g., NASH).

Process 2000 is performed, for example, using one or more electronic devices implementing a software platform. In some examples, process 2000 is performed using a client-server system, and the blocks of process 2000 are divided up in any manner between the server and one or more client devices. Thus, while portions of process 2000 are described herein as being performed by particular devices of a client-server system, it will be appreciated that process 2000 is not so limited. In other examples, process 2000 is performed using only a client device or only multiple client devices. In process 2000, some blocks are, optionally, combined, the order of some blocks is, optionally, changed, and some blocks are, optionally, omitted. In some examples, additional steps may be performed in combination with the process 2000. Accordingly, the operations as illustrated (and described in greater detail below) are exemplary by nature and, as such, should not be viewed as limiting.

At block 2002, an exemplary system (e.g., one or more electronic devices) may be configured to receive covariant information of a covariate class obtained from a group of clinical subjects. In some embodiments, the covariate class comprises demographic information, clinical covariates, or genomic data. At block 2004, the system may be configured to receive a plurality of baseline images and a plurality of follow-up images from the group of clinical subjects.

Figure 21:
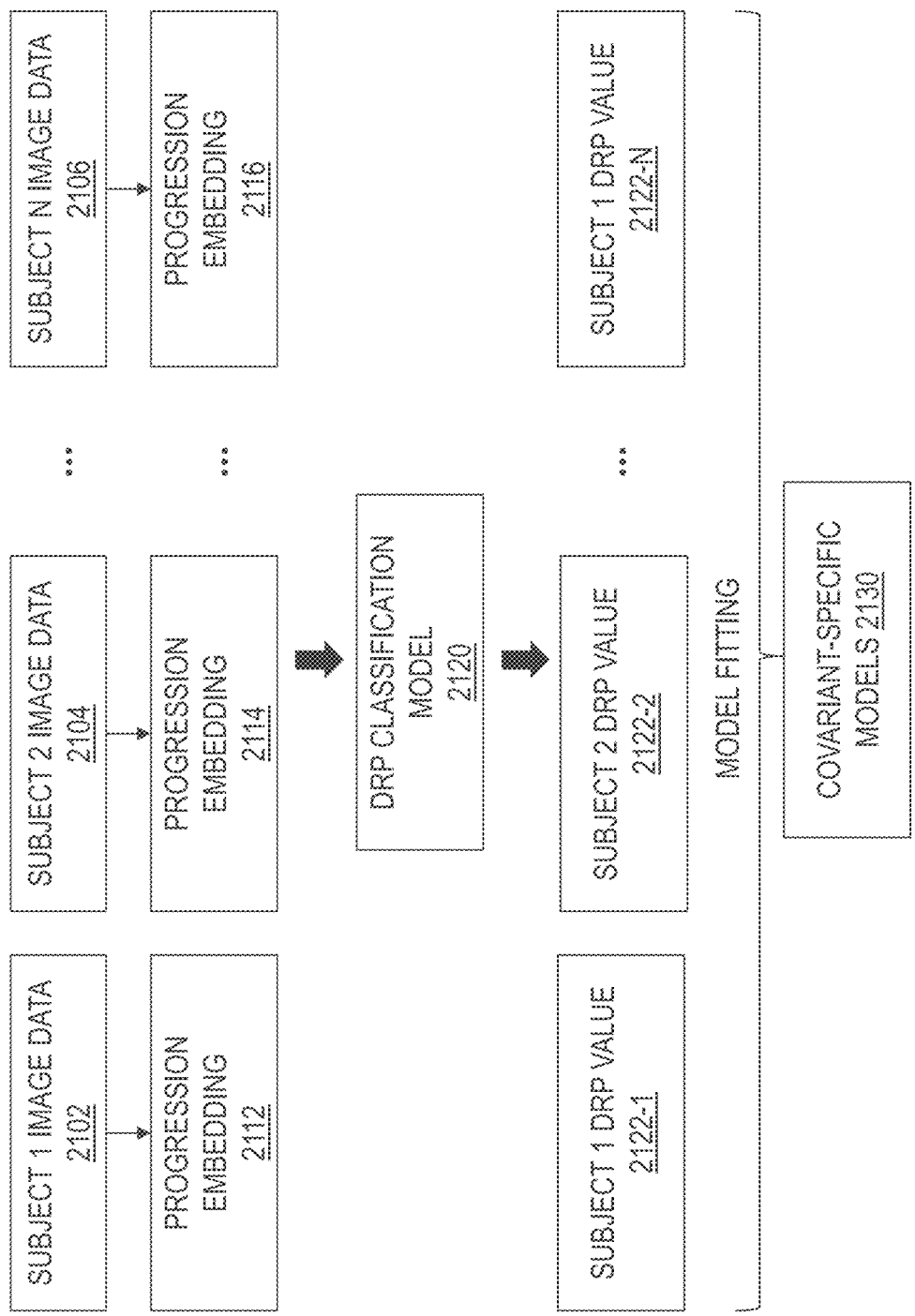
FIG. 21 illustrates an exemplary method of identifying a covariant of interest with respect to drug response phenotype (DRP) of a treatment, in accordance with some embodiments.

The data obtained in blocks 2002 and 2004 can be data of subjects in the same treatment group. The treatment group can be identified, for example, as described herein with reference to FIGS. 16-19 and 23. With reference to FIG. 21, the system can receive image data 2102 for subject 1, image data 2104 for subject 2, . . . , and image data 2106 for subject N. Subjects 1-N may belong to the same treatment group that receives the same treatment. In some embodiments, the treatment group has received the treatment of interest identified, for example, as described herein with reference to FIGS. 16-19 and 23 (e.g., treatment A if the correlation metric 1732 meets a predefined threshold).

At block 2006, the system may be configured to obtain a plurality of progression embeddings based on the plurality of baseline images and the plurality of follow-up images. As shown in FIG. 21, the system may obtain progression embeddings 2112, 2114, . . . , and 2116. Generation of progression embeddings are described herein, for example, with reference to FIGS. 18A-C. In some embodiments, obtaining the plurality of progression embeddings based on the plurality of baseline images and the plurality of follow-up images comprises: inputting the plurality of baseline images into a trained unsupervised machine-learning model to obtain a plurality of baseline embeddings in a latent space; inputting the plurality of follow-up images into the trained unsupervised machine-learning model to obtain a plurality of follow-up embeddings in the latent space; inputting the plurality of baseline embeddings into a trained linear model to obtain a plurality of predicted follow-up embeddings in the latent space; determining the plurality of progression embeddings by calculating differences between the plurality of follow-up embeddings and the plurality of predicted follow-up embeddings.

In some embodiments, the unsupervised machine-learning model is a contrastive model.

In some embodiments, the contrastive model is a SimCLR model.

In some embodiments, the trained linear model is configured to receive a baseline embedding and output a predicted follow-up embedding.

In some embodiments, the trained linear model is a linear mixed model.

At block 2008, the system may be configured to input the plurality of progression embeddings into a trained classification model to obtain a plurality of classification results indicative of DRP values of the group of clinical subjects. As shown in FIG. 21, each progression embedding can be inputted into a DRP classification model 2120. For example, progression embedding 2112, generated based on image data 2102, can be input into DRP classification model 2120 to obtain the DRP value for subject 1; progression embedding 2114, generated based on image data 2104, can be input into DRP classification model 2120 to obtain the DRP value for subject 2; and progression embedding 2116, generated based on image data 2106, can be input into DRP classification model 2120 to obtain the DRP value for a given subject of subjects 1-N. In some embodiments, the trained classification model is configured to receive an input progression embedding and determine whether a patient has received the placebo or the treatment. The classification model can be the same or similar to trained machine learning model 1850 in FIGS. 18B-C. Thus, the system imputes drug response phenotype (DRP) as the predictions from a model from progression embeddings to the treatment (placebo vs drug). This imputation can be performed in other clinical trial datasets as long as the progression embeddings are available.

At block 2010, the system may be configured to determine, based on the covariant information for the group of clinical subjects, the plurality of classification results, and one or more linear regression models, an association between each candidate covariant of a plurality of candidate covariants and the DRP values (e.g., DRP values 2122-1-2122-N) to identify the covariant of interest. In other words, the system may identify significant associations between DRP and molecular data (expression and genetics). Association with expression identifies genes that could not be detected in a placebo-vs-drug differential expression analysis. In some cases, the analysis of the DRP can identify a correlated set of genes as case control of the true placebo-vs-drug differential expression analysis. In some cases, the analysis of DRP can identify a larger set of genes due to the analysis of a larger cohort, which can help interpret correlates of the DRP.

In some embodiments, identifying the covariant of interest comprises generating a covariant-specific model 2130, for each candidate covariant of the plurality of candidate covariants, based on the DRP values and the covariant information of the group of clinical subjects. In some embodiments, some or all of covariant-specific models 2130 can be a linear mixed model similar to those described herein. The system can generate covariant-specific models (e.g., 100,000 models, 1 million models, 10 million models) for all candidate covariants (e.g., 100,000 candidates, 1 million candidates, 10 million candidates). Each model can be evaluated to determine if there is a significant association between each candidate covariant and the DRP to identify one or more covariants of interest.

In some embodiments, the system can determine a correlation metric based on the model. The correlation metric indicates whether the candidate covariant and the DRP values are significantly associated. In some embodiments, the correlation metric is a P value. In some embodiments, the correlation metric may be compared against a predefined threshold to determine if the candidate covariant is the covariant of interest.

In some embodiments, the plurality of candidate covariants comprises a plurality of candidate missense variants. In an exemplary implementation, a progression GWAS of the ACCi+FXRa DRP in a clinical trial was performed, focusing on 27,270 missense variants (MAF>1%). The analysis can identify missense loci genes.

Figure 27:
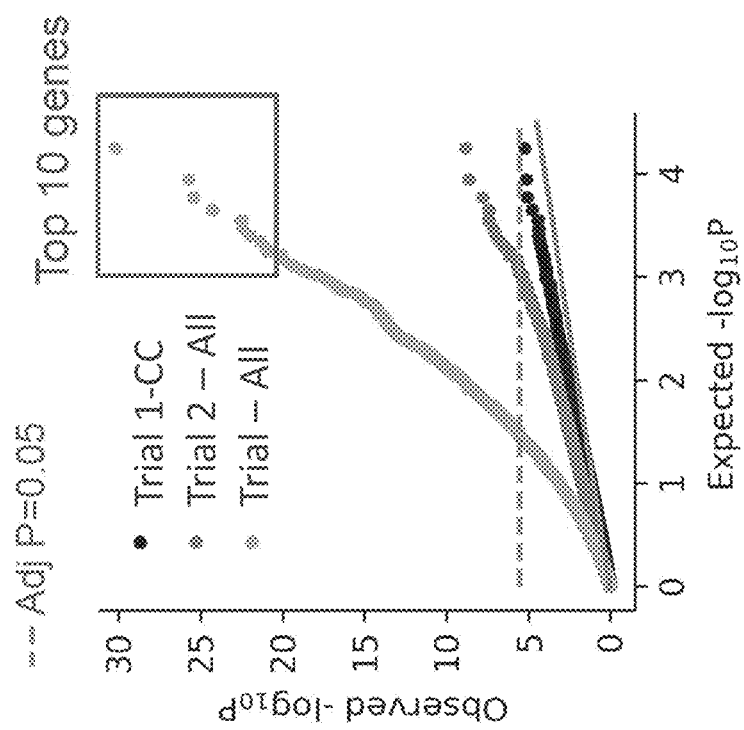
FIG. 27 illustrates association studies between DRP and expression, in accordance with some embodiments.

In some embodiments, the plurality of candidate covariants comprises a plurality of candidate genes. In an exemplary implementation, association between expression and DRP in various clinical trials identified thousands of associated genes, as shown in FIG. 27.

In some embodiments, the identified covariant of interest can be used to diagnose a disease of interest in a new subject. In some embodiments, a treatment may be developed based on the identified covariant of interest.

In some embodiments, the treatment may be administered, adjusted, and/or applied based on the identified covariant of interest.

In some embodiments, a medical recommendation may be provided (or solicited) based on the identified covariant of interest.

In some embodiments, a biological target may be identified based on the identified covariant of interest.

In some embodiments, the plurality of medical images include biopsy images.

In an exemplary implementation, two clinical trials have been conducted. The smaller clinical trial obtains baseline and follow-up liver biopsy imaging data and pathologist-assigned scores associated with the imaging data. In particular, the smaller clinical trial is a NASH Ph2 trial with around 380 samples, and liver biopsy imaging data are obtained at baseline and 48 weeks follow-up. The larger clinical trial obtains aligned baseline and follow-up liver biopsy imaging data and associated pathologist scores. In particular, the larger clinical trial comprises two NASH Ph3 trials with around 1,600 samples, and liver biopsy imaging data are obtained at baseline and 48 weeks follow-up.

As described above, for each treatment arm, the system may be configured to train a treatment-specific model (e.g., DRP classification model 1730) to classify patients from the placebo and treatment arm from progression embeddings in the small trial. The predictions from this model provide a measure for each patient of the Drug Response histological Phenotype (DRP) at follow-up. In some embodiments, the input of the classification model is a progression embedding. The output of the classification model is a binary indicator for whether each patient is in the treatment or placebo group. The DRP classification can be configured in a similar manner to embedding-score prediction model 312 in FIG. 3A.

In some embodiments, the system may be configured to use the trained DRP classification model to predict the DRP values in the large trials. The system can then use the bigger trial to analyze DRP together with other data layers to address specific questions, as demonstrated by two examples below.

In one example, the system analyzes DRP and gene expression in the large clinical trial to identify genes and pathways associated with the treatment. First, the system tests for associations between the DRP values and gene expression using a linear model association procedure described with respect to model 316 in FIG. 3B. For example, the system can fit a gene-specific model that receives a gene value and outputs a DRP value. A P value can be determined for the model. The system then performs pathway enrichment analysis using existing approaches (e.g., GSEA, which takes as input a gene list ranked by P value from association with DRP from the previous step and pathway annotation from external sources (e.g., gene ontology)). In an exemplary implementation, this procedure yields correlated association statistics to a direct differential expression analysis between treatment and placebo arms. Additionally, a much larger set of genes are identified as significantly associated with the DRP in the large study than are associated with the treatment-placebo differential expression analysis.

In some embodiments, gene expression may be imputed. For example, a machine learning model, such as a trained linear regression model, may be fit to image embeddings of a biological sample. The machine learning model may be trained to predict tissue RNA-sequence measurements based on imaging embeddings of patient tissue samples from a clinical trial. In some embodiments, the same or similar machine learning model (e.g., the same or similar linear regression model) may be applied to imaging embeddings of patient tissue samples from another clinical trial. For example, the imaging embeddings of the patients from the other clinical trial may not have associated RNA-sequence data. An association between the predicted RNA-sequence measurements and covariates of interest, such as a treatment, may be assessed to help interpret correlates of a covariate.

In another example, the system performs genetic analysis of the DRP to identify candidate target genes that affect the same histological phenotype affected by the drug (thus likely affecting the same pathways). Specifically, the system tests for associations between the DRP and missense variants using the linear model association procedure described with respect to model 316 in FIG. 3B, and controlling for age, sex, genotype PCs, and treatment group as covariates. For example, the variant-specific model is configured to receive a missense variant value and output a DRP value. This analysis can identify a missense variant in a gene associated with the DRP. In some cases, the association can be significant after multiple hypothesis testing correction.

FIG. 22 illustrates an exemplary method of evaluating a treatment with respect to progression of a disease of interest, in accordance with some embodiments. In FIG. 22, the disease progression is quantified by continuous medical diagnosis scores. In exemplary implementations, we analyze disease progression by performing association tests between covariates of interest and progression scores, controlling for both discrete and continuous baseline disease scores in addition to other relevant covariates. The continuous scores enable a more precise definition of disease progression, for example, with respect to, empowering longitudinal expression analysis (e.g., FIG. 26A), genetic association studies (e.g., FIG. 26B), and association studies of treatment responses. In these examples, we find that analysis of the continuous disease scores frequently recapitulates associations identified through the analysis of discrete pathologist-assigned disease scores and identifies additional associations that are not identified with the pathologist scores.

This procedure retrieves drug effects on continuous scores that could not be detected using pathologist-assigned, discrete scores. Process 2200 is performed, for example, using one or more electronic devices implementing a software platform. In some examples, process 2200 is performed using a client-server system, and the blocks of process 2200 are divided up in any manner between the server and one or more client devices. Thus, while portions of process 2200 are described herein as being performed by particular devices of a client-server system, it will be appreciated that process 2200 is not so limited. In other examples, process 2200 is performed using only a client device or only multiple client devices. In process 2200, some blocks are, optionally, combined, the order of some blocks is, optionally, changed, and some blocks are, optionally, omitted. In some examples, additional steps may be performed in combination with the process 2200. Accordingly, the operations as illustrated (and described in greater detail below) are exemplary by nature and, as such, should not be viewed as limiting.

Figure 23:
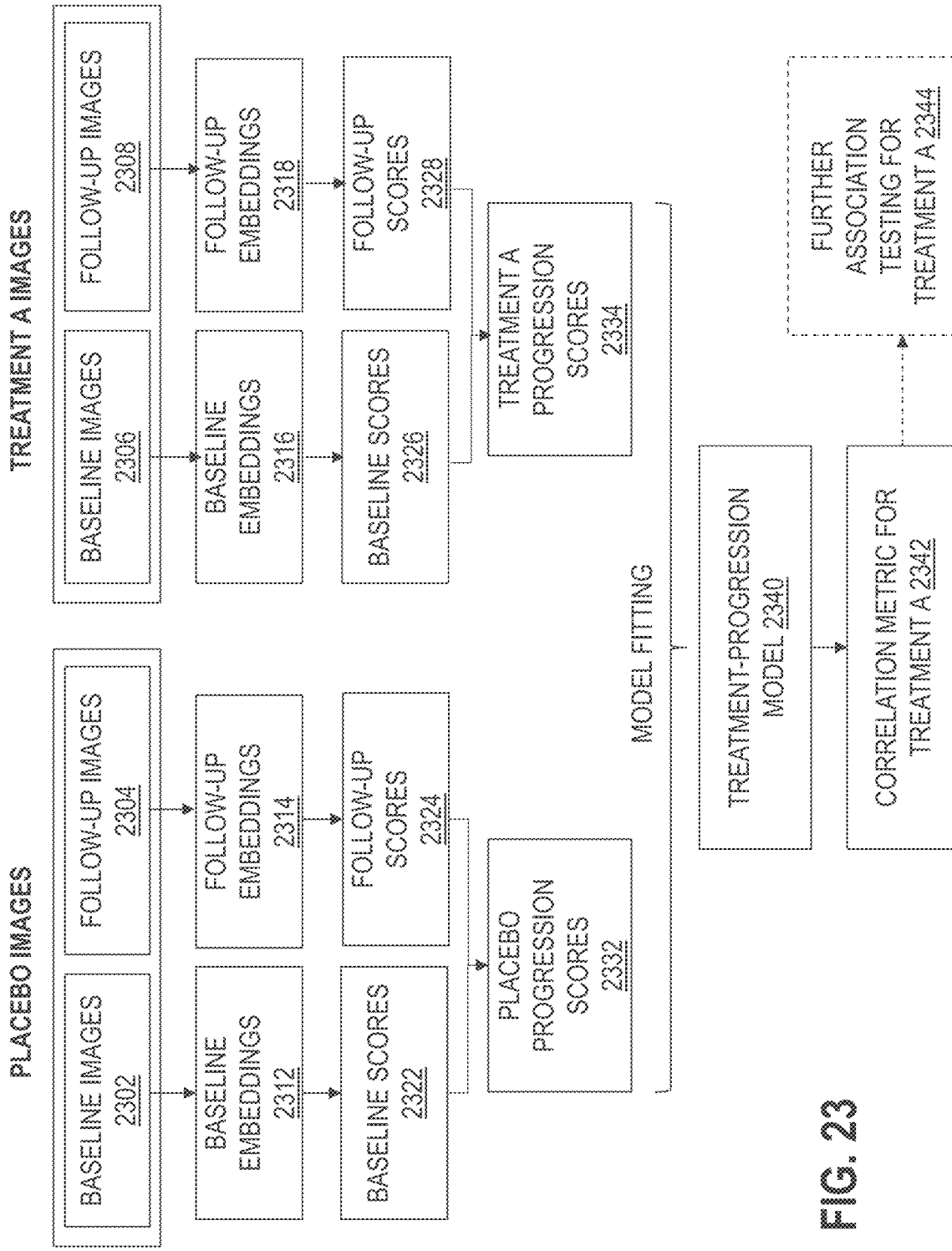
FIG. 23 illustrates an exemplary method of evaluating a treatment with respect to progression of a disease of interest, in accordance with some embodiments.

At block 2202, an exemplary system (e.g., one or more electronic devices) may be configured to obtain medical images comprising: (a) a plurality of baseline placebo images of a placebo group of subjects captured before a placebo is administered to the placebo group, (b) a plurality of follow-up placebo images of the placebo group of subjects captured after the placebo is administered to the placebo group, (c) a plurality of baseline treatment images of a treatment group of subjects captured before the treatment is administered to the treatment group, and (d) a plurality of follow-up treatment images of the treatment group of subjects captured after the treatment is administered to the treatment group. With reference to FIG. 23, the system obtains baseline placebo images 2302, follow-up placebo images 2304, baseline treatment images 2306, and follow-up treatment images 2308.

At block 2204, the system may be configured to input the medical images into a trained unsupervised machine-learning model to obtain a plurality of embeddings, each embedding corresponding to a phenotypic state relative to the disease of interest reflected in one or more of the medical images. In some embodiments, inputting the medical images into a trained unsupervised machine-learning model to obtain the plurality of embeddings comprises: inputting (a) a plurality of baseline placebo images of a placebo group of subjects captured before a placebo is administered to the placebo group into the trained unsupervised machine-learning model to obtain a plurality of baseline placebo embeddings; inputting (b) a plurality of follow-up placebo images of the placebo group of subjects captured after the placebo is administered to the placebo group into the trained unsupervised machine-learning model to obtain a plurality of follow-up placebo embeddings; inputting (c) a plurality of baseline treatment images of a treatment group of subjects captured before the treatment is administered to the treatment group into a trained unsupervised machine-learning model to obtain a plurality of baseline treatment embeddings; inputting (d) a plurality of follow-up treatment images of the treatment group of subjects captured after the treatment is administered to the treatment group into the trained unsupervised machine-learning model to obtain a plurality of follow-up treatment embeddings.

With reference to FIG. 23, the system may be configured to input: baseline placebo images 2302 to obtain baseline placebo embeddings 2312, follow-up placebo images 2304 to obtain follow-up placebo embeddings 2314, baseline treatment images 2306 to obtain baseline treatment embeddings 2316, and follow-up treatment images 2308 to obtain follow-up treatment embeddings 2318. The unsupervised machine-learning model used to generate the embeddings can be similar to the model described with reference to FIGS. 4A and 4B. In some embodiments, the unsupervised machine-learning model is a contrastive model. In some embodiments, the contrastive model is a SimCLR model.

At block 2206, the system may be configured to input the plurality of embeddings into a trained linear regression model to obtain a plurality of predicted continuous medical diagnosis scores, each predicted continuous medical diagnosis score may indicate a state of the disease of interest. In some embodiments, inputting the plurality of embeddings into the trained linear regression model comprises: inputting the plurality of baseline placebo embeddings into the trained linear model to obtain a plurality of baseline placebo scores 2322; inputting the plurality of follow-up placebo embeddings into the trained linear model to obtain a plurality of follow-up placebo scores 2324; inputting the plurality of baseline treatment embeddings into the trained linear model to obtain a plurality of baseline treatment scores 2326; and inputting the plurality of follow-up treatment embeddings into the trained linear model to obtain a plurality of follow-up treatment scores 2328.

In some embodiments, the linear regression model is a linear mixed model similar to the embedding-score prediction model 312 described with reference to FIG. 3A. In some embodiments, the linear regression model is fit based on a plurality of assigned medical diagnosis scores. In some embodiments, the plurality of assigned medical diagnosis scores are provided by one or more medical practitioners. In some embodiments, each assigned medical diagnosis score of the plurality of assigned medical diagnosis scores is selected from a set of predefined values. In some embodiments, the plurality of predicted medical diagnosis scores is a plurality of predicted fibrosis scores, a plurality of predicted lobular inflammation scores, or a plurality of predicted steatosis scores.

At block 2208, the system determines a plurality of placebo progression scores 2332 and a plurality of treatment progression scores 2334 based on the predicted continuous medical diagnosis scores. In some embodiments, determining placebo progression scores 2332 and treatment progression scores 2334 comprises: determining differences between baseline placebo scores 2322 and follow-up placebo scores 2324 to determine placebo progression scores 2332; and determining differences between baseline treatment scores 2326 and follow-up treatment scores 2328 to determine treatment progression scores 2334. For example, for a patient in the placebo group, the placebo progression score is the difference between the patient's baseline placebo score and follow-up placebo score. For example, for a patient in the treatment group, the treatment progression score is the difference between the patient's baseline treatment score and follow-up treatment score.

In some embodiments, determining the plurality of placebo progression scores and the plurality of treatment progression scores comprises: determining, for each subject in the placebo group, a slope of a linear model fitted at least based on a baseline placebo score and a follow-up placebo score of the subject in the placebo group; and determining, for each subject in the treatment group, a slope of a linear model fitted at least based on a baseline placebo score and a follow-up placebo score of the subject in the treatment group. For example, for a patient, the system can obtain the patient's medical diagnosis scores over time (including the baseline score and the follow-up score) and fit a linear model configured to receive a dosage (or time of treatment) and predict a medical diagnosis score. The progression score for the patient can be the slope of the linear model.

At block 2210, the system may be configured to associate the plurality of placebo progression scores and the plurality of treatment progression scores with the treatment; and determine, based on the association, a correlation metric between the plurality of disease progression scores and the treatment. In some embodiments, associating the plurality of placebo progression scores and the plurality of treatment progression scores with the treatment comprises generating a model configured to receive an indication of whether a patient received the treatment and output a predicted disease progression score. As shown in FIG. 23, the system may be configured to generate the model 2340 and calculate a correlation metric 2342. In some embodiments, the model is a linear mixed model as described herein.

In some embodiments, the correlation metric is a P value of the model. The correlation metric indicates whether there is a significant association between the treatment and the progression of the disease.

In some embodiments, further association testing 2344 for a given treatment may be performed. For example, the correlation metric may be compared with a predefined threshold. In some embodiments, an association between the treatment and the disease of interest may be identified based on the comparison. In some embodiments, the system may be further configured to prescribe the treatment in a new subject based on the association. For example, if the treatment and the progression of the disease of interest are significantly associated, the same treatment can be prescribed to the new subject having the disease. As another example, if the treatment and the progression of the disease of interest are not significantly associated, the same treatment would not be prescribed to the new subject having the disease.

In some embodiments, the system may be further configured to administer the treatment based on the association. For example, if the treatment and the progression of the disease of interest are significantly associated, the same treatment can be administered to the new subject having the disease. As another example, if the treatment and the progression of the disease of interest are not significantly associated, the same treatment would not be administered to the new subject having the disease.

In some embodiments, the system may be further configured to adjust the treatment based on the association. For example, if the treatment and the progression of the disease of interest are significantly associated, the treatment may be increased. As another example, if the treatment and the progression of the disease of interest are not significantly associated, the treatment may be reduced or stopped.

In some embodiments, a medical recommendation may be provided based on the association. In some embodiments, if the treatment and the progression of the disease of interest are significantly associated, the system can further study the treatment, for example, as described in FIG. 21. In some embodiments, the disease of interest is non-alcoholic steatohepatitis (NASH).

Figure 24:
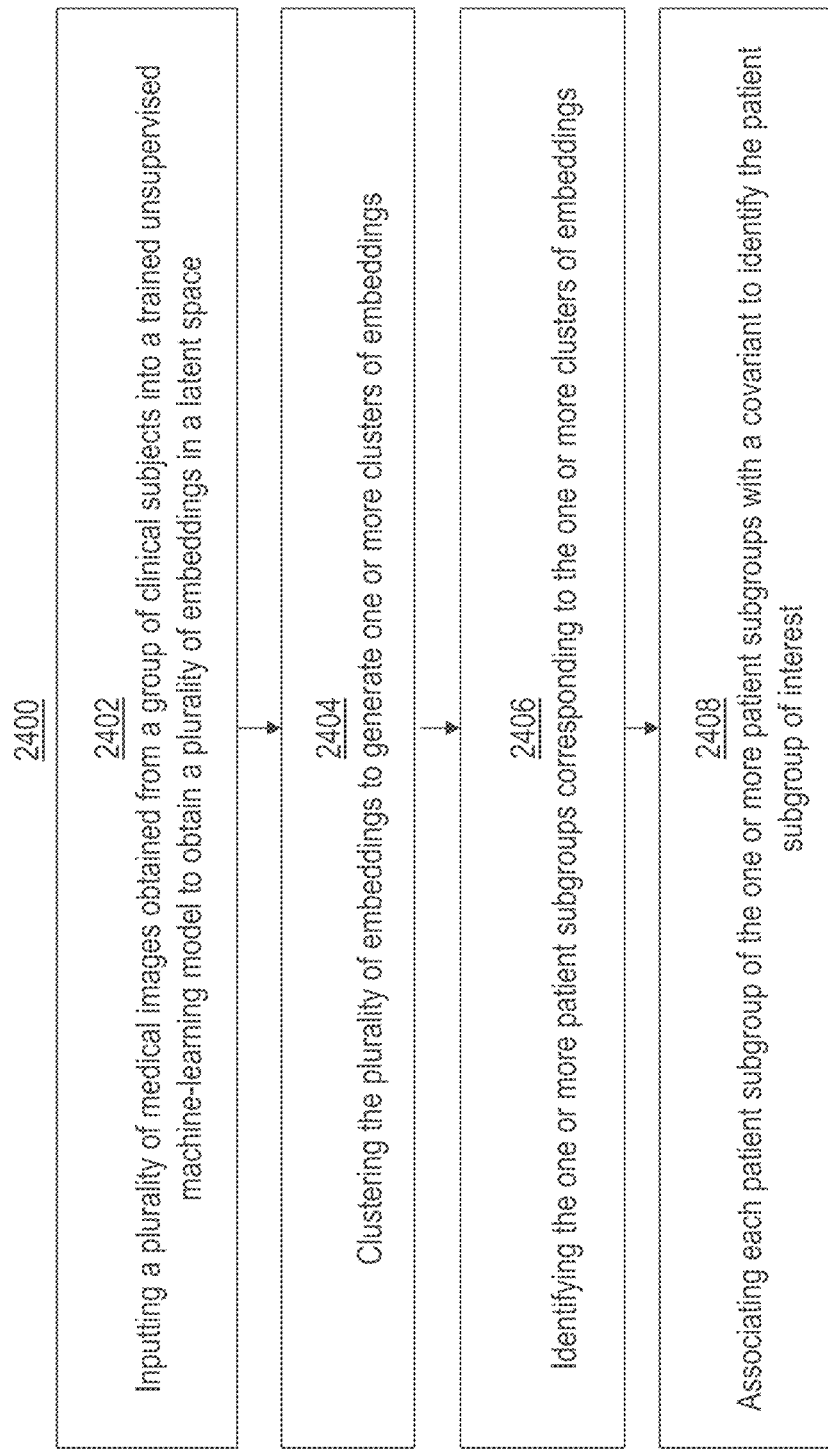
FIG. 24 illustrates an exemplary method of identifying a patient subgroup of interest, in accordance with some embodiments.

FIG. 24 illustrates an exemplary method of identifying a patient subgroup of interest, in accordance with some embodiments. The system may be configured to obtain embeddings from patient image data and identify clusters of embeddings as subgroups of patients. Significant associations between the patient cluster identity and disease biomarkers, genetic variants and expression levels are retrieved from an association test. This procedure retrieves patient segments and associated clinical labels and molecular drivers that help to characterize each patient segment.

Process 2400 is performed, for example, using one or more electronic devices implementing a software platform. In some examples, process 2400 is performed using a client-server system, and the blocks of process 2400 are divided up in any manner between the server and one or more client devices. Thus, while portions of process 2400 are described herein as being performed by particular devices of a client-server system, it will be appreciated that process 2400 is not so limited. In other examples, process 2400 is performed using only a client device or only multiple client devices. In process 2400, some blocks are, optionally, combined, the order of some blocks is, optionally, changed, and some blocks are, optionally, omitted. In some examples, additional steps may be performed in combination with the process 2400. Accordingly, the operations as illustrated (and described in greater detail below) are exemplary by nature and, as such, should not be viewed as limiting.

At block 2402, the system may be configured to input a plurality of medical images obtained from a group of clinical subjects into a trained unsupervised machine-learning model to obtain a plurality of embeddings in a latent space. At block 2404, the system may be configured to cluster the plurality of embeddings to generate one or more clusters of embeddings. At block 2406, the system may be configured to identify the one or more patient subgroups corresponding to the one or more clusters of embeddings.

At block 2408, the system may be configured to associate each patient subgroup of the one or more patient subgroups with a covariant to identify the patient subgroup of interest. Specifically, the system can perform two types of analyses. First, the system can characterize each patient subgroup by determining if there is a significant association between the patient subgroup and a covariant (e.g., disease biomarkers, genetic variants and expression levels) from an association test. This way, the system can obtain, for an identified patient subgroup, the associated clinical labels and molecular drivers that characterize the patient subgroup. In some embodiments, the association test involves generating a model that receives an input indicative of whether a patient belongs to the patient subgroup (e.g., 0 if the patient does not belong and 1 if the patient belongs to the subgroup) and outputs a covariant value. Second, the system can characterize effects of covariants (e.g., treatment or genotype) within each patient subgroups. For example, the system can perform analyses (e.g., genetic association studies and association between treatment and clinical progression) only considering patients within a subgroup. The association test involves generating a model using only data of patients within the subgroup.

In some embodiments, the unsupervised machine-learning model is a contrastive model.

In some embodiments, the contrastive model is a SimCLR model.

In some embodiments, the covariant is a treatment of interest and wherein the patient subgroup of interest is a subgroup that the treatment of interest has a significant impact on.

In some embodiments, associating each patient subgroup of the one or more patient subgroups with the covariant comprises: generating, for a patient subgroup, a model configured to receive an indication of whether a patient in the patient subgroup received the treatment of interest and output a predicted disease progression; and evaluating the model to determine if the patient subgroup is the patient subgroup of interest.

In some embodiments, evaluating the model comprises determining a correlation metric of the model and comparing the correlation metric against a predefined threshold.

In some embodiments, the correlation metric is a P value.

In some embodiments, the generated model is trained by disease progression values of subjects in the patient subgroup.

In some embodiments, the disease progression values comprise medical diagnosis scores of the subjects in the patient subgroup.

In some embodiments, the disease progression values comprise progression scores of the subjects in the patient subgroup.

In some embodiments, the disease progression values comprise DRP values of the subjects in the patient subgroup.

In some embodiments, the covariant is a progression of a disease of interest and wherein the patient subgroup of interest is a subgroup that has a significant association with the progression of the disease of interest.

In some embodiments, associating each patient subgroup of the one or more patient subgroups with the covariant comprises: generating, for a patient subgroup, a model configured to receive an indication of whether a patient belongs to the patient subgroup and output a predicted disease progression; and evaluating the model to determine if the patient subgroup is the patient subgroup of interest.

In some embodiments, evaluating the model comprises determining a correlation metric of the model and comparing the correlation metric against a predefined threshold.

In some embodiments, the correlation metric is a P value.

In some embodiments, the generated model is trained by disease progression values of the group of clinic subjects.

In some embodiments, the disease progression values comprise medical diagnosis scores of the subjects in the patient subgroup, progression scores of the subjects in the patient subgroup, or DRP values of the subjects in the patient subgroup.

In some embodiments, the covariant is an adverse side effect and wherein the patient subgroup of interest is a subgroup that has a significant association with the adverse side effect. In some embodiments, associating each patient subgroup of the one or more patient subgroups with the covariant comprises: generating, for a patient subgroup, a model configured to receive an indication of whether a patient in the patient subgroup belongs to the patient subgroup and predict if the patient has the adverse side effect; and evaluating the model to determine if the patient subgroup is the patient subgroup of interest.

In some embodiments, the covariant is an adverse side effect and wherein the patient subgroup of interest is a subgroup that has a significant association with experiencing the adverse side effect after a treatment. In some embodiments, associating each patient subgroup of the one or more patient subgroups with the covariant comprises: generating, for a patient subgroup, a model configured to receive an indication of whether a patient in the patient subgroup has received at treatment and predict if the patient has the adverse side effect; and evaluating the model to determine if the patient subgroup is the patient subgroup of interest.

In some embodiments, evaluating the model comprises determining a correlation metric of the model and comparing the correlation metric against a predefined threshold.

In some embodiments, the correlation metric is a P value.

In an exemplary implementation, the system may be configured to identify clinically relevant patient segments to increase efficacy and reduce ASE. First, the system may obtain biopsy embeddings from (some or all) H&E-stained liver biopsy images through the unsupervised learning procedure. The system may then perform an unsupervised analysis of baseline biopsy embeddings to identify clusters of patients based on biopsy embedding similarities. For each cluster, the system may determine or obtain a binary indicator vector across patients to indicate whether the patient is in the cluster or not. This binary phenotype can be used in downstream analyses.

The system may further be configured to assess an association with disease progression of different clusters, for example by using the linear model testing procedure described with respect to model 316 in FIG. 3B to test for association between cluster identity and the clinical trial endpoint. For example, the system may fit a cluster-specific model that receives a cluster binary indicator (patient in cluster coded as 1, not in cluster coded as 0) and outputs a clinical score or end point (e.g., disease progression).

The system can also assess treatment efficacy within different clusters of patients, for example by using the linear model testing procedure described with respect to model 316 in FIG. 3B to test for association between treatment and the clinical endpoint considering only patients in a given cluster. For example, the system can fit a cluster-specific model that receives a binary indicator for treatment vs placebo and outputs a clinical endpoint (e.g. fibrosis progression). The analysis may then be restricted to patients within a specific cluster.

The system can also assess adverse side effects associated with different clusters (for example by using the linear model testing procedure described with respect to model 316 in FIG. 3B to test for association between cluster identity and adverse side effect covariates. For example, the system may fit a cluster-specific model that receives a binary indicator (e.g., patient in cluster coded as 1, not in cluster coded as 0) and output a side effect or adverse event. For example, the system may restrict the analysis to patients receiving a specific treatment, and the analyzed output could be whether the patient drops from the clinical trial due to an adverse event (as binary indicator). This would enable identification of patients that are more likely to have adverse side effects from a treatment.

If a specific cluster is associated with progression, the system can then identify genetic and phenotypic biomarkers of that cluster (for example by using the linear model testing procedure described with respect to model 316 in FIG. 3B to test for association between cluster identity and genetics, expression, lab values, etc.). For example, the system fits a model that receives a cluster binary indicator (e.g., patient in cluster coded as 1, not in cluster coded as 0) and outputs a clinical score or end point (e.g., disease progression). The clinical end point can be quantified as a progression score or the clinical endpoint monitored in the clinical trial (e.g., whether patients have a higher or lower fibrosis score based on pathologist assessment).

In some embodiments, the techniques described herein can be based on expression data rather than biopsy embeddings. For example, the system may be tested for associations between baseline expression levels and disease progression in patients using the linear model testing procedure described with reference to model 316 in FIG. 3B. For example, a linear mixed model can be generated to receive a baseline expression level as the input and output a disease progression prediction. This procedure, as an example, may identify 130 genes significantly associated with progression. In this example, Leiden clustering may be performed using scanpy of patients based on expression of the 130 progression genes (after regressing out fibrosis baseline state and clinical trial indicator).

The system assessed association with disease progression of different clusters by using the linear model testing procedure described with reference to model 316 in FIG. 3B to test for association between cluster identity and disease progression. For example, a linear mixed model can be generated to receive a cluster identity (e.g., whether the patient belongs to the cluster) as the input and output a disease progression prediction. In the example, the analysis identified two clusters associated with progression and one with regression.

Figure 25:
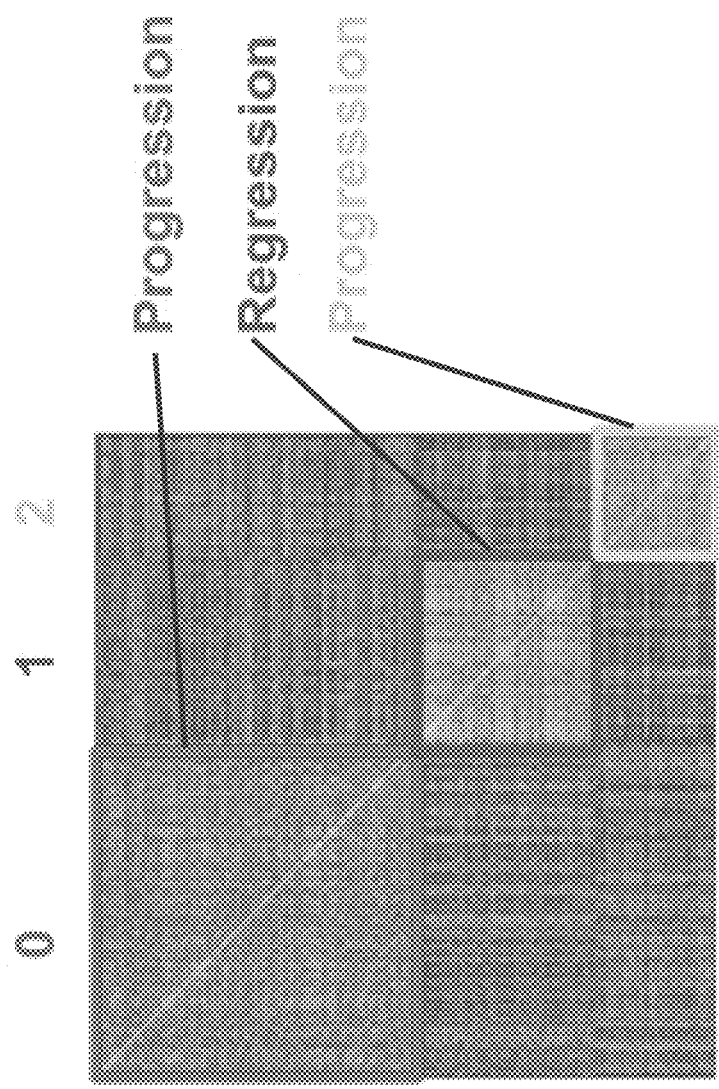
FIG. 25 illustrates three patient clusters, in accordance with some embodiments.

For each gene, the system may be configured to fit a linear regression model that receives, as input, a baseline state and a clinical trial indicator, and outputs its expression. The system may subtract the contributions from baseline state and clinical trial indicator estimated through the linear model from original expression values. As seen with respect to FIG. 25, the example analysis revealed three patient clusters. The two progression clusters correspond to different gene expression signatures. In other words, in the example of FIG. 25, after the system clusters patients based on the baseline expression levels of genes associated with progression, three groups are observed. Of these, two groups of patients tended to progress, however these groups have different gene signatures at baseline. This heterogeneity may indicate a fundamental difference between these groups of patients. In other words, these groups of patients may respond differently to specific treatments, genetic drivers may be different, etc.

The system assessed a search performed for expression biomarkers associated with the different clusters by using the linear model testing procedure described with reference to model 316 in FIG. 3B to test for association between cluster identity and expression values. For example, a linear mixed model can be generated to receive a cluster identity (e.g., whether the patient is in the cluster) as the input and output an expression value. This analysis sets of around 10 expression biomarkers associated with each of the clusters.

In some embodiments, image-based biomarkers may be developed. For instance, predictive images may be visualized for a condition of interest. For example, the condition of interest may refer to a high or low disease score, a genetic sequence versus another genetic sequence, and the like. A hypothesis of associated imaging features may be generated based on a visualization of the predictive images. For example, cell features in a cell may appear to be different in a sample in the condition of interest as opposed to one not in the condition of interest. A model may be generated that is specifically designed to measure the associated feature(s), which may be image-based biomarkers. The model may then be evaluated with new data and potentially used as a new image-based biomarker.

FIG. 28 illustrates a comparison of z-scores, in accordance with some embodiments. In some embodiments, FIG. 28 illustrates a comparison of z-scores of an analysis of treatment vs. placebo in a small trial versus an analysis of imputed DRP in a large trial. FIG. 28 may illustrate that the analysis of DRP can identify genes that are correlated with those identified with an analysis of true treatment effect in small samples. Furthermore, FIG. 28 may demonstrate that the aforementioned technique is better powered. Still further, this approach may enable an analysis of treatment as it correlates in a study that did not have the covariate of interest measured.

Figure 29:
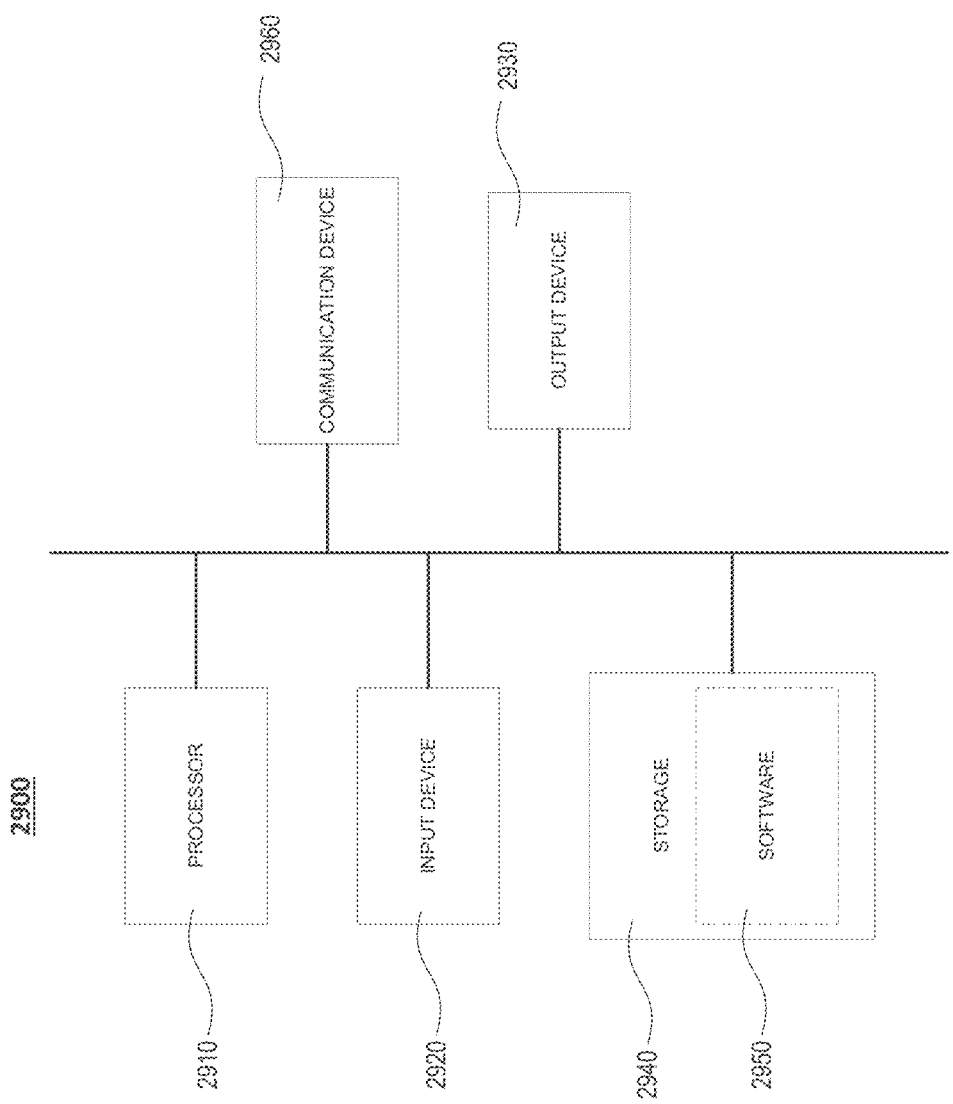
FIG. 29 illustrates an exemplary electronic device, in accordance with some embodiments.

FIG. 29 illustrates an example of a computing device in accordance with one embodiment. Device 2900 can be a host computer connected to a network. Device 2900 can be a client computer or a server. As shown in FIG. 29, device 2900 can be any suitable type of microprocessor-based device, such as a personal computer, workstation, server or handheld computing device (portable electronic device) such as a phone or tablet. The device can include, for example, one or more of processor 2910, input device 2920, output device 2930, storage 2940, and communication device 2960. Input device 2920 and output device 2930 can generally correspond to those described above, and can either be connectable or integrated with the computer.

Input device 2920 can be any suitable device that provides input, such as a touch screen, keyboard or keypad, mouse, or voice-recognition device. Output device 2930 can be any suitable device that provides output, such as a touch screen, haptics device, or speaker.

Storage 2940 can be any suitable device that provides storage, such as an electrical, magnetic or optical memory including a RAM, cache, hard drive, or removable storage disk. Communication device 2960 can include any suitable device capable of transmitting and receiving signals over a network, such as a network interface chip or device. The components of the computer can be connected in any suitable manner, such as via a physical bus or wirelessly.

Software 2950, which can be stored in storage 2940 and executed by processor 2910, can include, for example, the programming that embodies the functionality of the present disclosure (e.g., as embodied in the devices as described above).

Software 2950 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 2940, that can contain or store programming for use by or in connection with an instruction execution system, apparatus, or device.

Software 2950 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 2900 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 2900 can implement any operating system suitable for operating on the network. Software 2950 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purposes of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

The present techniques will be better understood with reference to the following enumerated embodiments:

1. A method of identifying a covariant of interest with respect to a phenotype, comprising: receiving covariant information of a covariate class and corresponding phenotypic data related to the phenotype obtained from a group of clinical subjects; inputting the phenotypic data into a trained unsupervised machine-learning model to obtain a plurality of embeddings in a latent space, each embedding corresponding to a phenotypic state reflected in the phenotypic data; and determining, based on (i) the covariant information for the group of clinical subjects, (ii) the plurality of embeddings, and (iii) one or more machine learning models, an association between each of a plurality of candidate covariants and the phenotype to identify the covariant of interest.

2. The method of embodiment 1, wherein the one or more machine learning models comprise a linear regression model.

3. The method of any one of embodiments 1-2, wherein the one or more machine learning models include the trained unsupervised machine-learning model.

4. The method of any one of embodiments 1-3, wherein the phenotype comprises a disease of interest, a gene expression, metabolomics, proteomics, or lipidomics.

5. The method of any of embodiments 1-4, wherein the phenotypic data comprises medical imaging data, biopsy data, clinical biomarker data, or genomic biomarker data.

6. The method of any of embodiments 1-5, wherein the covariate class comprises demographic information, clinical covariates, or genomic data.

7. The method of any of embodiments 1-6, wherein determining the association between each candidate covariant and the phenotype comprises: inputting each embedding of the plurality of embeddings into a linear regression model to receive a predicted continuous score for each embedding of the plurality of embeddings to obtain a plurality of predicted continuous scores; associating the plurality of predicted continuous scores with a candidate covariant expressed by the group of clinical subjects; and determining, based on the association, a correlation metric between the phenotype and the candidate covariant, the correlation metric indicative of an impact of the candidate covariant on the phenotype.

8. The method of any of embodiments 1-6, wherein determining the association between the candidate covariant and the phenotype comprises: associating the plurality of embeddings with each candidate covariant of the plurality of candidate covariants to identify a subset of the plurality of candidate covariants; and associating each candidate covariant in the subset with the phenotype to identify the covariant of interest.

9. The method of any of embodiments 1-8, further comprising: generating, based on the covariant of interest, a plurality of predicted images depicting the phenotype; and displaying, on a display, the plurality of predicted images.

10. The method of embodiment 9, further comprising: ranking the plurality of predicted images.

11. The method of embodiment 10, wherein the plurality of predicted images are displayed based on the ranking.

12. The method of any of embodiments 1-11, further comprising: identifying a relationship between the covariant of interest and the phenotype.

13. The method of embodiment 12, wherein the relationship is a causal relationship.

14. The method of any of embodiments 12-13, further comprising: providing a diagnosis in a new subject based on the relationship.

15. The method of any of embodiments 12-14, further comprising: developing a treatment based on the relationship.

16. The method of any of embodiments 12-15, further comprising: administering, adjusting, or applying a treatment based on the relationship.

17. The method of any of embodiments 12-16, further comprising: providing a medical recommendation based on the relationship.

18. The method of any of embodiments 12-17, further comprising: identifying a biological target for treating a disease of interest based on the relationship, wherein the phenotype comprises the disease of interest.

19. The method of embodiment 18, wherein the disease of interest is non-alcoholic steatohepatitis (NASH).

20. A method of identifying at least one genetic variant of interest with respect to a disease of interest, comprising: inputting a plurality of medical images obtained from a group of clinical subjects into a trained unsupervised machine-learning model to obtain a plurality of embeddings in a latent space, each embedding corresponding to a phenotypic state relative to the disease of interest reflected in one or more of the plurality of medical images; inputting each embedding of the plurality of embeddings into a trained machine learning model to receive a predicted continuous medical diagnosis score for each embedding of the plurality of embeddings to obtain a plurality of predicted medical diagnosis scores, each predicted continuous medical diagnosis score indicative of a state of the disease of interest; associating the plurality of predicted medical diagnosis scores with each candidate genetic variant of a plurality of candidate genetic variants expressed by the group of clinical subjects from whom the plurality of medical images was taken; and determining, based on the association, a correlation metric between the disease of interest and each candidate genetic variant to identify the at least one genetic variant of interest from the plurality of candidate genetic variants, the correlation metric indicative of an impact of each candidate genetic variant on the disease of interest.

21. The method of embodiment 20, further comprising: comparing the correlation metric with a predefined threshold.

22. The method of embodiment 21, further comprising: identifying, based on the comparison, a relationship between each candidate genetic variant of interest and the disease of interest.

23. The method of embodiment 22, wherein the relationship is a causal relationship.

24. The method of any of embodiments 22-23, further comprising: diagnosing the disease of interest in a new subject based on the relationship.

25. The method of any of embodiments 22-24, further comprising: developing a treatment based on the relationship.

26. The method of any of embodiments 22-25, further comprising: administering, adjusting, or applying a treatment based on the relationship.

27. The method of any of embodiments 22-26, further comprising: providing a medical recommendation based on the relationship.

28. The method of any of embodiments 22-27, further comprising: identifying a biological target for treating the disease of interest based on the relationship.

29. The method of any of embodiments 22-28, wherein the disease of interest is non-alcoholic steatohepatitis (NASH).

30. The method of any of embodiments 20-29, wherein the plurality of medical images comprises biopsy images.

31. The method of embodiment 30, wherein the biopsy images correspond to one or more clinical trials.

32. The method of any of embodiments 20-31, further comprising: dividing a medical image of the plurality of medical images into a plurality of image tiles; inputting each image tile of the plurality of image tiles into the trained unsupervised machine-learning model to receive a tile embedding for each image tile to obtain a plurality of tile embeddings; and aggregating the plurality of tile embeddings to obtain an embedding of the plurality of embeddings.

33. The method of embodiment 32, wherein aggregating the plurality of tile embeddings comprises averaging the plurality of tile embeddings.

34. The method of any of embodiments 20-33, wherein the trained unsupervised machine-learning model is a contrastive model.

35. The method of embodiment 34, wherein the contrastive model is a SimCLR model.

36. The method of any of embodiments 20-34, wherein the trained unsupervised machine-learning model is trained at least partially based on the plurality of medical images.

37. The method of any of embodiments 20-34, wherein the trained unsupervised machine-learning model is fine-tuned based on the plurality of medical images.

38. The method of any one of embodiments 20-37, wherein the one or more machine learning models comprise a linear regression model.

39. The method of embodiment 38, wherein the linear regression model is a trained linear regression model.

40. The method of embodiment 39, wherein the trained linear regression model is fitted based on the plurality of embeddings and a plurality of assigned medical diagnosis scores corresponding to the plurality of embeddings.

41. The method of any of embodiments 20-37, wherein the one or more machine learning models comprise a linear mixed model.

42. The method of any one of embodiments 20-41, wherein the one or more machine learning models include the trained unsupervised machine-learning model.

43. The method of embodiment 42, wherein the plurality of assigned medical diagnosis scores are provided by one or more medical practitioners.

44. The method of embodiment 43, wherein each assigned medical diagnosis score of the plurality of assigned medical diagnosis scores is selected from a set of predefined values.

45. The method of any of embodiments 20-44, wherein the plurality of predicted medical diagnosis scores is a plurality of predicted fibrosis scores, a plurality of predicted lobular inflammation scores, or a plurality of predicted steatosis scores.

46. The method of any of embodiments 20-45, wherein the plurality of predicted medical diagnosis scores comprise disease progression scores calculated as a difference between predicted medical diagnosis scores reflecting different measurements obtained during a clinical trial.

47. The method of any of embodiments 20-45, wherein the plurality of predicted medical diagnosis scores comprise disease progression scores obtained as a slope determined by a linear model trained on predicted medical diagnosis scores reflecting different measurements obtained for each individual during a clinical trial.

48. The method of any one of embodiments 18-47, wherein the plurality of predicted medical diagnosis scores comprise disease progression scores calculated as a difference between a predicted follow-up score and an observed follow-up score controlling for a corresponding baseline score.

49. The method of any of embodiments 20-48, wherein associating the plurality of predicted medical diagnosis scores with each candidate genetic variant comprises fitting a variant-specific model configured to receive a value indicative of the candidate genetic variant and output a predicted medical diagnosis score.

50. The method of embodiment 49, wherein the variant-specific model is a linear model.

51. The method of embodiment 49, wherein the variant-specific model is fitted based on the plurality of predicted medical diagnosis scores and a plurality of values indicative of the candidate genetic variant.

52. The method of any of embodiments 20-50, wherein determining the correlation metric comprises determining a P value based on a variant-specific model.

53. A method of identifying at least one genetic variant of interest with respect to a disease of interest, comprising: inputting a plurality of medical images obtained from a group of clinical subjects into a trained unsupervised machine-learning model to obtain a plurality of embeddings in a latent space, each embedding corresponding to a phenotypic state relative to the disease of interest reflected in one or more of the plurality of medical images; associating the plurality of embeddings with each candidate genetic variant of a plurality of candidate genetic variants to identify a subset of the plurality of candidate genetic variants, wherein the subset of the plurality of candidate genetic variants is associated with histological features reflected in the plurality of medical images; and associating each candidate genetic variant of the subset of the plurality of candidate genetic variants with the disease of interest to identify the at least one genetic variant of interest from the subset.

54. The method of embodiment 53, further comprising: generating, based on the at least one genetic variant of interest, a plurality of simulated images depicting the disease of interest; and displaying, on a display, the plurality of simulated images.

55. The method of embodiment 54, further comprising: ranking the plurality of simulated images.

56. The method of embodiment 55, wherein the plurality of simulated images are displayed based on the ranking.

57. The method of any one of embodiments 53-56, further comprising: identifying a relationship between the at least one genetic variant of interest and the disease of interest.

58. The method of embodiment 57, wherein the relationship is a causal relationship.

59. The method of any of embodiments 57-58, further comprising: diagnosing the disease of interest in a new subject based on the relationship.

60. The method of any of embodiments 57-59, further comprising: developing a treatment based on the relationship.

61. The method of any of embodiments 57-60, further comprising: administering, adjusting, or applying a treatment based on the relationship.

62. The method of any of embodiments 57-61, further comprising: providing a medical recommendation based on the relationship.

63. The method of any of embodiments 57-62, further comprising: identifying a biological target for treating the disease of interest based on the relationship.

64. The method of any of embodiments 53-63, wherein the disease of interest is non-alcoholic steatohepatitis (NASH).

65. The method of any of embodiments 53-64, wherein the plurality of medical images comprises biopsy images.

66. The method of embodiment 65, wherein the biopsy images correspond to one or more clinical trials.

67. The method of any of embodiments 53-66, further comprising: dividing a medical image of the plurality of medical images into a plurality of image tiles; inputting each image tile of the plurality of image tiles into the trained unsupervised machine-learning model to receive a tile embedding for each image tile to obtain a plurality of tile embeddings; and aggregating the plurality of tile embeddings to obtain an embedding of the plurality of embeddings.

68. The method of embodiment 67, wherein aggregating the plurality of tile embeddings comprises averaging the plurality of tile embeddings.

69. The method of any of embodiments 53-68, wherein the trained unsupervised machine-learning model is a contrastive model.

70. The method of embodiment 69, wherein the contrastive model is a SimCLR model.

71. The method of any of embodiments 53-70, wherein the trained unsupervised machine-learning model is trained at least partially based on the plurality of medical images.

72. The method of any of embodiments 53-70, wherein the trained unsupervised machine-learning model is fine-tuned based on the plurality of medical images.

73. The method of any of embodiments 53-72, wherein associating the plurality of embeddings with each genetic variant of the plurality of candidate genetic variants to identify the subset of the plurality of candidate genetic variants comprises: generating, for a candidate genetic variant of the plurality of candidate genetic variants, a variant-specific model configured to receive an embedding and output a value of the candidate genetic variant; and evaluating the variant-specific model to determine whether to include the candidate genetic variant in the subset.

74. The method of embodiment 73, wherein evaluating the variant-specific model comprises: calculating a correlation metric based on the variant-specific model; and comparing the correlation metric with a predefined threshold.

75. The method of embodiment 74, wherein the correlation metric is a P value associated with the variant-specific model.

76. The method of any of embodiments 53-75, wherein associating each genetic variant of the subset of the plurality of candidate genetic variants with the disease of interest to identify the at least one genetic variant of interest comprises: generating, for a genetic variant in the subset, a variant-specific model configured to receive a value indicative of the genetic variant and output a medical diagnosis score related to the disease of interest; and evaluating the variant-specific model to determine whether the candidate genetic variant is the at least one genetic variant of interest.

77. The method of embodiment 76, wherein evaluating the variant-specific model comprises: calculating a correlation metric based on the variant-specific model; and comparing the correlation metric with a predefined threshold.

78. The method of embodiment 77, wherein the correlation metric is a P value associated with the variant-specific model.

79. A method of evaluating a treatment with respect to progression of a disease of interest, comprising: obtaining a plurality of baseline placebo medical images of a placebo group of subjects captured before a placebo is administered to the placebo group of subjects and a plurality of follow-up placebo medical images of the placebo group of subjects captured after the placebo is administered to the placebo group of subjects; obtaining a plurality of placebo progression embeddings based on the plurality of baseline placebo medical images and the plurality of follow-up placebo medical images; obtaining a plurality of baseline treatment medical images of a treatment group of subjects captured before the treatment is administered to the treatment group of subjects and a plurality of follow-up treatment medical images of the treatment group of subjects captured after the treatment is administered to the treatment group of subjects; obtaining a plurality of treatment progression embeddings based on the plurality of baseline treatment medical images and the plurality of follow-up treatment medical images; and generating a classification model for determining whether a patient has received the placebo or the treatment based on the plurality of treatment progression embeddings.

80. The method of embodiment 79, wherein outputs of the classification model are indicative of drug response phenotypes.

81. The method of embodiment 80, further comprising: determining, based on the classification model, a correlation metric between the treatment and the progression of the disease of interest.

82. The method of any one of embodiments 79-81, wherein the correlation metric is a P value.

83. The method of any one of embodiments 79-82, further comprising: comparing the correlation metric with a predefined threshold.

84. The method of embodiment 83, further comprising: identifying, based on the comparison, an association between the treatment and progression of the disease of interest.

85. The method of embodiment 84, further comprising: prescribing the treatment in a new subject based on the association.

86. The method of embodiment 84, further comprising: administering the treatment based on the association.

87. The method of embodiment 84, further comprising: adjusting the treatment based on the association.

88. The method of embodiment 84, further comprising: providing a medical recommendation based on the association.

89. The method of embodiment 84, further comprising: generating a report based on the association.

90. The method of any of embodiments 79-89, wherein the disease of interest is non-alcoholic steatohepatitis (NASH).

91. The method of any of embodiments 79-90, wherein obtaining the plurality of placebo progression embeddings comprises: inputting the plurality of baseline placebo medical images into a trained unsupervised machine-learning model to obtain a plurality of baseline placebo embeddings in a latent space; inputting the plurality of follow-up placebo medical images into the trained unsupervised machine-learning model to obtain a plurality of follow-up placebo embeddings in the latent space; inputting the plurality of baseline placebo embeddings into one or more machine learning models to obtain a plurality of predicted follow-up placebo embeddings in the latent space; and determining the plurality of placebo progression embeddings by calculating differences between the plurality of follow-up placebo embeddings and the plurality of predicted follow-up placebo embeddings.

92. The method of embodiment 91, wherein the one or more machine learning models comprise a trained linear model.

93. The method of any of embodiments 91-92, wherein the one or more machine learning models include the trained unsupervised machine-learning model.

94. The method of any of embodiments 91-93, wherein obtaining the plurality of treatment progression embeddings comprises: inputting the plurality of baseline treatment medical images into the trained unsupervised machine-learning model to obtain a plurality of baseline treatment embeddings in a latent space; inputting the plurality of follow-up treatment medical images into the trained unsupervised machine-learning model to obtain a plurality of follow-up treatment embeddings in the latent space; inputting the plurality of baseline treatment embeddings into the trained linear model to obtain a plurality of predicted follow-up treatment embeddings in the latent space; and determining the plurality of treatment progression embeddings by calculating differences between the plurality of follow-up treatment embeddings and the plurality of predicted follow-up treatment embeddings.

95. The method of any of embodiments 91-94, wherein the trained unsupervised machine-learning model is a contrastive model.

96. The method of embodiment 95, wherein the contrastive model is a SimCLR model.

97. The method of any of embodiments 91-96, wherein the trained linear model is configured to receive a baseline embedding and output a predicted follow-up embedding.

98. The method of embodiment 97, wherein the trained linear model is a linear mixed model.

99. The method of embodiment 97, wherein the placebo group of subjects is a first placebo group, and wherein the trained linear model is trained using embeddings obtained from medical image data from a second placebo group different from the first placebo group.

100. The method of any of embodiments 79-99, wherein the classification model is configured to receive an input progression embedding and output a classification result indicating whether a patient has received the placebo or the treatment.

101. The method of any of embodiments 79-100, wherein the plurality of baseline placebo medical images, the plurality of follow-up placebo medical images, the plurality of baseline treatment medical images, and the plurality of follow-up treatment medical images are biopsy images.

102. A method of identifying a covariant of interest with respect to drug response phenotype (DRP) of a treatment, comprising: receiving covariant information of a covariate class obtained from a group of clinical subjects; receiving a plurality of baseline images and a plurality of follow-up images from the group of clinical subjects; obtaining a plurality of progression embeddings based on the plurality of baseline images and the plurality of follow-up images; inputting the plurality of progression embeddings into a trained classification model to obtain a plurality of classification results indicative of DRP values of the group of clinical subjects; and determining, based on the covariant information for the group of clinical subjects, the plurality of classification results, and one or more machine learning models, an association between each candidate covariant of a plurality of candidate covariants and the DRP values to identify the covariant of interest.

103. The method of embodiment 102, wherein the one or more machine learning models comprise one or more linear regression models.

104. The method of any one of embodiments 102-103, wherein the plurality of candidate covariants comprises a plurality of candidate missense variants.

105. The method of any one of embodiments 102-103, wherein the plurality of candidate covariants comprises a plurality of candidate genes.

106. The method of any of embodiments 102-105, wherein the covariate class comprises demographic information, clinical covariates, or genomic data.

107. The method of any of embodiments 102-106, further comprising: diagnosing a disease of interest in a new subject based on the identified covariant of interest.

108. The method of any of embodiments 102-107, further comprising: developing a treatment based on the identified covariant of interest.

109. The method of any of embodiments 102-108, further comprising: administering, adjusting, or applying the treatment based on the identified covariant of interest.

110. The method of any of embodiments 102-109, further comprising: providing a medical recommendation based on the identified covariant of interest.

111. The method of any of embodiments 102-110, further comprising: identifying a biological target based on the identified covariant of interest.

112. The method of any of embodiments 102-111, wherein the plurality of baseline medical images and the plurality of follow-up medical images comprise biopsy images.

113. The method of any of embodiments 102-112, wherein obtaining the plurality of progression embeddings based on the plurality of baseline medical images and the plurality of follow-up medical images comprises: inputting the plurality of baseline medical images into a trained unsupervised machine-learning model to obtain a plurality of baseline embeddings in a latent space; inputting the plurality of follow-up medical images into the trained unsupervised machine-learning model to obtain a plurality of follow-up embeddings in the latent space; inputting the plurality of baseline embeddings into a trained linear model to obtain a plurality of predicted follow-up embeddings in the latent space; and determining the plurality of progression embeddings by calculating differences between the plurality of follow-up embeddings and the plurality of predicted follow-up embeddings.

114. The method of embodiments 113, wherein the trained unsupervised machine-learning model is a contrastive model.

115. The method of embodiment 114, wherein the contrastive model is a SimCLR model.

116. The method of embodiment 113, wherein the trained linear model is configured to receive a baseline embedding and output a predicted follow-up embedding.

117. The method of embodiment 113, wherein the trained linear model is a linear mixed model.

118. The method of any of embodiments 102-117, wherein the trained classification model is configured to receive an input progression embedding and determine whether a patient has received a placebo or the treatment.

119. The method of any of embodiments 102-118, wherein identifying the covariant of interest comprises: for a candidate covariant of the plurality of candidate covariants: generating a model based on the DRP values and the covariant information of the group of clinical subjects; and determining a correlation metric based on the model.

120. The method of embodiment 119, wherein the correlation metric is a P value.

121. The method of embodiment 119, further comprising: comparing the correlation metric against a predefined threshold to determine if the candidate covariant is the covariant of interest.

122. A method of evaluating a treatment with respect to progression of a disease of interest, comprising: obtaining medical images comprising: (a) a plurality of baseline placebo medical images of a placebo group of subjects captured before a placebo is administered to the placebo group of subjects, (b) a plurality of follow-up placebo medical images of the placebo group of subjects captured after the placebo is administered to the placebo group of subjects, (c) a plurality of baseline treatment medical images of a treatment group of subjects captured before the treatment is administered to the treatment group of subjects, and (d) a plurality of follow-up treatment medical images of the treatment group of subjects captured after the treatment is administered to the treatment group of subjects; inputting the medical images into a trained unsupervised machine-learning model to obtain a plurality of embeddings, each embedding corresponding to a phenotypic state relative to the disease of interest reflected in one or more of the medical images; inputting the plurality of embeddings into one or more machine learning models to obtain a plurality of predicted continuous medical diagnosis scores, each predicted continuous medical diagnosis score indicative of a state of the disease of interest; determining a plurality of placebo progression scores and a plurality of treatment progression scores based on the plurality of predicted continuous medical diagnosis scores; associating the plurality of placebo progression scores and the plurality of treatment progression scores with the treatment; and determining, based on the association, a correlation metric between the plurality of placebo progression scores and the plurality of treatment progression scores.

123. The method of embodiment 122, wherein inputting the medical images into a trained unsupervised machine-learning model to obtain the plurality of embeddings comprises: inputting (a) into the trained unsupervised machine-learning model to obtain a plurality of baseline placebo embeddings; inputting (b) into the trained unsupervised machine-learning model to obtain a plurality of follow-up placebo embeddings; inputting (c) into a trained unsupervised machine-learning model to obtain a plurality of baseline treatment embeddings; and inputting (d) into the trained unsupervised machine-learning model to obtain a plurality of follow-up treatment embeddings.

124. The method of any of embodiments 122-123, wherein the one or more machine learning models comprise a trained linear regression model.

125. The method of any one of embodiments 122-124, wherein the one or more machine learning models include the trained unsupervised machine learning model.

126. The method of embodiment any one of embodiments 124-125, wherein inputting the plurality of embeddings into the one or more machine learning models comprises: inputting the plurality of baseline placebo embeddings into the trained linear regression model to obtain a plurality of baseline placebo scores; inputting the plurality of follow-up placebo embeddings into the trained linear regression model to obtain a plurality of follow-up placebo scores; inputting the plurality of baseline treatment embeddings into the trained linear regression model to obtain a plurality of baseline treatment scores; and inputting the plurality of follow-up treatment embeddings into the trained linear regression model to obtain a plurality of follow-up treatment scores.

127. The method of embodiment 126, wherein determining the plurality of placebo progression scores and the plurality of treatment progression scores comprises: determining differences between the plurality of baseline placebo scores and the plurality of follow-up placebo scores to determine the plurality of placebo progression scores; and determining differences between the plurality of baseline treatment scores and the plurality of follow-up treatment scores to determine the plurality of treatment progression scores.

128. The method of embodiment 126, wherein determining the plurality of placebo progression scores and the plurality of treatment progression scores comprises: determining, for each subject in the placebo group of subjects, a slope of a linear model fitted at least based on a baseline placebo score and a follow-up placebo score of the subject in the placebo group of subjects; and determining, for each subject in the treatment group of subjects, a slope of a linear model fitted at least based on a baseline placebo score and a follow-up placebo score of the subject in the treatment group of subjects.

129. The method of any one of embodiments 122-128, wherein the plurality of predicted medical diagnosis scores comprise disease progression scores calculated as a difference between a predicted follow-up score and an observed follow-up score controlling for a corresponding baseline score.

130. The method of any of embodiments 122-129, wherein associating the plurality of placebo progression scores and the plurality of treatment progression scores with the treatment comprises generating a model configured to receive an indication of whether a patient received the treatment and output a predicted disease progression score.

131. The method of embodiment 130, wherein the correlation metric is P value of the model.

132. The method of any of embodiments 122-130, further comprising: comparing the correlation metric with a predefined threshold.

133. The method of embodiment 132, further comprising: identifying, based on the comparison, an association between the treatment and the disease of interest.

134. The method of embodiment 133, further comprising: administering, adjusting, or applying the treatment based on the association.

135. The method of embodiment 133, further comprising: providing a medical recommendation based on the association.

136. The method of any of embodiments 122-135, wherein the disease of interest is non-alcoholic steatohepatitis (NASH).

137. The method of any of embodiments 122-136, wherein the trained unsupervised machine-learning model is a contrastive model.

138. The method of embodiment 137, wherein the contrastive model is a SimCLR model.

139. The method of any of embodiments 124-138, wherein the trained linear regression model is a linear mixed model.

140. The method of any of embodiments 124-139, wherein the trained linear regression model is fitted based on a plurality of assigned medical diagnosis scores.

141. The method of embodiment 140, wherein the plurality of assigned medical diagnosis scores are provided by one or more medical practitioners.

142. The method of embodiment 141, wherein each assigned medical diagnosis score of the plurality of assigned medical diagnosis scores is selected from a set of predefined values.

143. The method of any of embodiments 122-142, wherein the plurality of predicted continuous medical diagnosis scores comprise a plurality of predicted fibrosis scores, a plurality of predicted lobular inflammation scores, or a plurality of predicted steatosis scores.

144. A method of identifying a patient subgroup of interest, comprising: inputting a plurality of medical images obtained from a group of clinical subjects into a trained unsupervised machine-learning model to obtain a plurality of embeddings in a latent space; clustering the plurality of embeddings to generate one or more clusters of embeddings; identifying one or more patient subgroups corresponding to the one or more clusters of embeddings; and associating each patient subgroup of the one or more patient subgroups with a covariant to identify the patient subgroup of interest.

145. The method of embodiment 144, wherein the trained unsupervised machine-learning model is a contrastive model.

146. The method of embodiment 145, wherein the contrastive model is a SimCLR model.

147. The method of any of embodiments 144-146, wherein the covariant is a treatment of interest and wherein the patient subgroup of interest is a subgroup that the treatment of interest has a significant impact on.

148. The method of embodiment 147, wherein associating each patient subgroup of the one or more patient subgroups with the covariant comprises: generating, for a patient subgroup, a model configured to receive an indication of whether a patient in the patient subgroup received the treatment of interest and output a predicted disease progression; and evaluating the model to determine if the patient subgroup is the patient subgroup of interest.

149. The method of embodiment 148, wherein evaluating the model comprises determining a correlation metric of the model and comparing the correlation metric against a predefined threshold.

150. The method of any one of embodiments 148-149, wherein the correlation metric is a P value.

151. The method of any of embodiments 148-150, wherein the generated model is trained by disease progression values of subjects in the patient subgroup.

152. The method of embodiment 151, wherein the disease progression values comprise medical diagnosis scores of the subjects in the patient subgroup.

153. The method of embodiment 151, wherein the disease progression values comprise progression scores of the subjects in the patient subgroup.

154. The method of embodiment 151, wherein the disease progression values comprise DRP values of the subjects in the patient subgroup.

155. The method of any of embodiments 144-146, wherein the covariant is a progression of a disease of interest and wherein the patient subgroup of interest is a subgroup that has a significant association with the progression of the disease of interest.

156. The method of embodiment 151, wherein associating each patient subgroup of the one or more patient subgroups with the covariant comprises: generating, for a patient subgroup, a model configured to receive an indication of whether a patient belongs to the patient subgroup and output a predicted disease progression; and evaluating the model to determine if the patient subgroup is the patient subgroup of interest.

157. The method of embodiment 152, wherein evaluating the model comprises determining a correlation metric of the model and comparing the correlation metric against a predefined threshold.

158. The method of embodiment 157, wherein the correlation metric is a P value.

159. The method of any of embodiments 156-158, wherein the generated model is trained by disease progression values of the group of clinical subjects.

160. The method of embodiment 159, wherein the disease progression values comprise medical diagnosis scores of clinical subjects in the patient subgroup, progression scores of clinical subjects in the patient subgroup, or DRP values of clinical subjects in the patient subgroup.

161. The method of any of embodiments 144-146, wherein the covariant is an adverse side effect and wherein the patient subgroup of interest is a subgroup that has a significant association with the adverse side effect.

162. The method of embodiment 161, wherein associating each patient subgroup of the one or more patient subgroups with the covariant comprises: generating, for a patient subgroup, a model configured to receive an indication of whether a patient in the patient subgroup belongs to the patient subgroup and predict if the patient has the adverse side effect; and evaluating the model to determine if the patient subgroup is the patient subgroup of interest.

163. The method of embodiment 162, wherein evaluating the model comprises determining a correlation metric of the model and comparing the correlation metric against a predefined threshold.

164. The method of embodiment 163, wherein the correlation metric is a P value.

165. The method of any of embodiments 144-146, wherein the covariant is an adverse side effect and wherein the patient subgroup of interest is a subgroup that has a significant association with experiencing the adverse side effect after a treatment.

166. The method of embodiment 165, wherein associating each patient subgroup of the one or more patient subgroups with the covariant comprises: generating, for a patient subgroup, a model configured to receive an indication of whether a patient in the patient subgroup has received the treatment and predict if the patient has the adverse side effect; and evaluating the model to determine if the patient subgroup is the patient subgroup of interest.

167. A system, comprising: one or more processors; a memory; and one or more programs, wherein the one or more programs are stored in the memory and configured to be executed by the one or more processors, the one or more programs including instructions for performing the method of any of embodiments 1-166.

168. A non-transitory computer-readable storage medium storing one or more programs, the one or more programs comprising instructions, which when executed by one or more processors of an electronic device, cause the electronic device to perform the method of any of embodiments 1-166.

What is claimed is:

1. A system for evaluating a treatment with respect to progression of a disease of interest, comprising:
    one or more processors;
    a memory; and
    one or more programs, wherein the one or more programs are stored in the memory and configured to be executed by the one or more processors, the one or more programs including instructions for:
        obtaining a plurality of baseline placebo medical images of a placebo group of subjects captured before a placebo is administered to the placebo group of subjects and a plurality of follow-up placebo medical images of the placebo group of subjects captured after the placebo is administered to the placebo group of subjects;
        generating a plurality of baseline placebo embeddings in a latent space based on the plurality of baseline placebo medical images;
        generating a plurality of follow-up placebo embeddings in the latent space based on the plurality of follow-up placebo medical images;
        inputting the plurality of baseline placebo embeddings into one or more machine learning models to obtain a plurality of predicted follow-up placebo embeddings in the latent space;
        obtaining a plurality of placebo progression embeddings based on the plurality of follow-up placebo embeddings and the plurality of predicted follow-up placebo embeddings;
        obtaining a plurality of baseline treatment medical images of a treatment group of subjects captured before the treatment is administered to the treatment group of subjects and a plurality of follow-up treatment medical images of the treatment group of subjects captured after the treatment is administered to the treatment group of subjects;
        generating a plurality of treatment placebo embeddings in the latent space based on the plurality of baseline treatment medical images;
        generating a plurality of follow-up treatment embeddings in the latent space based on the plurality of follow-up treatment medical images;
        inputting the plurality of baseline treatment embeddings into the one or more machine learning models to obtain a plurality of predicted follow-up treatment embeddings in the latent space;
        obtaining a plurality of treatment progression embeddings based on the plurality of follow-up treatment embeddings and the plurality of predicted follow-up treatment embeddings; and
        generating a classification model for determining whether a patient has received the placebo or the treatment based on the plurality of treatment progression embeddings and the plurality of placebo progression embeddings.

2. The system of claim 1, wherein outputs of the classification model are indicative of drug response phenotype.

3. The system of claim 1, wherein the one or more programs further include instructions for:
determining, based on the classification model, a correlation metric between the treatment and the progression of the disease of interest.

4. The system of claim 3, wherein the correlation metric is a P value.

5. The system of claim 3, wherein the one or more programs further include instructions for:
comparing the correlation metric with a predefined threshold.

6. The system of claim 5, wherein the one or more programs further include instructions for:
identifying, based on the comparison, an association between the treatment and progression of the disease of interest.

7. The system of claim 6, wherein the one or more programs further include instructions for:
prescribing the treatment in a new subject based on the association.

8. The system of claim 6, wherein the one or more programs further include instructions for:
administering the treatment based on the association.

9. The system of claim 6, wherein the one or more programs further include instructions for:
adjusting the treatment based on the association.

10. The system of claim 6, wherein the one or more programs further include instructions for:
providing a medical recommendation based on the association.

11. The system of claim 6, wherein the one or more programs further include instructions for:
generating a report based on the association.

12. The system of claim 1, wherein the disease of interest is non-alcoholic steatohepatitis (NASH).

13. The system of claim 1, wherein:
the plurality of baseline placebo embeddings are generated by inputting the plurality of baseline placebo medical images into a trained unsupervised machine-learning model;
the plurality of follow-up placebo embeddings are generated by inputting the plurality of follow-up placebo medical images into the trained unsupervised machine-learning model; and
the plurality of placebo progression embeddings are determined by calculating differences between the plurality of follow-up placebo embeddings and the plurality of predicted follow-up placebo embeddings.

14. The system of claim 13, wherein the one or more machine learning models comprise a trained linear model.

15. The system of claim 14, wherein the trained linear model is configured to receive a baseline embedding and output a predicted follow-up embedding.

16. The system of claim 15, wherein the trained linear model is a linear mixed model.

17. The system of claim 15, wherein the placebo group of subjects is a first placebo group, and wherein the trained linear model is trained using medical image data from a second placebo group different from the first placebo group.

18. The system of claim 13, wherein the one or more machine learning models include the trained unsupervised machine-learning model.

19. The system of claim 13, wherein the plurality of baseline treatment embeddings are generated by inputting the plurality of baseline treatment medical images into the trained unsupervised machine-learning model;
the plurality of follow-up treatment embeddings are generated by inputting the plurality of follow-up treatment medical images into the trained unsupervised machine-learning model; and
the plurality of treatment progression embeddings are determined by calculating differences between the plurality of follow-up treatment embeddings and the plurality of predicted follow-up treatment embeddings.

20. The system of claim 13, wherein the trained unsupervised machine-learning model is a contrastive model.

21. The system of claim 20, wherein the contrastive model is a SimCLR model.

22. The system of claim 1, wherein the classification model is configured to receive an input progression embedding and output a classification result indicating whether a patient has received the placebo or the treatment.

23. The system of claim 1, wherein the plurality of baseline placebo medical images, the plurality of follow-up placebo medical images, the plurality of baseline treatment medical images, and the plurality of follow-up treatment images are biopsy medical images.

* * * * *